United States Patent
Tanaka et al.

(10) Patent No.: US 8,673,647 B2
(45) Date of Patent: Mar. 18, 2014

(54) STRESS EVALUATING APPARATUS, METHOD, SYSTEM AND PROGRAM AND RECORDING MEDIUM THEREFOR

(75) Inventors: Takayuki Tanaka, Kawasaki (JP); Yukio Nihei, Kawasaki (JP); Toshihiko Ando, Kawasaki (JP); Minoru Yamakado, Tokyo (JP); Keita Takamatsu, Mitaka (JP); Eiko Takahashi, Mitaka (JP); Norio Sasamori, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 78 days.

(21) Appl. No.: 12/365,270

(22) Filed: Feb. 4, 2009

(65) Prior Publication Data

US 2009/0234586 A1   Sep. 17, 2009

Related U.S. Application Data

(63) Continuation of application No. PCT/JP2007/065139, filed on Aug. 2, 2007.

(30) Foreign Application Priority Data

Aug. 4, 2006   (JP) ................. 2006-213918

(51) Int. Cl.
*G01N 33/00* (2006.01)
(52) U.S. Cl.
USPC .............. 436/89; 436/86; 436/183; 436/811; 702/19
(58) Field of Classification Search
USPC .......................... 436/86, 89, 183, 811; 702/19
See application file for complete search history.

(56) References Cited

U.S. PATENT DOCUMENTS

| | | | |
|---|---|---|---|
| 7,005,255 B2 | 2/2006 | Kaddurah-Daouk et al. | |
| 7,329,489 B2 | 2/2008 | Kaddurah-Daouk et al. | |
| 2002/0009740 A1 | 1/2002 | Kaddurah-Daouk et al. | |
| 2003/0077833 A1 | 4/2003 | Campbell et al. | |
| 2004/0146853 A1 | 7/2004 | Kaddurah-Daouk et al. | |
| 2004/0254122 A1* | 12/2004 | Hayes et al. .................. | 514/23 |
| 2005/0014132 A1 | 1/2005 | Kaddurah-Daouk et al. | |
| 2005/0283347 A1 | 12/2005 | Kimura et al. | |
| 2006/0134676 A1 | 6/2006 | Kaddurah-Daouk et al. | |
| 2006/0134677 A1 | 6/2006 | Kaddurah-Daouk et al. | |

(Continued)

FOREIGN PATENT DOCUMENTS

| | | |
|---|---|---|
| CA | 2 443 806 A1 | 10/2002 |
| JP | 06-102163 A | 4/1994 |

(Continued)

OTHER PUBLICATIONS

Joseph, M. S. et al, Psychiatry Research 1984, 11, 185-192.*

(Continued)

*Primary Examiner* — Arlen Soderquist
(74) *Attorney, Agent, or Firm* — Foley & Lardner LLP

(57) ABSTRACT

According to the method of evaluating stress of the present invention, amino acid concentration data on the concentration value of amino acid in blood collected from a subject to be evaluated is measured, and a stress state including at least depressive illness and major depressive illness in the subject is evaluated based on the concentration value of at least one of Lys, His, ABA, Asn, Phe, Leu, Ile, Val, Trp, Tyr and Met contained in the measured amino acid concentration data of the subject.

31 Claims, 55 Drawing Sheets

(56) References Cited

U.S. PATENT DOCUMENTS

| | | | |
|---|---|---|---|
| 2006/0134678 | A1 | 6/2006 | Kaddurah-Daouk et al. |
| 2007/0026389 | A1 | 2/2007 | Kaddurah-Daouk et al. |
| 2007/0072203 | A1 | 3/2007 | Kaddurah-Daouk et al. |
| 2007/0134156 | A1 | 6/2007 | Mizuno et al. |
| 2007/0172820 | A1 | 7/2007 | Kaddurah-Daouk et al. |
| 2007/0172885 | A1 | 7/2007 | Kaddurah-Daouk et al. |
| 2007/0178599 | A1 | 8/2007 | Kaddurah-Daouk et al. |
| 2007/0298998 | A1 | 12/2007 | Paige et al. |
| 2008/0131921 | A1 | 6/2008 | Myint et al. |
| 2008/0147368 | A1* | 6/2008 | Sugimoto et al. ............... 703/11 |
| 2008/0154515 | A1* | 6/2008 | Zhang et al. .................... 702/19 |
| 2009/0017464 | A1 | 1/2009 | Kaddurah-Daouk et al. |
| 2009/0297494 | A1 | 12/2009 | Cuenod et al. |
| 2010/0062413 | A1* | 3/2010 | Muramatsu et al. .............. 435/2 |
| 2010/0173348 | A1* | 7/2010 | Tanaka et al. ................... 435/29 |
| 2010/0280809 | A1* | 11/2010 | Takahashi et al. ............. 703/11 |
| 2011/0035156 | A1* | 2/2011 | Imaizumi et al. ............... 702/19 |

FOREIGN PATENT DOCUMENTS

| | | |
|---|---|---|
| JP | 11-128175 A | 5/1999 |
| JP | 3070346 B2 | 5/2000 |
| JP | 2002-107363 A | 4/2002 |
| JP | 2003-079602 A | 3/2003 |
| JP | 3429043 B2 | 5/2003 |
| JP | 3445038 B2 | 6/2003 |
| JP | 2003-274959 A | 9/2003 |
| JP | 2004-061436 A | 2/2004 |
| JP | 2004-208547 A | 7/2004 |
| JP | 2005-004398 A | 1/2005 |
| JP | 2005-143420 A | 6/2005 |
| JP | 2005-312435 A | 11/2005 |
| JP | 2006-000015 A | 1/2006 |
| WO | WO 92/13273 A1 | 8/1992 |
| WO | WO 01/78652 A2 | 10/2001 |
| WO | WO 2004/052191 A1 | 6/2004 |
| WO | WO 2005/007408 A2 | 1/2005 |
| WO | WO 2005/068649 A1 | 7/2005 |
| WO | WO 2005/078448 A1 | 8/2005 |
| WO | WO 2006/098192 A1 | 9/2006 |
| WO | WO 2007/134028 A2 | 11/2007 |

OTHER PUBLICATIONS

Honig, A. et al, Journal of Psychiatric Research 1988, 22, 159-164.*
Eriksson T. et al, Journal of Psychiatric Research 1989, 23, 241-249.*
Russ, M. J. et al, Journal of Affective Disorders 1990, 19, 9-14.*
Anderson, I. M. et al, Journal of Affective Disorders 1990, 20, 185-191.*
Macciardi, F. et al, Psychiatry Research 1990, 32, 63-70.*
Lucca, A. et al, Psychiatry Research 1992, 44, 85-91.*
Kawakita, H., Journal of Tokyo Medical College 1994, 52, 135-144.*
Parvy, P. et al, Clinica Chimica Acta 1995, 235, 1-10.*
Lucca, A. et al, Progress in Neuro-Psychopharmacology & Biological Psychiatry 1995, 19, 615-626.*
Altamura, C. et al, European Neuropsychopharmacology Supplement 1995, 71-75.*
Lucini, V. et al, Journal of Affective Disorders 1996, 36, 129-133.*
Bellodi, L. et al, Psychiatry Research 1997, 69, 9-15.*
Fekkes, D. et al, European Neuropsychopharmacology 1997, 7, 235-239.*
Maes, M. et al, Acta Psychiatrica Scandinavica 1998, 97, 302-308.*
Moreno, F. A. et al, Biological Psychiatry 2000, 48, 327-329.*
Sanacora, G. et al, Archives of General Psychiatry 2004, 61, 705-713.*
Mitani, H. et al, Progress in Neuro-Psychopharmacology & Biological Psychiatry 2006, 30, 1155-1158.*
Noguchi et al., "Network analysis of plasma and tissue amino acids and the generation of an amino index for potential diagnostic use," Am. J. Clin. Nutr., 2006, 83(supp):513S-519S.
Maes et al., "Symptom profiles of biological markers in depression: A multivariate study," Psychoneuroendocrinology, 1990, 15(1):29-37.
Tanaka et al., "Usefulness of Blood Amino Acids Measurements for Stress Examination during Ningen Dock (Comprehensive Medical Examination)," Official Journal of Japan Society of Ningen Dock; Jun. 29, 2007, 22(1):24-27, with English translation, 10 pages.
Caballero et al., "Plasma amino acid concentrations in healthy elderly men and women," Am. J. Clin. Nutr., 1991, 53(5):1249-1252.

* cited by examiner (BASIC PRINCIPLE OF THE INVENTION)

(BASIC PRINCIPLE OF THE INVENTION)

| USER ID | USER PASSWORD | NAME | ORGAN- IZATION ID | DEPART- MENT ID | DEPART- MENT NAME | E-MAIL ADDRESS | ... |
|---|---|---|---|---|---|---|---|
| ⋮ | ⋮ | ⋮ | ⋮ | ⋮ | ⋮ | ⋮ | ⋮ |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| ⋮ | ⋮ | ⋮ | ⋮ | ⋮ | ⋮ | ⋮ |

FIG.9

| INDIVIDUAL (SAMPLE) NO. | STRESS STATE INDEX DATA (T) | | | | AMINO ACID CONCENTRATION DATA | | | | | 106c |
| --- | --- | --- | --- | --- | --- | --- | --- | --- | --- | --- |
| | $T_1$ | $T_2$ | $T_3$ | ... | Gly | Leu | Val | Ile | Phe | ... |
| A-1 | 23.4 | 62.5 | 37.1 | ... | 9.5 | 11.2 | 2.7 | 8.5 | 4.9 | ... |
| A-2 | 27.5 | 66.1 | 39.5 | ... | 8.5 | 10.5 | 3.9 | 9.8 | 6.1 | ... |
| ... | ... | ... | ... | ... | ... | | | | | |

FIG.10

| INDIVIDUAL (SAMPLE) NO. | STRESS STATE INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | | | | |

| RANK | CANDIDATE MULTIVARIATE DISCRIMINANT |
|---|---|
| 1 | $F_1$(Gly,Leu,Phe,...) |
| 2 | $F_2$(Gly,Leu,Phe,...) |
| 3 | $F_3$(Gly,Leu,Phe,...) |
| ⋮ | ⋮ |

| RANK | CANDIDATE MULTIVARIATE DISCRIMINANT | VERIFICATION RESULT |
|---|---|---|
| 1 | $F_k$(Gly,Leu,Phe,...) | 1.22 |
| 2 | $F_m$(Gly,Leu,Phe,...) | 2.28 |
| 3 | $F_l$(Gly,Leu,Phe,...) | 2.95 |
| ⋮ | ⋮ | ⋮ |

| INDIVIDUAL (SAMPLE) NO. | STRESS STATE INDEX DATA (T) | AMINO ACID CONCENTRATION DATA | |
|---|---|---|---|
| | $T_2$ | Leu | Phe | ... |
| A-1 | 62.5 | 11.2 | 4.9 | ... |
| A-2 | 66.1 | 10.5 | 6.1 | ... |
| ⋮ | ⋮ | ⋮ | ⋮ | ⋮ |

| RANK | MULTIVARIATE DISCRIMINANT | THRESHOLD VALUE | VERIFICATION RESULT |
|---|---|---|---|
| 1 | $F_p$(Phe,...) | 0.23 | 0.62 |
| 2 | $F_p$(Gly,Leu,Phe) | -2.12 | 1.02 |
| 3 | $F_k$(Gly,Leu,Phe,...) | 1.23 | 1.22 |
| ⋮ | ⋮ | ⋮ | ⋮ |

| INDIVIDUAL (SAMPLE) NO. | RANK | DISCRIMINANT VALUE |
|---|---|---|
| U-1 | 1 | 1.13 |
| ⋮ | ⋮ | ⋮ |

106f

| INDIVIDUAL (SAMPLE) NO. | AMINO ACID CONCENTRATION DATA | | | | DIS-CRIMINANT VALUE | EVAL-UATION RESULT |
|---|---|---|---|---|---|---|
| | Gly | Leu | Phe | ... | | |
| U-1 | 9.5 | 11.2 | 4.9 | ... | | |
| U-2 | 8.5 | 10.5 | 6.1 | ... | | |
| ⋮ | ⋮ | ⋮ | ⋮ | ⋮ | | |

| RANK | VALUE | FORMULA |
|---|---|---|
| 1 | 0.788 | (4.038480)−(0.037974)Ser+(0.047874)Glu+(0.099284)Ile−(0.071109)Leu |
| 2 | 0.786 | −(0.850472)−(0.072327)Asn+(0.044777)Glu−(0.232122)Met+(0.134977)Phe |
| 3 | 0.784 | −(2.818593)+(0.059536)Glu−(0.015318)Val−(0.246995)Met+(0.166246)Phe |
| 4 | 0.782 | −(3.220995)+(0.059555)Glu−(0.259571)Met−(0.027288)Leu+(0.177187)Phe |
| 5 | 0.781 | −(0.151361)−(0.101798)Asn+(0.055191)Glu−(0.020564)Val+(0.109162)Phe |
| 6 | 0.781 | (1.245429)−(0.025150)Ser+(0.044562)Glu+(0.062076)Phe−(0.023113)Lys |
| 7 | 0.779 | (0.721090)−(0.030601)Ser+(0.056270)Glu−(0.022022)Val+(0.077597)Phe |
| 8 | 0.779 | (3.649910)−(0.036075)Ser+(0.040528)Glu+(0.036385)Orn−(0.021327)Lys |
| 9 | 0.779 | (1.832525)−(0.024827)Ser+(0.039955)Glu−(0.240779)Met+(0.077679)Tyr |
| 10 | 0.777 | (0.275190)−(0.081551)Asn+(0.042819)Glu+(0.082160)Phe−(0.019023)Lys |
| 11 | 0.776 | (2.831727)−(0.077012)Asn+(0.047121)Glu−(0.023704)Val+(0.053963)Ile |
| 12 | 0.776 | (2.321195)−(0.026399)Ser+(0.041978)Glu+(0.043076)Tyr−(0.023267)Lys |
| 13 | 0.776 | (3.739386)−(0.032466)Ser+(0.049824)Glu−(0.028241)Val+(0.054793)Ile |
| 14 | 0.775 | −(2.133396)+(0.049575)Glu−(0.225023)Met+(0.140744)Phe−(0.013773)Lys |
| 15 | 0.775 | −(2.833375)+(0.044118)Glu−(0.372740)Met+(0.064207)Tyr+(0.106497)Phe |
| 16 | 0.774 | −(0.055284)−(0.022376)Ser+(0.045453)Glu−(0.253326)Met+(0.116811)Phe |
| 17 | 0.774 | (3.261052)−(0.038097)Ser+(0.048707)Glu−(0.014499)Val+(0.023833)Orn |
| 18 | 0.773 | (1.198523)+(0.048960)Glu−(0.004275)Gly−(0.026865)Val+(0.051469)Ile |
| 19 | 0.773 | (0.940945)−(0.063223)Asn+(0.040085)Glu−(0.209487)Met+(0.080215)Tyr |
| 20 | 0.773 | −(0.690639)−(0.108045)Asn+(0.054478)Glu−(0.035668)Leu+(0.119832)Phe |
| 21 | 0.773 | −(0.046079)+(0.044107)Glu−(0.204591)Met+(0.090223)Tyr−(0.014346)Lys |
| 22 | 0.772 | (1.800661)−(0.022388)Thr+(0.049222)Glu−(0.024956)Val+(0.060228)Ile |
| 23 | 0.772 | (1.032880)+(0.042907)Glu−(0.003835)Gly+(0.017471)Orn−(0.017916)Lys |
| 24 | 0.772 | −(1.387580)+(0.039410)Glu+(0.003350)Ala−(0.278018)Met+(0.083442)Tyr |
| 25 | 0.772 | (1.818485)−(0.026222)Thr+(0.047458)Glu+(0.094823)Ile−(0.059053)Leu |
| 26 | 0.772 | (3.267707)−(0.029979)Ser+(0.040916)Glu+(0.005196)Pro−(0.015138)Lys |
| 27 | 0.772 | (1.381797)+(0.041380)Glu−(0.005167)Gln−(0.236411)Met+(0.084739)Tyr |
| 28 | 0.771 | (4.492154)−(0.025533)Ser−(0.047784)Asn+(0.043235)Glu−(0.010113)Lys |
| 29 | 0.770 | (3.399080)−(0.029951)Ser+(0.046215)Glu−(0.017142)Lys+(0.007847)Arg |
| 30 | 0.770 | (0.255749)−(0.032942)Ser+(0.055466)Glu−(0.038492)Leu+(0.086924)Phe |
| 31 | 0.770 | (0.071415)−(0.024675)Thr+(0.049341)Glu−(0.011854)Val+(0.042802)Tyr |
| 32 | 0.770 | −(0.157770)+(0.040916)Glu−(0.002442)Gly−(0.259144)Met+(0.082655)Tyr |
| 33 | 0.769 | −(0.651389)+(0.045092)Glu−(0.003922)Val−(0.242938)Met+(0.084816)Tyr |
| 34 | 0.769 | −(3.734712)+(0.043103)Glu+(0.005197)Ala−(0.321810)Met+(0.140551)Phe |

FIG.25

| RANK | VALUE | FORMULA |
|---|---|---|
| 35 | 0.768465 | (2.894800)−(0.027805)Ser+(0.042742)Glu+(0.002561)Ala−(0.015962)Lys |
| 36 | 0.768465 | (0.794825)+(0.048467)Glu−(0.021481)Val−(0.073212)Met+(0.054012)Ile |
| 37 | 0.768203 | −(0.102046)−(0.015417)Thr+(0.041776)Glu−(0.209662)Met+(0.079495)Tyr |
| 38 | 0.768203 | (2.542224)−(0.080621)Asn+(0.045462)Glu+(0.072791)Ile−(0.048614)Leu |
| 39 | 0.768203 | −(0.599049)+(0.040914)Glu−(0.253063)Met+(0.087957)Tyr−(0.007420)Arg |
| 40 | 0.768203 | (1.463225)−(0.074126)Asn+(0.040696)Glu+(0.050381)Tyr−(0.018738)Lys |
| 41 | 0.767941 | (4.876098)−(0.027719)Ser−(0.054256)Asn+(0.049036)Glu−(0.009645)Val |
| 42 | 0.767417 | −(1.123681)+(0.037226)Glu+(0.006591)Pro−(0.283870)Met+(0.088056)Tyr |
| 43 | 0.767417 | −(0.477366)+(0.042631)Glu−(0.028435)ABA−(0.255628)Met+(0.085473)Tyr |
| 44 | 0.767417 | −(0.511997)+(0.042244)Glu−(0.014323)Cit−(0.262406)Met+(0.086552)Tyr |
| 45 | 0.767417 | (0.462188)+(0.048441)Glu−(0.025224)Val+(0.053858)Ile−(0.008698)Arg |
| 46 | 0.767156 | (3.443922)−(0.008399)Thr−(0.025328)Ser+(0.044790)Glu−(0.011121)Lys |
| 47 | 0.767156 | −(1.452166)−(0.021121)Thr+(0.057125)Glu−(0.018506)Val+(0.086255)Phe |
| 48 | 0.767156 | (3.456027)−(0.029011)Ser+(0.044841)Glu+(0.000678)Cit−(0.014229)Lys |
| 49 | 0.767156 | −(1.848998)+(0.047834)Glu−(0.274738)Met+(0.145691)Phe−(0.022668)His |
| 50 | 0.767156 | (3.468012)−(0.028983)Ser+(0.044832)Glu−(0.014192)Lys |
| 51 | 0.767156 | (0.883679)+(0.049477)Glu−(0.019782)Val+(0.048170)Ile−(0.010716)Lys |
| 52 | 0.767156 | (3.270740)−(0.028634)Ser+(0.044604)Glu+(0.005836)Trp−(0.014795)Lys |
| 53 | 0.766894 | (3.606877)−(0.012061)Thr−(0.027586)Ser+(0.049960)Glu−(0.016038)Leu |
| 54 | 0.766894 | −(0.646670)+(0.046365)Glu−(0.004869)Gln−(0.250881)Met+(0.130234)Phe |
| 55 | 0.766894 | (3.640125)−(0.011441)Thr−(0.026814)Ser+(0.050542)Glu−(0.009705)Val |
| 56 | 0.766632 | −(0.738773)+(0.044237)Glu−(0.249940)Met−(0.004745)Leu+(0.085141)Tyr |
| 57 | 0.76637 | (3.503603)−(0.028650)Ser+(0.045015)Glu−(0.006649)ABA−(0.013855)Lys |
| 58 | 0.76637 | (0.745182)−(0.021235)Thr+(0.044185)Glu−(0.043298)Met+(0.007806)Orn |
| 59 | 0.76637 | (3.683428)−(0.028901)Ser+(0.045373)Glu−(0.034347)Met−(0.010841)Lys |
| 60 | 0.766108 | (0.993901)+(0.046927)Glu−(0.005164)Gly+(0.076772)Ile−(0.057767)Leu |
| 61 | 0.766108 | −(0.926584)+(0.037668)Glu−(0.299382)Met+(0.016774)Ile+(0.038821)Tyr |
| 62 | 0.766108 | (3.437320)−(0.028863)Ser+(0.044457)Glu+(0.001513)Ile−(0.014472)Lys |
| 63 | 0.765846 | (0.549788)+(0.041457)Glu−(0.003886)Gly+(0.004346)Ala−(0.017421)Lys |
| 64 | 0.765846 | (0.992171)−(0.022620)Thr+(0.049114)Glu−(0.007794)Val+(0.011807)Orn |
| 65 | 0.765846 | (3.451946)−(0.031881)Ser+(0.045575)Glu+(0.001460)Gly−(0.014481)Lys |
| 66 | 0.765584 | (3.223669)−(0.034321)Ser+(0.046622)Glu+(0.007648)Pro−(0.013833)Val |
| 67 | 0.765322 | −(0.794012)+(0.042124)Glu−(0.264535)Met+(0.086098)Tyr−(0.001683)Trp |
| 68 | 0.765322 | (0.503436)−(0.107495)Asn+(0.038778)Glu−(0.049178)ABA+(0.056187)Phe |

FIG.26

| RANK | VALUE | FORMULA |
|---|---|---|
| 69 | 0.76506 | (0.708776)+(0.049263)Glu-(0.004720)Gly-(0.011920)Val+(0.006832)Orn |
| 70 | 0.76506 | -(0.397714)+(0.043027)Glu+(0.003692)Ala+(0.011928)Orn-(0.020190)Lys |
| 71 | 0.76506 | (4.006096)-(0.030788)Ser+(0.050214)Glu-(0.007143)Val-(0.009292)Lys |
| 72 | 0.764798 | -(3.204548)+(0.041563)Glu+(0.007929)Pro-(0.311973)Met+(0.141302)Phe |
| 73 | 0.764798 | (3.748353)-(0.031441)Ser+(0.050147)Glu-(0.008503)Val-(0.044522)Met |
| 74 | 0.764536 | (0.242426)-(0.019050)Thr+(0.043121)Glu+(0.049790)Tyr-(0.018454)Lys |
| 75 | 0.764536 | (2.903920)-(0.031835)Ser+(0.049452)Glu+(0.001789)Ala-(0.012469)Val |
| 76 | 0.764536 | -(0.706268)+(0.042743)Glu-(0.261635)Met+(0.086208)Tyr-(0.004761)Orn |
| 77 | 0.764274 | (0.575853)-(0.020125)Thr+(0.044944)Glu-(0.049445)Met+(0.012881)Trp |
| 78 | 0.764274 | -(0.182839)-(0.114090)Asn+(0.033975)Glu+(0.003477)Pro+(0.050621)Phe |
| 79 | 0.764013 | (2.335149)-(0.031912)Ser+(0.049697)Glu-(0.015204)Val+(0.027903)Tyr |
| 80 | 0.764013 | -(0.331826)-(0.111962)Asn+(0.035293)Glu+(0.001566)Ala+(0.048986)Phe |
| 81 | 0.764013 | (4.793328)-(0.028622)Ser-(0.054772)Asn+(0.048260)Glu-(0.015723)Leu |
| 82 | 0.764013 | (4.112627)-(0.029987)Ser+(0.044989)Glu-(0.010336)His-(0.012688)Lys |
| 83 | 0.764013 | -(1.242230)+(0.045438)Glu-(0.001624)Gly+(0.069939)Phe-(0.024820)Lys |
| 84 | 0.764013 | (0.544570)+(0.047948)Glu+(0.062575)Ile-(0.038946)Leu-(0.011417)Lys |
| 85 | 0.764013 | -(2.801298)+(0.048294)Glu-(0.280917)Met-(0.004093)Ile+(0.136964)Phe |
| 86 | 0.763751 | (0.536506)-(0.022011)Thr+(0.048059)Glu+(0.003530)Ala-(0.008194)Val |
| 87 | 0.763751 | -(2.857489)+(0.046836)Glu-(0.288443)Met+(0.135310)Phe+(0.002913)Orn |
| 88 | 0.763751 | -(0.833333)+(0.042080)Glu-(0.265268)Met+(0.085756)Tyr |
| 89 | 0.763751 | (1.885564)-(0.021192)Ser-(0.087361)Asn+(0.035782)Glu+(0.040281)Phe |
| 90 | 0.763489 | (1.095316)+(0.044208)Glu-(0.003085)Gly+(0.003960)Ile-(0.015324)Lys |
| 91 | 0.763489 | -(2.306788)+(0.044271)Glu+(0.003491)Ala+(0.073865)Phe-(0.028466)Lys |
| 92 | 0.763489 | -(2.758128)+(0.047306)Glu-(0.284985)Met+(0.135391)Phe-(0.000880)Trp |
| 93 | 0.763489 | -(0.864002)+(0.042070)Glu-(0.265883)Met+(0.085734)Tyr+(0.000602)His |
| 94 | 0.763227 | (2.593326)-(0.012905)Thr-(0.053529)Asn+(0.048259)Glu-(0.006038)Val |
| 95 | 0.763227 | (0.276683)-(0.020034)Thr+(0.042393)Glu+(0.003709)Ala-(0.058873)Met |
| 96 | 0.763227 | -(2.774288)+(0.047269)Glu-(0.285417)Met+(0.135146)Phe |
| 97 | 0.762965 | (1.638949)-(0.029757)Ser+(0.017312)Pro-(0.273277)Met+(0.093553)Tyr |
| 98 | 0.762965 | -(0.206676)-(0.108315)Asn+(0.043258)Glu-(0.022027)Ile+(0.069851)Phe |
| 99 | 0.762965 | (3.969557)-(0.031471)Ser+(0.049683)Glu-(0.011591)Leu-(0.009541)Lys |
| 100 | 0.762703 | -(1.957013)-(0.023076)Thr+(0.056799)Glu-(0.032402)Leu+(0.096100)Phe |

FIG.28

| RANK | VALUE | FORMULA |
| --- | --- | --- |
| 1 | 0.960413 | (19.447723)−(0.052039)Gln+(0.072690)Pro−(0.264734)Trp+(0.089481)Arg |
| 2 | 0.958692 | (18.864429)−(0.050435)Gln+(0.090872)Pro+(0.163341)Tyr−(0.366640)Trp |
| 3 | 0.956971 | (18.871647)−(0.057395)Gln+(0.077186)Pro+(0.661676)Met−(0.394844)Trp |
| 4 | 0.950086 | (14.029132)−(0.033517)Gln−(0.387649)ABA+(0.741193)Met−(0.235396)Trp |
| 5 | 0.946644 | (16.834274)−(0.353723)Asn−(0.452739)ABA+(0.200574)Tyr−(0.201577)Trp |
| 6 | 0.946644 | (14.915527)−(0.591415)Asn+(0.024293)Ala+(0.451395)Met−(0.277747)Trp |
| 7 | 0.944923 | (14.307147)−(0.031104)Gln+(0.054992)Pro+(0.013092)Ala−(0.261382)Trp |
| 8 | 0.944923 | (17.808416)−(0.465407)Asn−(0.476979)ABA+(0.686434)Met−(0.224890)Trp |
| 9 | 0.943201 | (13.108127)−(0.479550)Asn+(0.022817)Ala+(0.122037)Tyr−(0.241562)Trp |
| 10 | 0.939759 | (16.079789)−(0.024036)Gln+(0.052247)Pro−(0.234559)ABA−(0.180179)Trp |
| 11 | 0.938038 | (14.710727)−(0.266235)Asn−(0.008376)Gln+(0.021090)Ala−(0.195964)Trp |
| 12 | 0.938038 | (12.603702)−(0.016923)Gln−(0.352988)ABA+(0.126998)Tyr−(0.166673)Trp |
| 13 | 0.936317 | (16.451850)−(0.044361)Gln+(0.070595)Pro−(0.283756)Trp+(0.044514)Lys |
| 14 | 0.936317 | (11.397359)+(0.045875)Ser−(0.455401)Asn+(0.023774)Ala−(0.185315)Trp |
| 15 | 0.934596 | (10.721997)−(0.025902)Gln+(0.022345)Ala−(0.245357)Trp+(0.070809)Orn |
| 16 | 0.934596 | (12.770377)−(0.032591)Gln+(0.062186)Pro+(0.049477)His−(0.217430)Trp |
| 17 | 0.934596 | (16.631796)−(0.028256)Gln−(0.310927)ABA−(0.143013)Trp+(0.087520)Arg |
| 18 | 0.934596 | (4.507030)+(0.052307)Ser−(0.351542)Asn−(0.262938)ABA+(0.106061)Tyr |
| 19 | 0.932874 | (19.435498)−(0.381127)Asn+(0.025682)Ala−(0.254139)ABA−(0.227893)Trp |
| 20 | 0.932874 | (10.635156)−(0.026199)Gln+(0.019280)Ala+(0.096131)Tyr−(0.261374)Trp |
| 21 | 0.932874 | (3.046752)+(0.035509)Pro−(0.573125)ABA+(0.121550)Tyr−(0.167207)Trp |
| 22 | 0.932874 | (12.997048)+(0.092797)Glu−(0.036215)Gln+(0.496920)Met−(0.281251)Trp |
| 23 | 0.932874 | (15.806470)+(0.021907)Thr−(0.035542)Gln+(0.062315)Pro−(0.220808)Trp |
| 24 | 0.931153 | (12.162563)−(0.423327)Asn+(0.023353)Ala−(0.189429)Trp+(0.039815)Arg |
| 25 | 0.931153 | (11.363999)+(0.058504)Glu−(0.021458)Gln+(0.014409)Ala−(0.213981)Trp |
| 26 | 0.931153 | (12.133827)−(0.031089)Gln+(0.016376)Ala−(0.212230)Trp+(0.065216)Arg |
| 27 | 0.931153 | (12.723267)+(0.037922)Ser−(0.034204)Gln+(0.062066)Pro−(0.210165)Trp |
| 28 | 0.931153 | (15.559351)−(0.036121)Gln+(0.061059)Pro−(0.228877)Trp+(0.061024)Orn |
| 29 | 0.929432 | (10.659887)−(0.038250)Gln+(0.042767)Pro−(0.346992)ABA+(0.091719)Arg |
| 30 | 0.929432 | (14.217831)+(0.032755)Glu−(0.029077)Gln+(0.049742)Pro−(0.198788)Trp |
| 31 | 0.927711 | (11.957869)−(0.403318)Asn+(0.022220)Ala+(0.071999)Phe−(0.203318)Trp |
| 32 | 0.927711 | (6.237031)−(0.305119)Asn+(0.007938)Gly−(0.261475)ABA+(0.108365)Tyr |
| 33 | 0.927711 | (13.334734)−(0.017627)Gln+(0.016160)Ala−(0.198165)ABA−(0.183922)Trp |
| 34 | 0.92599 | (8.490787)+(0.061825)Glu−(0.026787)Gln−(0.320817)ABA+(0.077594)Arg |

FIG.29

| RANK | VALUE | FORMULA |
|---|---|---|
| 35 | 0.92599 | (12.786570)−(0.035121)Gln+(0.021627)Ala+(0.399038)Met−(0.319193)Trp |
| 36 | 0.92599 | (13.083318)−(0.031981)Gln+(0.059755)Pro+(0.061812)Phe−(0.214370)Trp |
| 37 | 0.924269 | (10.140615)+(0.033234)Ser−(0.032273)Gln−(0.119878)Trp+(0.067110)Arg |
| 38 | 0.924269 | (14.099034)−(0.362779)Asn+(0.020414)Ala−(0.009217)Cit−(0.181755)Trp |
| 39 | 0.924269 | (1.624683)+(0.026429)Pro−(0.416160)ABA+(0.096240)Phe−(0.117183)Trp |
| 40 | 0.924269 | (12.598233)−(0.359433)Asn+(0.019921)Pro+(0.015087)Ala−(0.171749)Trp |
| 41 | 0.924269 | (2.962414)+(0.058241)Glu−(0.471436)ABA+(0.111159)Tyr−(0.137293)Trp |
| 42 | 0.924269 | (14.407625)−(0.029323)Gln+(0.058233)Pro−(0.001382)Leu−(0.193060)Trp |
| 43 | 0.924269 | (8.775972)−(0.023203)Gln+(0.006788)Gly+(0.093587)Tyr−(0.145504)Trp |
| 44 | 0.924269 | (13.404243)−(0.031167)Gln+(0.060472)Pro+(0.006948)Gly−(0.199408)Trp |
| 45 | 0.924269 | (14.250559)−(0.029675)Gln+(0.057529)Pro+(0.008328)Cit−(0.192598)Trp |
| 46 | 0.922547 | (10.087823)+(0.054851)Ser−(0.522001)Asn+(0.135959)Tyr−(0.126948)Trp |
| 47 | 0.922547 | (11.096367)−(0.400031)Asn+(0.028640)Pro+(0.106056)Tyr−(0.154425)Trp |
| 48 | 0.922547 | (14.365563)−(0.029331)Gln+(0.057837)Pro−(0.194244)Trp |
| 49 | 0.922547 | (12.821731)−(0.431777)Asn+(0.020974)Ala+(0.056616)His−(0.197136)Trp |
| 50 | 0.922547 | (14.353651)−(0.029343)Gln+(0.057766)Pro+(0.000222)Val−(0.194617)Trp |
| 51 | 0.922547 | (6.729337)−(0.261950)Asn+(0.022924)Pro−(0.304681)ABA+(0.074338)Tyr |
| 52 | 0.922547 | (13.782630)−(0.035813)Gln−(0.099982)Val+(0.270863)Ile+(0.083517)Arg |
| 53 | 0.920826 | (13.329170)+(0.073958)Glu−(0.030909)Gln−(0.178002)Trp+(0.064546)Arg |
| 54 | 0.920826 | (8.651625)+(0.034227)Ser−(0.023928)Gln+(0.020975)Ala−(0.212224)Trp |
| 55 | 0.920826 | (14.492854)−(0.249907)Asn+(0.033129)Pro−(0.281822)ABA−(0.126670)Trp |
| 56 | 0.920826 | (3.285392)−(0.464654)ABA+(0.061738)Ile+(0.107570)Tyr−(0.170185)Trp |
| 57 | 0.920826 | (13.781419)−(0.365447)Asn+(0.020531)Ala−(0.179468)Trp |
| 58 | 0.920826 | (11.754322)−(0.039900)Gln+(0.056565)Pro−(0.042663)Val+(0.089577)Arg |
| 59 | 0.919105 | (13.961757)+(0.014108)Thr−(0.403524)Asn+(0.021039)Ala−(0.186004)Trp |
| 60 | 0.919105 | (13.478184)−(0.380963)Asn+(0.020547)Ala−(0.186335)Trp+(0.006843)Lys |
| 61 | 0.919105 | (13.570751)−(0.364270)Asn+(0.020355)Ala+(0.001808)Val−(0.182467)Trp |
| 62 | 0.919105 | (11.447405)+(0.054321)Glu−(0.018519)Gln−(0.089097)Val+(0.206305)Ile |
| 63 | 0.917384 | (7.608770)+(0.037107)Ser−(0.026575)Gln+(0.109368)Tyr−(0.155866)Trp |
| 64 | 0.917384 | (11.825999)+(0.079946)Glu−(0.027203)Gln+(0.112250)Tyr−(0.221767)Trp |
| 65 | 0.917384 | (16.376314)−(0.290525)Asn−(0.331480)ABA−(0.112562)Trp+(0.045605)Arg |
| 66 | 0.917384 | (13.544173)−(0.363088)Asn+(0.020151)Ala+(0.003680)Leu−(0.182283)Trp |
| 67 | 0.917384 | (15.483988)−(0.114754)Asn−(0.022641)Gln+(0.052821)Pro−(0.176125)Trp |
| 68 | 0.915663 | (21.053721)−(0.597957)Asn−(0.157656)Cit+(0.654792)Met−(0.237412)Trp |

FIG.30

| RANK | VALUE | FORMULA |
|---|---|---|
| 69 | 0.915663 | (8.163100)-(0.024477)Gln+(0.003851)Gly-(0.267430)ABA+(0.068603)Arg |
| 70 | 0.915663 | (6.639368)+(0.035565)Ser-(0.026880)Gln-(0.317559)ABA+(0.076000)Arg |
| 71 | 0.915663 | (17.268479)-(0.373880)Asn-(0.021030)Gln+(0.677121)Met-(0.226117)Trp |
| 72 | 0.915663 | (12.232659)-(0.018039)Gln+(0.017732)Ala-(0.040561)His-(0.179114)Trp |
| 73 | 0.915663 | (12.600614)-(0.034478)Gln+(0.255156)Met-(0.175663)Trp+(0.050192)Arg |
| 74 | 0.915663 | (8.194563)-(0.033187)Gln+(0.048711)Pro-(0.045507)Leu+(0.062788)Arg |
| 75 | 0.913941 | (13.052589)-(0.375858)Asn+(0.020715)Ala-(0.181369)Trp+(0.021497)Orn |
| 76 | 0.913941 | (11.142008)-(0.355991)Asn-(0.293584)ABA-(0.020456)Val+(0.411874)Met |
| 77 | 0.913941 | (8.668104)+(0.042652)Glu-(0.020249)Gln+(0.035481)Pro-(0.032991)Val |
| 78 | 0.913941 | (0.667083)+(0.053527)Glu-(0.379326)ABA+(0.119167)Phe-(0.108267)Trp |
| 79 | 0.913941 | (10.303126)-(0.022853)Gln+(0.017000)Ala-(0.210577)Trp+(0.016572)Lys |
| 80 | 0.913941 | (12.784547)-(0.341738)Asn-(0.019001)Glu+(0.017414)Ala-(0.171119)Trp |
| 81 | 0.913941 | (7.116256)-(0.244177)Asn+(0.032450)Glu-(0.290888)ABA+(0.078333)Tyr |
| 82 | 0.913941 | (11.725072)-(0.023618)Gln+(0.014873)Ala+(0.099239)Ile-(0.276496)Trp |
| 83 | 0.913941 | (11.101239)-(0.026322)Gln-(0.241178)ABA-(0.024442)Lys+(0.101348)Arg |
| 84 | 0.91222 | (14.260743)-(0.022313)Gln-(0.260419)ABA-(0.089508)His+(0.073672)Arg |
| 85 | 0.91222 | (16.661035)-(0.435797)ABA+(0.134325)Tyr-(0.175229)His-(0.144306)Trp |
| 86 | 0.91222 | (6.187465)-(0.029304)Thr+(0.029799)Pro-(0.280967)ABA-(0.094258)Trp |
| 87 | 0.91222 | (1.856638)+(0.035481)Ser+(0.045012)Glu-(0.027305)Gln+(0.049715)Arg |
| 88 | 0.91222 | -(4.004055)-(0.259131)ABA+(0.334054)Ile-(0.233996)Leu+(0.232529)Phe |
| 89 | 0.91222 | (10.976902)-(0.453744)Asn+(0.007738)Gly+(0.140656)Tyr-(0.121239)Trp |
| 90 | 0.91222 | (9.978447)-(0.020772)Gln+(0.004586)Gly+(0.017188)Ala-(0.189780)Trp |
| 91 | 0.910499 | (4.980478)-(0.019068)Gln+(0.343538)Ile-(0.233132)Leu+(0.154751)Phe |
| 92 | 0.910499 | (10.351749)-(0.346703)Asn-(0.276991)ABA+(0.373047)Met-(0.027284)Leu |
| 93 | 0.910499 | (7.142587)+(0.038314)Glu-(0.020240)Gln+(0.035999)Pro-(0.045355)Leu |
| 94 | 0.910499 | (11.208657)-(0.029469)Gln+(0.005748)Gly-(0.118102)Trp+(0.062940)Arg |
| 95 | 0.910499 | (11.354211)-(0.030087)Gln+(0.060624)Tyr-(0.146769)Trp+(0.054647)Arg |
| 96 | 0.910499 | (3.121206)+(0.032368)Ser-(0.016035)Gln-(0.304447)ABA+(0.079037)Tyr |
| 97 | 0.910499 | (12.297036)-(0.335787)Asn-(0.016992)Ala+(0.039641)Ile-(0.196295)Trp |
| 98 | 0.910499 | (8.447780)-(0.251808)Asn-(0.240370)ABA+(0.105206)Tyr-(0.013499)Lys |
| 99 | 0.908778 | (10.084962)-(0.021832)Gln+(0.017060)Ala+(0.050059)Cit-(0.185871)Trp |
| 100 | 0.908778 | (7.063196)-(0.019596)Gln+(0.284708)Ile-(0.177813)Leu+(0.066142)Tyr |

FIG.32

| RANK | VALUE | FORMULA |
|---|---|---|
| 1 | 0.788895 | (2.274e-01)Glu-(5.301e-02)Val-(8.039e-01)Met+(5.396e-01)Phe-(7.188e+00) |
| 2 | 0.788371 | -(2.762e-01)Ser+(3.916e-01)Glu+(7.157e-01)Ile-(5.081e-01)Leu+(3.256e+01) |
| 3 | 0.783394 | -(2.394e-01)Asn+(1.874e-01)Glu-(8.323e-01)Met+(4.634e-01)Phe-(1.059e+00) |
| 4 | 0.782609 | -(6.060e-01)Asn+(3.808e-01)Glu-(1.350e-01)Val+(6.852e-01)Phe+(2.171e+00) |
| 5 | 0.782347 | -(9.295e-02)Ser+(1.727e-01)Glu-(9.305e-01)Met+(3.093e-01)Tyr+(8.372e+00) |
| 6 | 0.782347 | (2.170e-01)Glu-(8.074e-01)Met-(8.581e-02)Leu+(5.419e-01)Phe-(8.295e+00) |
| 7 | 0.781037 | -(4.911e-01)Ser+(6.311e-01)Glu+(5.204e-01)Orn-(2.995e-01)Lys+(5.709e+01) |
| 8 | 0.780775 | -(2.900e-01)Ser+(5.552e-01)Glu+(7.340e-01)Phe-(2.625e-01)Lys+(1.952e+01) |
| 9 | 0.77999 | -(2.689e-01)Ser+(5.710e-01)Glu-(2.056e-01)Val+(7.479e-01)Phe+(8.651e+00) |
| 10 | 0.77999 | -(1.286e-01)Glu+(9.406e-01)Met-(1.726e-01)Tyr-(2.625e-01)Phe+(6.180e+00) |
| 11 | 0.779204 | (2.414e-01)Thr-(6.145e-01)Glu+(2.938e-01)Val-(6.912e-01)Ile-(2.656e+01) |
| 12 | 0.777894 | (6.628e-01)Glu-(5.293e-02)Gly-(3.410e-01)Val+(6.645e-01)Ile+(2.113e+01) |
| 13 | 0.777632 | -(6.843e-01)Asn+(4.727e-01)Glu-(2.245e-01)Val+(5.078e-01)Ile+(3.063e+01) |
| 14 | 0.777108 | -(3.479e-01)Ser+(6.010e-01)Glu-(3.230e-01)Val+(6.429e-01)Ile+(4.637e+01) |
| 15 | 0.776847 | -(7.760e-02)Ser+(1.860e-01)Glu-(8.911e-01)Met+(4.065e-01)Phe+(1.553e+00) |
| 16 | 0.776847 | (2.117e-01)Glu-(8.323e-01)Met+(5.097e-01)Phe-(5.161e-02)Lys-(5.506e+00) |
| 17 | 0.776585 | -(6.192e-01)Asn+(3.841e-01)Glu+(6.662e-01)Phe-(1.591e-01)Lys+(5.909e+00) |
| 18 | 0.775799 | -(3.659e-01)Ser+(6.113e-01)Glu+(6.292e-01)Tyr-(3.107e-01)Lys+(3.706e+01) |
| 19 | 0.775275 | -(1.996e-01)Thr+(4.155e-01)Glu+(7.520e-01)Ile-(4.712e-01)Leu+(1.800e+01) |
| 20 | 0.773442 | -(3.525e-01)Thr+(9.029e-01)Glu-(1.446e-01)Val+(1.991e-01)Orn+(2.489e+01) |
| 21 | 0.773442 | -(3.204e-01)Thr+(7.171e-01)Glu-(1.631e-01)Val+(5.971e-01)Tyr+(6.538e+00) |
| 22 | 0.772656 | -(2.316e-01)Asn+(1.878e-01)Glu-(8.920e-01)Met+(3.397e-01)Tyr+(5.028e+00) |
| 23 | 0.772656 | -(6.018e-01)Asn+(3.606e-01)Glu-(2.095e-01)Leu+(6.811e-01)Phe-(1.423e+00) |
| 24 | 0.772656 | (3.377e-01)Ser+(6.515e-01)Asn-(6.630e-01)Glu+(1.481e-01)Lys-(6.925e+01) |
| 25 | 0.772394 | (1.779e-01)Glu-(8.707e-01)Met+(4.534e-01)Phe-(6.889e-02)His-(4.335e+00) |
| 26 | 0.772394 | -(5.061e-01)Ser+(7.666e-01)Glu-(2.039e-01)Val+(3.385e-01)Orn+(4.954e+01) |
| 27 | 0.772132 | -(6.351e-02)Thr+(2.029e-01)Glu-(9.106e-01)Met+(3.543e-01)Tyr+(1.006e+00) |
| 28 | 0.77187 | (1.871e-01)Glu-(1.988e-02)Gln-(9.227e-01)Met+(3.365e-01)Tyr+(6.828e+00) |
| 29 | 0.77187 | (1.468e-01)Glu+(1.296e-02)Ala-(9.470e-01)Met+(2.853e-01)Tyr-(3.321e+00) |
| 30 | 0.771608 | -(2.725e-01)Ser+(5.245e-01)Glu-(3.227e-01)Leu+(7.392e-01)Phe+(5.004e+00) |
| 31 | 0.771608 | -(4.763e-01)Ser+(8.228e-01)Glu-(2.824e-01)Lys+(1.280e-01)Arg+(6.370e+01) |
| 32 | 0.771608 | (4.755e-01)Glu-(1.973e-01)Val-(6.938e-01)Met+(5.035e-01)Ile+(1.233e+01) |
| 33 | 0.771608 | (2.093e-01)Glu-(8.927e-01)Met+(3.948e-01)Tyr-(5.856e-02)Lys+(1.544e+00) |
| 34 | 0.771346 | (1.367e-01)Glu+(2.234e-02)Pro-(9.441e-01)Met+(2.990e-01)Tyr-(2.283e+00) |

FIG.33

| RANK | VALUE | FORMULA |
|---|---|---|
| 35 | 0.771084 | (1.421e-01)Glu+(1.614e-02)Ala-(9.114e-01)Met+(3.859e-01)Phe-(9.071e+00) |
| 36 | 0.770561 | (8.842e-01)Glu-(7.228e-02)Gly+(3.198e-01)Orn-(3.326e-01)Lys+(2.878e+01) |
| 37 | 0.770561 | -(4.020e-01)Ser+(7.211e-01)Glu-(5.411e-01)Met-(1.601e-01)Lys+(6.116e+01) |
| 38 | 0.770561 | (6.938e-01)Glu-(2.662e-01)Val+(6.548e-01)Ile-(1.382e-01)Lys+(1.821e+01) |
| 39 | 0.770299 | (3.156e-01)Ser+(6.715e-01)Asn-(6.602e-01)Glu+(1.166e-01)Val-(6.389e+01) |
| 40 | 0.770299 | -(5.290e-01)Ser+(7.987e-01)Glu+(9.039e-02)Pro-(2.723e-01)Lys+(6.847e+01) |
| 41 | 0.770299 | (1.910e-01)Glu-(1.792e-02)Gln-(8.733e-01)Met+(4.477e-01)Phe+(7.476e-02) |
| 42 | 0.770299 | -(2.578e-01)Thr+(6.741e-01)Glu-(6.868e-01)Met+(8.661e-02)Orn+(1.680e+01) |
| 43 | 0.770037 | (1.693e-01)Glu-(9.304e-01)Met+(3.244e-01)Tyr-(2.189e-02)Arg-(7.870e-01) |
| 44 | 0.769775 | (1.432e-01)Glu+(2.229e-02)Pro-(9.035e-01)Met+(4.033e-01)Phe-(7.635e+00) |
| 45 | 0.769775 | -(4.906e-01)Ser+(8.214e-01)Glu+(5.373e-02)Ala-(2.858e-01)Lys+(5.910e+01) |
| 46 | 0.769775 | (1.815e-01)Glu-(9.296e-01)Met-(1.532e-02)Leu+(3.205e-01)Tyr-(1.209e+00) |
| 47 | 0.769775 | (1.834e-01)Thr+(3.921e-01)Ser-(8.878e-01)Glu+(1.561e-01)Val-(6.301e+01) |
| 48 | 0.769513 | -(1.838e-01)Thr+(5.651e-01)Glu-(1.734e-01)Val+(7.854e-01)Phe-(8.365e+00) |
| 49 | 0.769513 | (9.291e-01)Glu-(8.412e-02)Gly+(8.904e-02)Ala-(3.490e-01)Lys+(2.164e+01) |
| 50 | 0.769251 | (1.908e-01)Glu-(1.472e-02)Val-(9.250e-01)Met+(3.283e-01)Tyr-(8.362e-01) |
| 51 | 0.768989 | -(2.042e-01)Thr+(5.396e-01)Glu+(4.636e-02)Ala-(8.155e-01)Met+(8.474e+00) |
| 52 | 0.768989 | (3.269e-01)Ser+(6.633e-01)Asn-(6.472e-01)Glu+(1.852e-01)Leu-(6.194e+01) |
| 53 | 0.768727 | -(7.020e-01)Asn+(4.488e-01)Glu+(5.191e-01)Tyr-(1.905e-01)Lys+(1.828e+01) |
| 54 | 0.768727 | (1.723e-01)Glu-(1.084e-01)ABA-(9.266e-01)Met+(3.163e-01)Tyr-(8.289e-02) |
| 55 | 0.768727 | (6.469e-01)Glu-(3.176e-01)Val-(6.861e-01)Ile-(9.933e-02)Arg+(1.136e+01) |
| 56 | 0.768465 | -(3.636e-01)Thr+(9.164e-01)Glu+(6.338e-02)Ala-(1.547e-01)Val+(1.796e+01) |
| 57 | 0.768465 | -(2.276e-01)Thr+(6.255e-01)Glu-(7.300e-01)Met+(1.551e-01)Trp+(1.378e+01) |
| 58 | 0.768203 | (1.882e-01)Thr+(3.969e-01)Ser-(8.625e-01)Glu+(2.513e-01)Leu-(6.098e+01) |
| 59 | 0.768203 | -(3.728e-01)Ser+(6.935e-01)Glu-(1.040e-01)Val-(6.077e-01)Met+(5.188e+01) |
| 60 | 0.767941 | -(6.100e-01)Asn+(3.950e-01)Glu+(5.733e-01)Ile-(3.785e-01)Leu+(2.265e+01) |
| 61 | 0.767941 | (1.663e-01)Glu-(9.492e-03)Gly-(9.372e-01)Met+(3.063e-01)Tyr+(1.045e+00) |
| 62 | 0.767941 | (1.742e-01)Glu-(5.040e-03)Gly-(8.944e-01)Met+(4.119e-01)Phe-(5.544e+00) |
| 63 | 0.767679 | -(3.366e-01)Thr+(8.606e-01)Glu-(2.331e-01)Leu+(3.028e-01)Trp+(1.777e+01) |
| 64 | 0.767679 | (1.644e-01)Glu-(9.384e-01)Met+(3.037e-01)Tyr+(1.238e-02)His-(2.005e+00) |
| 65 | 0.767679 | -(3.735e-01)Thr+(8.917e-01)Glu+(6.655e-02)Ala-(2.470e-01)Leu+(1.472e+01) |
| 66 | 0.767679 | -(2.322e-01)Thr+(6.802e-01)Glu-(3.755e-02)Gly-(6.943e-01)Met+(2.797e+01) |
| 67 | 0.767679 | -(2.371e-01)Thr+(6.441e-01)Glu-(7.244e-01)Met+(6.429e-02)Ile+(1.790e+01) |
| 68 | 0.767417 | -(2.575e-01)Thr+(7.087e-01)Glu-(6.569e-01)Met+(1.966e+01) |

FIG.34

| RANK | VALUE | FORMULA |
|---|---|---|
| 69 | 0.767156 | (1.705e-01)Thr+(6.747e-01)Asn-(7.124e-01)Glu+(9.057e-02)Val-(4.152e+01) |
| 70 | 0.767156 | -(5.296e-01)Ser+(8.122e-01)Glu+(1.180e-01)Pro-(2.143e-01)Val+(5.739e+01) |
| 71 | 0.767156 | -(3.633e-01)Thr+(8.881e-01)Glu-(2.183e-01)Leu+(1.782e-01)Orn+(2.251e+01) |
| 72 | 0.767156 | (1.680e-01)Glu-(2.864e-02)Cit-(9.351e-01)Met+(3.108e-01)Tyr-(7.639e-01) |
| 73 | 0.767156 | -(4.777e-01)Ser+(8.318e-01)Glu+(1.142e-01)Trp-(2.584e-01)Lys+(6.459e+01) |
| 74 | 0.766894 | -(1.654e-01)Thr-(6.742e-01)Asn+(6.322e-01)Glu-(3.440e-01)Met+(3.405e+01) |
| 75 | 0.766894 | (4.679e-01)Glu-(4.814e-02)Gly+(7.106e-01)Ile-(5.233e-01)Leu+(1.298e+01) |
| 76 | 0.766894 | (1.670e-01)Glu-(9.361e-01)Met+(3.096e-01)Tyr-(4.299e-03)Trp-(1.331e+00) |
| 77 | 0.766894 | (1.666e-01)Glu-(9.366e-01)Met+(3.082e-01)Tyr-(1.419e+00) |
| 78 | 0.766894 | -(3.333e-01)Thr+(9.338e-01)Glu-(1.988e-02)Cit-(1.283e-01)Val+(3.019e+01) |
| 79 | 0.766894 | -(2.568e-01)Thr+(6.432e-01)Glu-(7.151e-01)Met+(9.478e-02)Arg+(1.533e+01) |
| 80 | 0.766894 | -(3.996e-01)Thr+(8.914e-01)Glu+(1.401e-01)Pro-(1.618e-01)Val+(2.843e+01) |
| 81 | 0.766894 | -(3.333e-01)Thr+(6.990e-01)Glu-(2.490e-01)Leu+(5.816e-01)Tyr+(3.867e+00) |
| 82 | 0.76637 | -(3.249e-01)Thr+(8.796e-01)Glu+(2.811e-01)Orn-(2.042e-01)Lys+(2.664e+01) |
| 83 | 0.76637 | -(3.011e-01)Thr+(8.692e-01)Glu-(3.764e-01)ABA-(1.103e-01)Val+(3.259e+01) |
| 84 | 0.76637 | -(2.517e-01)Thr+(6.281e-01)Glu+(6.962e-01)Tyr-(2.395e-01)Lys+(7.439e+00) |
| 85 | 0.76637 | (1.688e-01)Glu-(8.954e-01)Met+(4.119e-01)Phe+(1.245e-02)Orn-(7.262e+00) |
| 86 | 0.76637 | -(3.325e-01)Thr+(9.341e-01)Glu-(1.271e-01)Val-(2.841e-02)Met+(2.993e+01) |
| 87 | 0.76637 | -(4.870e-01)Ser+(8.344e-01)Glu-(1.213e-01)His-(2.277e-01)Lys+(7.490e+01) |
| 88 | 0.76637 | -(4.670e-01)Ser+(8.637e-01)Glu-(1.070e-01)Val-(1.565e-01)Lys+(7.051e+01) |
| 89 | 0.76637 | -(4.741e-01)Ser+(8.490e-01)Glu-(1.733e-01)Leu-(1.560e-01)Lys+(6.907e+01) |
| 90 | 0.76637 | -(4.833e-01)Ser+(8.399e-01)Glu-(2.470e-01)Lys+(6.822e+01) |
| 91 | 0.76637 | (1.706e-01)Glu-(9.342e-01)Met+(3.129e-01)Tyr-(1.712e-02)Orn-(9.467e-01) |
| 92 | 0.76637 | (1.726e-01)Glu-(8.931e-01)Met+(4.153e-01)Phe-(6.941e+00) |
| 93 | 0.76637 | -(2.575e-01)Thr+(7.123e-01)Glu-(3.682e-02)Cit-(6.519e-01)Met+(2.057e+01) |
| 94 | 0.766108 | (9.636e-01)Glu-(8.421e-02)Gly-(2.172e-01)Val+(1.315e-01)Orn+(2.148e+01) |
| 95 | 0.766108 | -(3.431e-01)Thr+(9.176e-01)Glu-(3.804e-02)Cit-(1.972e-01)Leu+(2.811e+01) |
| 96 | 0.766108 | -(8.020e-01)Asn+(5.491e-01)Glu+(1.846e-01)Orn-(1.455e-01)Lys+(3.198e+01) |
| 97 | 0.766108 | -(3.341e-01)Thr+(9.337e-01)Glu-(1.287e-01)Val+(2.974e+01) |
| 98 | 0.766108 | (1.720e-01)Glu-(8.941e-01)Met+(4.134e-01)Phe+(4.856e-03)Trp-(7.018e+00) |
| 99 | 0.766108 | (1.830e-01)Thr+(6.692e-01)Asn-(7.072e-01)Glu+(1.364e-01)Leu-(3.949e+01) |
| 100 | 0.766108 | (9.345e-01)Glu-(6.127e-02)Gly+(1.826e-01)Trp-(2.993e-01)Lys+(2.744e+01) |

FIG.36

| RANK | VALUE | FORMULA |
|---|---|---|
| 1 | 0.95525 | (1.463e-01)Gln-(2.557e-01)Pro-(4.162e-01)Tyr+(8.602e-01)Trp-(6.720e+01) |
| 2 | 0.951807 | (1.848e-01)Gln-(2.946e-01)Pro+(8.953e-01)Trp-(2.784e-01)Arg-(8.666e+01) |
| 3 | 0.944923 | (8.426e-01)Asn-(3.667e-02)Ala-(2.298e-01)Tyr+(4.857e-01)Trp-(3.504e+01) |
| 4 | 0.94148 | (5.453e-01)Asn+(4.330e-01)ABA-(6.573e-01)Met+(2.883e-01)Trp-(3.050e+01) |
| 5 | 0.938038 | (6.515e-01)Asn+(5.998e-01)ABA-(2.935e-01)Tyr+(3.600e-01)Trp-(4.124e+01) |
| 6 | 0.936317 | (2.298e-01)Glu+(5.294e-02)Pro-(8.680e-01)ABA-(4.371e-01)Trp+(2.476e+01) |
| 7 | 0.936317 | -(1.073e-01)Gln+(2.224e-01)Pro-(7.919e-01)ABA-(5.585e-01)Trp+(7.684e+01) |
| 8 | 0.936317 | (1.677e-01)Gln-(2.957e-01)Pro-(3.489e-02)Ala+(9.398e-01)Trp-(9.202e+01) |
| 9 | 0.932874 | (8.436e-01)Asn-(1.089e-01)Pro-(2.430e-01)Tyr+(4.662e-01)Trp-(3.234e+01) |
| 10 | 0.932874 | (8.846e-01)Asn-(4.355e-02)Ala+(4.584e-01)Trp-(7.384e-02)Arg-(4.084e+01) |
| 11 | 0.932874 | (1.716e-01)Gln-(7.442e-02)Ala+(9.372e-01)Trp-(2.946e-01)Arg-(9.068e+01) |
| 12 | 0.932874 | -(2.478e-01)Glu+(8.485e-01)ABA-(1.443e-01)Tyr+(4.448e-01)Trp-(2.170e+01) |
| 13 | 0.932874 | (1.214e-01)Gln-(1.895e-01)Pro-(7.033e-01)Met+(6.743e-01)Trp-(5.951e+01) |
| 14 | 0.932874 | (7.579e-01)Asn-(2.879e-02)Ala-(5.037e-01)Met+(4.135e-01)Trp-(3.141e+01) |
| 15 | 0.929432 | -(2.199e-01)Glu+(1.635e-01)Gln-(2.753e-01)Pro+(9.215e-01)Trp-(9.513e+01) |
| 16 | 0.927711 | (1.737e-01)Gln-(2.993e-01)Pro+(9.334e-01)Trp-(9.531e-02)Lys-(8.801e+01) |
| 17 | 0.927711 | -(6.818e-01)Asn+(1.197e-01)Pro-(6.236e-01)ABA-(3.631e-01)Trp+(4.670e+01) |
| 18 | 0.927711 | -(9.573e-02)Pro+(8.853e-01)ABA-(1.336e-01)Tyr+(4.351e-01)Trp-(1.965e+01) |
| 19 | 0.927711 | (5.858e-02)Gln+(4.769e-01)ABA-(8.064e-01)Met+(3.448e-01)Trp-(3.865e+01) |
| 20 | 0.92599 | -(2.392e-01)Glu+(8.348e-01)ABA-(2.399e-01)Phe+(4.341e-01)Trp-(1.674e+01) |
| 21 | 0.92599 | -(5.397e-02)Ser+(8.954e-01)Asn-(4.596e-02)Ala+(4.397e-01)Trp-(3.999e+01) |
| 22 | 0.92599 | (8.349e-01)Asn-(1.807e-01)Glu-(3.604e-02)Ala+(5.186e-01)Trp-(4.423e+01) |
| 23 | 0.92599 | -(6.732e-01)Asn+(4.443e-02)Ala-(6.233e-01)ABA-(3.954e-01)Trp+(4.762e+01) |
| 24 | 0.92599 | -(1.694e-01)Ser+(1.963e-01)Gln-(3.436e-01)Pro+(9.026e-01)Trp-(9.278e+01) |
| 25 | 0.924269 | (8.178e-01)ABA-(3.103e-01)Tyr+(3.772e-01)His+(3.043e-01)Trp-(4.282e+01) |
| 26 | 0.924269 | (9.843e-02)Gln-(3.492e-02)Ala-(7.846e-01)Met+(6.111e-01)Trp-(5.278e+01) |
| 27 | 0.922547 | -(1.915e-01)Glu+(7.930e-02)Gln-(8.278e-01)Met+(5.213e-01)Trp-(4.156e+01) |
| 28 | 0.922547 | -(2.722e-02)Thr+(1.805e-01)Gln-(3.384e-01)Pro+(9.231e-01)Trp-(1.016e+02) |
| 29 | 0.922547 | -(2.264e-01)Glu+(8.591e-01)ABA-(1.036e-01)Ile+(4.471e-01)Trp-(2.581e+01) |
| 30 | 0.922547 | (1.690e-01)Gln-(3.101e-01)Pro-(2.183e-01)Phe+(9.093e-01)Trp-(8.902e+01) |
| 31 | 0.920826 | -(4.105e-01)Glu+(1.529e-01)Gln+(8.356e-01)Trp-(3.316e-01)Arg-(8.248e+01) |
| 32 | 0.920826 | (8.715e-01)Asn-(1.051e-01)Pro-(2.916e-02)Ala+(4.781e-01)Trp-(3.979e+01) |
| 33 | 0.920826 | (8.200e-02)Gln+(7.773e-01)ABA-(3.860e-01)Tyr+(4.900e-01)Trp-(6.229e+01) |
| 34 | 0.920826 | (1.580e-01)Gln-(4.558e-02)Gly-(5.488e-01)Tyr+(8.196e-01)Trp-(8.292e+01) |

FIG.37

| RANK | VALUE | FORMULA |
|---|---|---|
| 35 | 0.920826 | (1.797e-01)Gln-(3.121e-01)Pro+(9.061e-01)Trp-(2.220e-01)Orn-(9.408e+01) |
| 36 | 0.919105 | (8.811e-01)Asn-(4.658e-02)Ala+(5.771e-02)Cit+(4.671e-01)Trp-(4.842e+01) |
| 37 | 0.919105 | -(3.673e-03)Thr+(8.850e-01)Asn-(4.687e-02)Ala+(4.631e-01)Trp-(4.605e+01) |
| 38 | 0.919105 | (1.383e-01)Gln-(5.980e-02)Ala-(4.079e-01)Tyr+(9.005e-01)Trp-(7.615e+01) |
| 39 | 0.919105 | (8.458e-01)ABA-(2.120e-01)Ile-(1.512e-01)Tyr+(4.656e-01)Trp-(1.900e+01) |
| 40 | 0.917384 | (8.842e-01)Asn-(4.703e-02)Ala+(4.647e-01)Trp-(1.045e-02)Orn-(4.587e+01) |
| 41 | 0.917384 | (1.602e-01)Gln-(7.917e-02)Ala+(9.246e-01)Trp-(3.365e-01)Orn-(8.900e+01) |
| 42 | 0.917384 | (8.052e-01)Asn-(1.881e-01)Glu-(2.634e-01)Tyr+(4.969e-01)Trp-(3.745e+01) |
| 43 | 0.917384 | -(7.875e-02)Ser+(7.177e-01)Asn+(6.758e-01)ABA-(1.484e-01)Tyr-(2.860e+01) |
| 44 | 0.915663 | (8.240e-01)Asn-(4.062e-02)Ala-(2.975e-01)Phe+(4.804e-01)Trp-(3.023e+01) |
| 45 | 0.915663 | -(9.343e-02)Pro+(8.938e-01)ABA-(1.345e-01)Phe+(4.176e-01)Trp-(1.998e+01) |
| 46 | 0.915663 | (7.080e-01)Asn+(7.977e-02)Gln-(7.224e-02)Ala+(6.980e-01)Trp-(8.619e+01) |
| 47 | 0.915663 | -(8.656e-02)Gln+(5.635e-02)Ala-(8.337e-01)ABA-(5.425e-01)Trp+(7.346e+01) |
| 48 | 0.915663 | -(8.845e-01)Asn+(4.702e-02)Ala+(3.772e-03)His-(4.642e-01)Trp+(4.616e+01) |
| 49 | 0.915663 | (8.652e-01)Asn-(1.150e-02)Gly-(2.857e-01)Tyr+(4.119e-01)Trp-(3.829e+01) |
| 50 | 0.915663 | (8.872e-01)Asn-(4.406e-03)Gly-(4.620e-02)Ala+(4.591e-01)Trp-(4.549e+01) |
| 51 | 0.915663 | (5.500e-01)Asn+(1.250e-01)Gln-(2.915e-01)Pro+(7.726e-01)Trp-(9.679e+01) |
| 52 | 0.915663 | (1.789e-01)Gln-(3.443e-01)Pro+(1.852e-02)Cit+(9.215e-01)Trp-(1.037e+02) |
| 53 | 0.913941 | -(2.260e-02)Ala+(8.560e-01)ABA-(2.009e-01)Ile+(4.758e-01)Trp-(2.207e+01) |
| 54 | 0.913941 | -(8.846e-01)Asn+(4.722e-02)Ala-(4.640e-01)Trp-(4.000e-04)Lys+(4.646e+01) |
| 55 | 0.913941 | -(1.793e-01)Gln+(3.427e-01)Pro+(1.214e-02)His-(9.221e-01)Trp+(1.026e+02) |
| 56 | 0.913941 | (1.796e-01)Gln-(3.442e-01)Pro+(9.216e-01)Trp-(1.035e+02) |
| 57 | 0.913941 | (1.915e-01)Gln-(3.514e-01)Pro-(4.505e-02)Gly+(9.153e-01)Trp-(9.759e+01) |
| 58 | 0.913941 | (8.845e-01)Asn-(4.718e-02)Ala+(4.642e-01)Trp-(4.640e+01) |
| 59 | 0.91222 | -(4.270e-02)Ser+(8.728e-01)Asn-(2.747e-01)Tyr+(4.013e-01)Trp-(3.685e+01) |
| 60 | 0.91222 | -(5.747e-01)Asn+(2.138e-01)Glu-(6.973e-01)ABA-(3.713e-01)Trp+(5.086e+01) |
| 61 | 0.91222 | (9.024e-02)Pro+(1.800e-02)Ala-(8.936e-01)ABA-(4.394e-01)Trp+(2.289e+01) |
| 62 | 0.91222 | (1.739e-01)Gln-(3.207e-01)Pro-(2.572e-02)Val+(9.307e-01)Trp-(9.826e+01) |
| 63 | 0.91222 | (1.745e-01)Gln-(3.723e-01)Tyr+(8.778e-01)Trp-(2.458e-01)Arg-(9.563e+01) |
| 64 | 0.910499 | (7.151e-01)Asn-(7.896e-03)Gly+(6.807e-01)ABA-(1.587e-01)Tyr-(3.493e+01) |
| 65 | 0.910499 | -(3.667e-01)Glu+(1.370e-01)Gln-(5.310e-02)Ala+(9.187e-01)Trp-(9.065e+01) |
| 66 | 0.910499 | (1.732e-01)Gln-(3.112e-01)Pro-(5.715e-02)Leu+(9.327e-01)Trp-(9.801e+01) |
| 67 | 0.910499 | -(6.659e-02)Pro+(8.788e-01)ABA-(1.536e-01)Ile+(4.468e-01)Trp-(2.321e+01) |
| 68 | 0.908778 | -(1.206e-01)Thr+(1.314e-01)Pro-(9.051e-01)ABA-(3.859e-01)Trp+(3.562e+01) |

FIG.38

| RANK | VALUE | FORMULA |
|---|---|---|
| 69 | 0.908778 | $-(1.561e-01)$Ser$+(1.648e-01)$Gln$-(5.256e-01)$Tyr$+(8.199e-01)$Trp$-(8.195e+01)$ |
| 70 | 0.908778 | $-(3.388e-01)$Glu$+(1.236e-01)$Gln$-(4.220e-01)$Tyr$+(8.318e-01)$Trp$-(7.178e+01)$ |
| 71 | 0.908778 | $-(1.939e-01)$Ser$+(1.830e-01)$Gln$-(9.086e-02)$Ala$+(9.595e-01)$Trp$-(9.656e+01)$ |
| 72 | 0.908778 | $(3.776e-01)$Asn$+(4.268e-02)$Gln$-(8.544e-01)$Met$+(3.543e-01)$Trp$-(3.592e+01)$ |
| 73 | 0.908778 | $-(2.668e-01)$Glu$+(1.034e-01)$Gln$+(9.465e-01)$ABA$-(1.495e-01)$Arg$-(5.585e+01)$ |
| 74 | 0.908778 | $-(2.787e-02)$Ala$+(8.885e-01)$ABA$-(1.280e-01)$Tyr$+(4.399e-01)$Trp$-(2.262e+01)$ |
| 75 | 0.908778 | $-(1.055e-01)$Pro$+(9.076e-01)$ABA$+(4.064e-01)$Trp$-(2.569e+01)$ |
| 76 | 0.908778 | $(8.576e-01)$Asn$-(1.438e-01)$Glu$-(1.048e-01)$Pro$+(4.825e-01)$Trp$-(4.406e+01)$ |
| 77 | 0.908778 | $(1.144e-01)$Gln$+(2.912e-01)$Val$-(9.361e-01)$Ile$-(1.607e-01)$Arg$-(5.840e+01)$ |
| 78 | 0.907057 | $(2.529e-02)$Ser$+(2.668e-01)$Glu$-(8.744e-01)$ABA$-(4.044e-01)$Trp$+(2.554e+01)$ |
| 79 | 0.907057 | $(1.980e-01)$Gln$+(8.604e-01)$Trp$-(3.387e-01)$Orn$-(3.252e-01)$Arg$-(1.045e+02)$ |
| 80 | 0.907057 | $-(2.901e-02)$Ala$+(8.724e-01)$ABA$-(2.192e-01)$Phe$+(4.360e-01)$Trp$-(1.742e+01)$ |
| 81 | 0.907057 | $(4.055e-01)$Ser$+(6.981e-01)$Glu$-(3.412e-01)$Gln$+(4.814e-01)$Arg$+(7.971e+01)$ |
| 82 | 0.907057 | $(7.072e-01)$Asn$+(6.357e-01)$ABA$+(3.046e-01)$Trp$-(5.570e-02)$Arg$-(5.478e+01)$ |
| 83 | 0.907057 | $(2.473e-01)$Glu$+(1.599e-02)$Ala$-(8.604e-01)$ABA$-(4.453e-01)$Trp$+(2.550e+01)$ |
| 84 | 0.907057 | $-(6.495e-01)$Asn$+(1.550e-01)$Glu$-(7.355e-01)$ABA$+(1.144e-01)$Tyr$+(3.251e+01)$ |
| 85 | 0.907057 | $(8.285e-01)$Asn$-(3.580e-02)$Ala$-(2.049e-01)$Ile$+(5.199e-01)$Trp$-(3.898e+01)$ |
| 86 | 0.905336 | $-(2.005e-01)$Ser$+(2.251e-01)$Gln$+(8.764e-01)$Trp$-(3.756e-01)$Arg$-(1.124e+02)$ |
| 87 | 0.905336 | $(1.369e-01)$Gln$-(6.960e-02)$Ala$-(4.220e-01)$Phe$+(8.935e-01)$Trp$-(7.330e+01)$ |
| 88 | 0.905336 | $-(1.925e-02)$Ser$+(1.082e-01)$Pro$-(9.036e-01)$ABA$-(4.141e-01)$Trp$+(2.784e+01)$ |
| 89 | 0.905336 | $-(2.668e-01)$Glu$+(8.717e-01)$ABA$+(4.109e-01)$Trp$+(4.089e-03)$Arg$-(2.904e+01)$ |
| 90 | 0.905336 | $(6.840e-01)$Asn$-(1.428e-01)$Glu$-(5.916e-01)$Met$+(4.023e-01)$Trp$-(2.986e+01)$ |
| 91 | 0.905336 | $(8.110e-01)$Asn$-(9.276e-02)$Pro$-(4.050e-01)$Met$+(4.119e-01)$Trp$-(3.458e+01)$ |
| 92 | 0.905336 | $(8.605e-01)$Asn$-(4.390e-02)$Ala$-(3.274e-02)$Val$+(5.064e-01)$Trp$-(4.170e+01)$ |
| 93 | 0.905336 | $-(1.010e-01)$Pro$+(9.052e-01)$ABA$-(1.087e-02)$Leu$+(4.126e-01)$Trp$-(2.526e+01)$ |
| 94 | 0.905336 | $-(6.347e-01)$ABA$+(6.539e-01)$Ile$-(2.889e-01)$Leu$-(2.936e-01)$Trp$+(2.331e+01)$ |
| 95 | 0.905336 | $-(2.674e-01)$Glu$+(8.708e-01)$ABA$+(4.126e-01)$Trp$-(2.872e+01)$ |
| 96 | 0.905336 | $-(2.675e-01)$Glu$+(8.708e-01)$ABA$+(8.118e-05)$Val$+(4.125e-01)$Trp$-(2.873e+01)$ |
| 97 | 0.905336 | $(7.217e-01)$Asn$-(8.424e-02)$Pro$+(6.780e-01)$ABA$-(1.107e-01)$Tyr$-(2.998e+01)$ |
| 98 | 0.905336 | $(4.602e-01)$Glu$+(1.054e-01)$Pro$-(7.263e-01)$Trp$-(4.996e-01)$Orn$+(3.429e+01)$ |
| 99 | 0.905336 | $-(2.671e-01)$Glu$+(8.706e-01)$ABA$-(4.767e-03)$Met$+(4.131e-01)$Trp$-(2.862e+01)$ |
| 100 | 0.903614 | $(1.490e-01)$Gln$-(4.584e-01)$Ile$+(8.427e-01)$Trp$-(2.400e-01)$Arg$-(7.747e+01)$ |

FIG.40

| RANK | VALUE | FORMULA |
|---|---|---|
| 1 | 0.805096 | (Pro+AAA)/(Ser)+(Glu+Tyr+Phe+Orn)/(Met) |
| 2 | 0.803275 | (Glu+Phe)/(Met)+(Tyr+Orn)/(Ser) |
| 3 | 0.802404 | (Phe)/(Met+Asn)+(Glu+Orn)/(Lys+Ser) |
| 4 | 0.802329 | (Phe)/(Met)+(Glu+Pro+Orn+Trp)/(His+Ser) |
| 5 | 0.801969 | (Pro+AAA)/(Asn+Ser)+(Glu+Tyr+Phe)/(Met) |
| 6 | 0.801761 | (Glu+Tyr+Phe)/(Met)+(Pro+Orn+Trp)/(Ser) |
| 7 | 0.801322 | (Phe)/(Met)+(Glu+Pro+Tyr+Orn)/(His+Ser) |
| 8 | 0.801062 | (Glu+Tyr+Phe)/(Met)+(Ile+Orn+Trp)/(Ser) |
| 9 | 0.800852 | (Phe)/(Met+Asn)+(Glu+Tyr+Orn)/(Lys+Ser) |
| 10 | 0.800773 | (Glu+Phe)/(Met)+(Tyr+Orn+Trp)/(Asn+Ser) |
| 11 | 0.800494 | (Tyr+AAA)/(Cit+Ser)+(Glu+Phe+Orn)/(Met) |
| 12 | 0.800352 | (Glu+Phe)/(Met)+(Tyr+Orn)/(Asn+Ser) |
| 13 | 0.800152 | (Phe)/(Met+Asn)+(Glu+Orn)/(ABA+Lys) |
| 14 | 0.800045 | (Tyr+AAA)/(Asn+Ser)+(Glu+Phe+Orn)/(Met) |
| 15 | 0.79989 | (Phe)/(ABA+Asn+Ser)+(Glu+Orn)/(Met+Lys) |
| 16 | 0.799627 | (Glu+Phe)/(Met)+(Tyr+Orn+Trp)/(ABA+Ser) |
| 17 | 0.799567 | (Glu+Phe)/(Met)+(AAA+Orn+Trp)/(His+Ser) |
| 18 | 0.799391 | (Tyr+AAA)/(ABA+Ser)+(Glu+Phe+Orn)/(Met) |
| 19 | 0.799358 | (Glu+Phe)/(Met)+(AAA+Orn)/(ABA+Asn+Ser) |
| 20 | 0.799275 | (Glu+Phe)/(Met)+(AAA+Orn)/(Asn+Ser) |
| 21 | 0.799261 | (Pro+AAA)/(Cit+Ser)+(Glu+Phe+Orn)/(Met) |
| 22 | 0.799235 | (Glu+Phe)/(Met)+(Tyr+Orn)/(ABA+Ser) |
| 23 | 0.79898 | (Glu+Phe)/(Met)+(Tyr+AAA+Orn)/(His+Ser) |
| 24 | 0.798808 | (Pro+Orn)/(ABA+Ser)+(Glu+Tyr+Phe)/(Met) |
| 25 | 0.798717 | (Phe)/(ABA+Met+Asn+Ser)+(Glu+Orn)/(Lys) |
| 26 | 0.798713 | (Phe)/(Met)+(Glu+Pro+Tyr+Trp)/(His+Ser) |
| 27 | 0.798709 | (Phe)/(Met+Asn)+(Glu+Orn)/(ABA+Lys+Ser) |
| 28 | 0.798668 | (Glu+Phe)/(Met)+(AAA+Orn)/(His+Ser) |
| 29 | 0.798545 | (Phe)/(Met)+(Glu+Pro+Orn)/(His+Ser) |
| 30 | 0.798505 | (Pro+Orn)/(Ser)+(Glu+Tyr+Phe)/(Met) |
| 31 | 0.798237 | (Ile+Orn)/(Ser)+(Glu+Tyr+Phe)/(Met) |
| 32 | 0.798122 | (Pro+AAA)/(His+Ser)+(Glu+Tyr+Phe)/(Met) |
| 33 | 0.798107 | (Glu+Phe)/(Met)+(Tyr+Orn+Trp)/(Ser) |
| 34 | 0.79805 | (Pro+AAA)/(Asn+Ser)+(Glu+Phe+Orn)/(Met) |

FIG.41

| RANK | VALUE | FORMULA |
|---|---|---|
| 35 | 0.797966 | (Phe)/(Met+Asn)+(Glu+Orn)/(Lys) |
| 36 | 0.797873 | (Phe)/(Met+Asn+Ser)+(Glu+Orn)/(Cit+Lys) |
| 37 | 0.797833 | (Glu+Phe)/(Met)+(Tyr+AAA+Orn)/(Thr+Ser) |
| 38 | 0.797822 | (Phe)/(ABA+Asn+Ser)+(Glu+Orn)/(Cit+Lys) |
| 39 | 0.797776 | (Phe)/(Met+Asn)+(Glu+Orn)/(Cit+Lys+Ser) |
| 40 | 0.797751 | (Phe)/(Met)+(Glu+Pro+Tyr)/(His+Ser) |
| 41 | 0.797745 | (AAA+Orn)/(ABA+Ser)+(Glu+Tyr+Phe)/(Met) |
| 42 | 0.797732 | (Ala+Orn)/(Lys+Ser)+(Glu+Tyr+Phe)/(Met) |
| 43 | 0.797711 | (Glu+Phe)/(Met)+(Pro+AAA+Orn)/(His+Ser) |
| 44 | 0.797559 | (Glu+Phe)/(Met)+(Orn+Trp)/(Ser) |
| 45 | 0.797517 | (Tyr+AAA)/(Ser)+(Glu+Phe+Orn)/(Met) |
| 46 | 0.797476 | (Phe)/(Met+Asn+Ser)+(Glu+Orn)/(Lys) |
| 47 | 0.797473 | (Pro+Trp)/(Asn+Ser)+(Glu+Tyr+Phe)/(Met) |
| 48 | 0.797471 | (Phe)/(Cit+Asn+Ser)+(Glu+Orn)/(Met+Lys) |
| 49 | 0.797436 | (Glu+Phe)/(Met)+(Tyr+Orn)/(Arg+Ser) |
| 50 | 0.797354 | (Phe)/(Met)+(Glu+Pro+Tyr)/(His+Cit+Ser) |
| 51 | 0.797295 | (Glu+Phe)/(Met)+(Pro+Tyr+Orn)/(Asn+Ser) |
| 52 | 0.797289 | (Phe)/(Met)+(Glu+Pro+AAA)/(His+Cit+Ser) |
| 53 | 0.797232 | (Pro+AAA)/(Arg+Ser)+(Glu+Tyr+Phe)/(Met) |
| 54 | 0.797214 | (Phe)/(Thr+Ser)+(Glu+Orn)/(Met+Lys+Asn) |
| 55 | 0.797153 | (Phe)/(Met)+(Glu+Pro+Orn)/(His+Cit+Ser) |
| 56 | 0.797113 | (Glu+Phe)/(Met)+(Tyr+Orn)/(Cit+Ser) |
| 57 | 0.797112 | (Glu+Phe)/(Met)+(Pro+AAA+Orn)/(Lys+Ser) |
| 58 | 0.797096 | (AAA+Orn)/(Asn+Ser)+(Glu+Tyr+Phe)/(Met) |
| 59 | 0.797091 | (Tyr+Phe)/(Met)+(Glu+Pro+AAA)/(His+Ser) |
| 60 | 0.797083 | (Phe)/(ABA+Met+Asn)+(Glu+Orn)/(Lys) |
| 61 | 0.797038 | (Glu+Phe)/(Met)+(Pro+AAA)/(ABA+Arg+Ser) |
| 62 | 0.796988 | (Glu+Phe)/(Met)+(Tyr+Orn)/(Cit+ABA+Ser) |
| 63 | 0.796984 | (Glu+Phe)/(Met)+(Tyr+Orn)/(Thr+Ser) |
| 64 | 0.796931 | (Glu+Phe)/(Met)+(Tyr+Ile+Orn)/(Arg+Ser) |
| 65 | 0.796924 | (Glu+Phe)/(Met)+(Pro+AAA+Orn)/(Thr+Ser) |
| 66 | 0.796856 | (Glu+Phe)/(Met)+(Pro+AAA)/(Lys+Ser) |
| 67 | 0.796783 | (Glu+Phe)/(Met)+(Pro+Tyr+Orn)/(His+Ser) |
| 68 | 0.796778 | (Glu+Phe)/(Met)+(AAA+Orn+Trp)/(Asn+Ser) |

FIG.42

| RANK | VALUE | FORMULA |
| --- | --- | --- |
| 69 | 0.796771 | (AAA)/(Ser)+(Glu+Phe+Orn)/(Met) |
| 70 | 0.796711 | (Phe)/(Met)+(Glu+Pro+AAA)/(His+Asn+Ser) |
| 71 | 0.796697 | (Glu+Phe)/(Met)+(AAA+Ile+Orn)/(His+Ser) |
| 72 | 0.796697 | (Glu+Phe)/(Met)+(Tyr+AAA+Orn)/(Asn+Ser) |
| 73 | 0.796674 | (AAA+Ile)/(Ser)+(Glu+Tyr+Phe+Orn)/(Met) |
| 74 | 0.79665 | (Glu+Phe)/(Met)+(Ala+Orn)/(Gly+Asn+Ser) |
| 75 | 0.796593 | (Phe)/(Cit+Thr+Ser)+(Glu+Orn)/(Met+Lys) |
| 76 | 0.796591 | (Glu+Phe)/(Met)+(Pro+Tyr+AAA)/(Lys+Ser) |
| 77 | 0.796589 | (Phe)/(Thr+Ser)+(Glu+Orn)/(ABA+Met+Lys) |
| 78 | 0.796588 | (Glu)/(Asn+Ser)+(Phe+Orn)/(Cit+Met+Lys) |
| 79 | 0.796573 | (Glu+Phe)/(Met)+(Tyr+Orn+Trp)/(His+Ser) |
| 80 | 0.796564 | (Glu+Phe)/(Met)+(Tyr+Orn+Trp)/(Thr+Ser) |
| 81 | 0.796536 | (Glu+Phe)/(Met)+(Tyr+Orn)/(His+Ser) |
| 82 | 0.796528 | (Glu+Phe)/(Met)+(Tyr+Orn+Trp)/(Arg+Ser) |
| 83 | 0.796526 | (Glu+Phe)/(Met)+(Pro+Tyr+Trp)/(Arg+Ser) |
| 84 | 0.7965 | (Pro+Orn)/(Asn+Ser)+(Glu+Tyr+Phe)/(Met) |
| 85 | 0.796498 | (Glu+Phe)/(Met)+(AAA+Orn)/(His+Asn+Ser) |
| 86 | 0.796489 | (Phe)/(Met+Asn)+(Glu+Orn)/(Cit+Lys) |
| 87 | 0.796483 | (Glu+Phe)/(Met)+(Tyr+AAA+Orn)/(Lys+Ser) |
| 88 | 0.796472 | (Pro+Trp)/(ABA+Ser)+(Glu+Tyr+Phe)/(Met) |
| 89 | 0.796457 | (Phe)/(Met+Asn)+(Glu+Orn+Trp)/(Lys+Ser) |
| 90 | 0.796454 | (Glu+Phe)/(Met)+(Pro+Tyr+Trp)/(Asn+Ser) |
| 91 | 0.79645 | (Glu+Phe)/(Met)+(Pro+AAA)/(Arg+Ser) |
| 92 | 0.796424 | (Pro+Ile)/(Asn+Ser)+(Glu+Tyr+Phe)/(Met) |
| 93 | 0.796338 | (Ala+Orn)/(His+Ser)+(Glu+Tyr+Phe)/(Met) |
| 94 | 0.796267 | (Glu+Phe)/(Met)+(AAA+Ile+Orn)/(Thr+Ser) |
| 95 | 0.796266 | (Glu+Phe)/(Met)+(Pro+AAA)/(His+ABA+Ser) |
| 96 | 0.796265 | (Glu+Phe)/(Met)+(AAA+Orn)/(His+ABA+Ser) |
| 97 | 0.79621 | (Glu+Phe)/(Met)+(Tyr+AAA)/(ABA+Asn+Ser) |
| 98 | 0.796209 | (Glu+Phe)/(Met)+(Pro+Tyr)/(Arg+Thr+Ser) |
| 99 | 0.796207 | (Glu+Phe)/(Met)+(Pro+Tyr+Orn)/(Arg+Ser) |
| 100 | 0.796203 | (Ile+Trp)/(Ser)+(Glu+Tyr+Phe)/(Met) |

FIG.44

| RANK | VALUE | FORMULA |
|---|---|---|
| 1 | 0.905185 | (Gly)/(Arg+Lys)+(Glu+Pro+Ile)/(Trp+ABA) |
| 2 | 0.902133 | (Glu+Ile)/(Trp+ABA)+(Pro+Gly)/(Asn+Gln) |
| 3 | 0.901957 | (Ile)/(ABA)+(Glu+Pro)/(Trp) |
| 4 | 0.901679 | (Glu+Ile)/(Trp+ABA)+(Pro+Gly)/(Gln) |
| 5 | 0.901322 | (Gly)/(Ala+BCAA)+(Glu+Pro)/(Orn+Trp+ABA) |
| 6 | 0.901229 | (Glu+Pro)/(Orn+Trp+ABA)+(Ile+Gly)/(Gln) |
| 7 | 0.900709 | (Gly)/(Orn+Thr)+(Glu+Pro+Ile)/(Trp+ABA) |
| 8 | 0.900104 | (Glu+Ile)/(Trp+ABA)+(Pro+Gly)/(Met+Gln) |
| 9 | 0.9001 | (Gly)/(Arg+Orn+Thr)+(Glu+Pro)/(Trp+ABA) |
| 10 | 0.900053 | (Glu+Ile)/(Trp+ABA)+(Pro+Gly)/(Thr+Gln) |
| 11 | 0.899577 | (Ile)/(Orn+ABA)+(Glu+Pro)/(Leu+Trp) |
| 12 | 0.899307 | (Pro)/(Trp)+(Ile)/(ABA) |
| 13 | 0.898773 | (Pro)/(Trp)+(Glu+Ile)/(ABA) |
| 14 | 0.898732 | (Gly)/(Arg+Orn+Lys)+(Glu+Pro)/(Trp+ABA) |
| 15 | 0.898567 | (Gly)/(Trp+ABA)+(Glu+Pro)/(Asn) |
| 16 | 0.898366 | (Glu+Ile)/(Trp+ABA)+(Pro+Gly)/(Orn+Gln) |
| 17 | 0.898193 | (Ile)/(Orn)+(Glu+Pro)/(Trp+ABA) |
| 18 | 0.897653 | (Glu+Ile)/(ABA)+(Pro+Gly)/(Trp) |
| 19 | 0.897642 | (Gly)/(Arg+Thr)+(Glu+Pro+Ile)/(Trp+ABA) |
| 20 | 0.897161 | (Glu+Pro)/(Trp+ABA)+(Ile+Gly)/(Orn+Thr) |
| 21 | 0.896994 | (Gly)/(Ala+LNAA)+(Glu+Pro)/(Orn+Trp+ABA) |
| 22 | 0.896846 | (Glu+Pro)/(ABA)+(Ile+Gly)/(Trp) |
| 23 | 0.896311 | (Glu+Pro)/(Asn)+(Ile+Gly)/(Trp+ABA) |
| 24 | 0.896041 | (Gly)/(Lys+Thr)+(Glu+Pro+Ile)/(Trp+ABA) |
| 25 | 0.895839 | (Gly)/(AAA+Gln)+(Glu+Pro)/(Orn+Trp+ABA) |
| 26 | 0.895779 | (Glu+Ile)/(Trp)+(Pro+Gly)/(Orn+ABA+Asn) |
| 27 | 0.895746 | (Gly)/(Val+Gln)+(Glu+Pro)/(Orn+Trp+ABA) |
| 28 | 0.895742 | (Gly)/(Orn+Lys)+(Glu+Pro+Ile)/(Trp+ABA) |
| 29 | 0.89557 | (Gly)/(Asn+Gln)+(Glu+Pro)/(Orn+Trp+ABA) |
| 30 | 0.89542 | (Gly)/(Leu+Gln)+(Glu+Pro)/(Orn+Trp+ABA) |
| 31 | 0.895413 | (Glu+Pro)/(Trp+ABA)+(Ile+Gly)/(Lys+Thr) |
| 32 | 0.895083 | (Gly)/(Arg+Cit+Lys)+(Glu+Pro)/(Trp+ABA) |
| 33 | 0.895009 | (Glu+Gly)/(Trp+ABA)+(Pro+Ile)/(Asn) |
| 34 | 0.894747 | (Glu+Ile)/(Trp+ABA)+(Pro+Gly)/(Cit+Gln) |

FIG.45

| RANK | VALUE | FORMULA |
|---|---|---|
| 35 | 0.894617 | (Gly)/(Orn+Lys+Thr)+(Glu+Pro)/(Trp+ABA) |
| 36 | 0.894513 | (Glu+Ile)/(Orn)+(Pro+Gly)/(Trp+ABA+Asn) |
| 37 | 0.894456 | (Gly)/(Ala+Arg+Orn)+(Glu+Pro)/(Trp+ABA) |
| 38 | 0.894001 | (Gly)/(Trp+ABA)+(Pro+Ile)/(Asn) |
| 39 | 0.89387 | (Gly)/(Arg+Gln)+(Glu+Pro)/(Trp+ABA+Asn) |
| 40 | 0.893744 | (Gly)/(Gln)+(Glu+Pro)/(Orn+Trp+ABA) |
| 41 | 0.89374 | (Gly)/(Orn+Thr+Asn)+(Glu+Pro)/(Trp+ABA) |
| 42 | 0.893703 | (Gly)/(Ala+Arg)+(Glu+Pro+Ile)/(Trp+ABA) |
| 43 | 0.893656 | (Gly)/(Lys+Asn)+(Glu+Pro+Ile)/(Trp+ABA) |
| 44 | 0.89363 | (Glu+Ile)/(Trp+ABA)+(Pro+Gly)/(Lys+Gln) |
| 45 | 0.893581 | (Gly)/(Met+Gln)+(Glu+Pro)/(Orn+Trp+ABA) |
| 46 | 0.893493 | (Glu+Ile)/(Trp+ABA)+(Pro+Gly)/(Arg+Gln) |
| 47 | 0.893474 | (Glu)/(Trp)+(Pro+Ile)/(Orn+ABA) |
| 48 | 0.893362 | (Gly)/(Cit+Lys+Thr)+(Glu+Pro)/(Trp+ABA) |
| 49 | 0.89328 | (Glu+Ile)/(Asn)+(Pro+Gly)/(Trp+ABA) |
| 50 | 0.893199 | (Gly)/(BCAA+LNAA)+(Glu+Pro)/(Orn+Trp+ABA) |
| 51 | 0.893058 | (Gly)/(Arg+Lys)+(Glu+Pro)/(Trp+ABA) |
| 52 | 0.892951 | (Gly)/(Ala)+(Glu+Pro+Ile)/(Orn+ABA+Asn) |
| 53 | 0.892946 | (Gly)/(BCAA+Gln)+(Glu+Pro)/(Orn+Trp+ABA) |
| 54 | 0.892914 | (Glu+Pro)/(Trp+ABA)+(Ile+Gly)/(Arg+Lys) |
| 55 | 0.892912 | (Gly)/(Cit+Lys)+(Glu+Pro+Ile)/(Trp+ABA) |
| 56 | 0.892911 | (Gly)/(Ala+Trp)+(Glu+Pro)/(Orn+ABA) |
| 57 | 0.892736 | (Gly)/(Arg+Lys+Asn)+(Glu+Pro)/(Trp+ABA) |
| 58 | 0.892644 | (Gly)/(Gln)+(Glu+Pro+Ile)/(Trp+ABA) |
| 59 | 0.892631 | (Glu+Gly)/(Gln)+(Pro+Ile)/(Trp+ABA) |
| 60 | 0.892631 | (Glu+Gly)/(Cit+Gln)+(Pro+Ile)/(Trp+ABA) |
| 61 | 0.892596 | (Gly)/(BCAA+ABA)+(Glu+Pro+Ile)/(Trp+Thr) |
| 62 | 0.892479 | (Gly)/(His+Gln)+(Glu+Pro)/(Orn+Trp+ABA) |
| 63 | 0.892465 | (Gly)/(Ala+Gln)+(Glu+Pro)/(Orn+Trp+ABA) |
| 64 | 0.892403 | (Gly)/(Thr+Gln)+(Glu+Pro)/(Orn+Trp+ABA) |
| 65 | 0.892386 | (Gly)/(Arg+Gln)+(Glu+Pro+Ile)/(Trp+ABA) |
| 66 | 0.892189 | (Gly)/(Ala+Arg+Met)+(Glu+Pro)/(Trp+ABA) |
| 67 | 0.892057 | (Gly)/(Met+Lys+Thr)+(Glu+Pro)/(Trp+ABA) |
| 68 | 0.892052 | (Gly)/(Ala+Arg+Cit)+(Glu+Pro)/(Trp+ABA) |

FIG.46

| RANK | VALUE | FORMULA |
| --- | --- | --- |
| 69 | 0.892013 | (Gly)/(Arg+Thr+Asn)+(Glu+Pro)/(Trp+ABA) |
| 70 | 0.891996 | (Glu+Ile)/(Trp+ABA)+(Pro+Gly)/(Tyr+Gln) |
| 71 | 0.891841 | (Glu+Ile)/(Trp+ABA)+(Pro+Gly)/(His+Gln) |
| 72 | 0.891809 | (Gly)/(LNAA)+(Glu+Pro+Ile)/(Orn+Trp+ABA) |
| 73 | 0.891777 | (Ile)/(Arg)+(Glu+Pro)/(Trp+ABA) |
| 74 | 0.891655 | (Glu+Ile)/(Trp+ABA)+(Pro+Gly)/(Leu+Gln) |
| 75 | 0.891572 | (Glu+Pro)/(Orn+ABA)+(Ile+Gly)/(Ala+Trp) |
| 76 | 0.891569 | (Glu+Ile)/(Orn+Trp)+(Pro+Gly)/(LNAA+Gln) |
| 77 | 0.891564 | (Gly)/(Cit+Gln)+(Glu+Pro)/(Orn+Trp+ABA) |
| 78 | 0.891471 | (Gly)/(Arg+Lys+Thr)+(Glu+Pro)/(Trp+ABA) |
| 79 | 0.891408 | (Pro)/(ABA)+(Glu+Ile+Gly)/(Trp+Asn) |
| 80 | 0.891404 | (Gly)/(Met+Gln)+(Glu+Pro+Ile)/(Trp+ABA) |
| 81 | 0.891288 | (Glu+Pro)/(Trp+ABA)+(Ile+Gly)/(Ala+Arg) |
| 82 | 0.891274 | (Glu+Gly)/(Met+Gln)+(Pro+Ile)/(Trp+ABA) |
| 83 | 0.891219 | (Gly)/(Ala+Orn)+(Glu+Pro+Ile)/(Trp+ABA) |
| 84 | 0.891207 | (Glu)/(Trp)+(Pro+Ile+Gly)/(Thr+ABA+Asn) |
| 85 | 0.891182 | (Gly)/(Tyr+Orn+Lys)+(Glu+Pro)/(Trp+ABA) |
| 86 | 0.890979 | (Gly)/(Trp+ABA)+(Glu+Pro+Ile)/(Asn) |
| 87 | 0.890964 | (Gly)/(Thr+Asn)+(Glu+Pro+Ile)/(Trp+ABA) |
| 88 | 0.890942 | (Gly)/(Lys+Gln)+(Glu+Pro)/(Orn+Trp+ABA) |
| 89 | 0.890918 | (Glu)/(Trp)+(Pro+Ile+Gly)/(Orn+Thr+ABA) |
| 90 | 0.890775 | (Gly)/(Ala+Cit)+(Glu+Pro+Ile)/(Orn+Trp) |
| 91 | 0.890722 | (Glu+Ile)/(Orn+Trp)+(Pro+Gly)/(BCAA+Gln) |
| 92 | 0.890707 | (Gly)/(Tyr+Lys)+(Glu+Pro+Ile)/(Trp+ABA) |
| 93 | 0.890643 | (Gly)/(Arg+Met+Thr)+(Glu+Pro)/(Trp+ABA) |
| 94 | 0.890585 | (Gly)/(Gln)+(Glu+Pro)/(Trp+ABA+Asn) |
| 95 | 0.890501 | (Glu+Pro)/(Trp+ABA)+(Ile+Gly)/(Arg+Thr) |
| 96 | 0.890324 | (Gly)/(Orn+Gln)+(Glu+Pro+Ile)/(Trp+ABA) |
| 97 | 0.89029 | (Glu)/(Trp)+(Pro)/(Orn+ABA) |
| 98 | 0.890284 | (Gly)/(Arg+Leu+Thr)+(Glu+Pro)/(Trp+ABA) |
| 99 | 0.890172 | (Gly)/(BCAA)+(Glu+Pro+Ile)/(Trp+Thr) |
| 100 | 0.890061 | (Gly)/(Orn+Met+Lys)+(Glu+Pro)/(Trp+ABA) |

FIG.51

| RANK | VALUE | FORMULA |
|---|---|---|
| 1 | 0.797086 | (0.442298)+(0.034770)Glu-(0.135162)Asn+(0.010116)Gln-(0.112853)ABA |
| 2 | 0.787721 | -(1.331580)-(0.192925)Asn+(0.008557)Gln+(0.102299)Cit+(0.085761)Met |
| 3 | 0.783559 | -(0.924125)-(0.137849)Asn+(0.009788)Gln-(0.023428)Thr+(0.121373)Met |
| 4 | 0.782518 | -(1.532025)+(0.021254)Glu-(0.163832)Asn+(0.009578)Gln+(0.105469)Cit |
| 5 | 0.781478 | (0.597186)-(0.168819)Asn+(0.008263)Gln-(0.081781)ABA+(0.106670)Met |
| 6 | 0.778356 | (1.142824)-(0.182591)Asn+(0.007677)Gln-(0.008334)Val+(0.144224)Met |
| 7 | 0.777315 | (0.439529)-(0.161179)Asn+(0.008962)Gln+(0.121716)Cit-(0.081896)ABA |
| 8 | 0.776275 | (0.806246)-(0.157211)Asn+(0.008175)Gln-(0.112850)ABA+(0.014064)Lys |
| 9 | 0.776275 | -(0.208249)-(0.010759)Ser-(0.151642)Asn+(0.009597)Gln+(0.106988)Cit |
| 10 | 0.775234 | -(1.197731)+(0.032787)Glu+(0.008662)Gln-(0.031725)Thr-(0.095885)ABA |
| 11 | 0.774194 | -(1.267084)+(0.018614)Glu-(0.164321)Asn+(0.009007)Gln+(0.080432)Met |
| 12 | 0.774194 | (0.062271)-(0.171271)Asn-(0.006133)Gly+(0.009751)Gln+(0.100447)Met |
| 13 | 0.772112 | -(1.240570)+(0.007899)Gln-(0.046294)Thr-(0.008019)Val+(0.124116)Met |
| 14 | 0.771072 | -(0.758445)-(0.152521)Asn+(0.009673)Gln+(0.124244)Cit-(0.010983)Arg |
| 15 | 0.771072 | -(0.424141)-(0.153838)Asn+(0.009103)Gln+(0.144935)Cit-(0.026086)Orn |
| 16 | 0.770031 | -(0.069402)-(0.159615)Asn+(0.008218)Gln+(0.126136)Met-(0.025196)Phe |
| 17 | 0.768991 | -(0.648434)-(0.165337)Asn+(0.008330)Gln-(0.000119)Ala+(0.097065)Met |
| 18 | 0.768991 | -(0.775198)-(0.134852)Asn+(0.010128)Gln-(0.019509)Thr+(0.127178)Cit |
| 19 | 0.768991 | -(0.642475)-(0.160234)Asn+(0.008848)Gln-(0.006732)Arg+(0.098457)Met |
| 20 | 0.76795 | -(1.046304)-(0.168078)Asn+(0.008489)Gln+(0.115004)Cit+(0.011275)Tyr |
| 21 | 0.76795 | -(0.011521)-(0.014435)Ser-(0.157199)Asn+(0.009418)Gln+(0.095611)Met |
| 22 | 0.76795 | (2.301873)-(0.148815)Asn+(0.113206)Cit-(0.072756)ABA+(0.106453)Met |
| 23 | 0.766909 | -(0.425507)-(0.008754)Pro-(0.157041)Asn+(0.008311)Gln+(0.121396)Met |
| 24 | 0.765869 | (1.258768)+(0.044440)Glu-(0.133130)Asn+(0.009326)Gln-(0.010890)Val |
| 25 | 0.764828 | (3.953327)+(0.038492)Glu-(0.138047)Asn-(0.015488)Val+(0.158689)Met |
| 26 | 0.764828 | (0.812935)-(0.131926)Asn+(0.008926)Gln-(0.089002)ABA+(0.007438)Leu |
| 27 | 0.763788 | -(0.655134)-(0.165624)Asn+(0.008325)Gln+(0.096179)Met |
| 28 | 0.763788 | -(0.780433)+(0.025335)Glu-(0.108077)Asn+(0.010465)Gln-(0.016348)Thr |
| 29 | 0.762747 | -(0.233931)-(0.169155)Asn+(0.008079)Gln+(0.120626)Met-(0.006705)Leu |
| 30 | 0.762747 | (1.090092)-(0.107461)Asn+(0.009458)Gln-(0.010135)Thr-(0.068644)ABA |
| 31 | 0.762747 | (0.805744)-(0.127643)Asn+(0.009064)Gln-(0.087501)ABA+(0.009348)Ile |
| 32 | 0.762747 | -(0.488765)-(0.005916)Pro-(0.152282)Asn+(0.008887)Gln+(0.126333)Cit |
| 33 | 0.762747 | -(0.158343)-(0.162929)Asn-(0.004364)Gly+(0.009812)Gln+(0.112702)Cit |
| 34 | 0.762747 | (0.655181)-(0.105032)Asn+(0.009536)Gln-(0.013429)Thr-(0.002139)Val |

FIG.52

| RANK | VALUE | FORMULA |
|---|---|---|
| 35 | 0.762747 | −(0.948711)−(0.170608)Asn+(0.008678)Gln+(0.113639)Cit+(0.001919)Ala |
| 36 | 0.761707 | (0.524199)−(0.167441)Asn+(0.008001)Gln+(0.119767)Met−(0.023808)Trp |
| 37 | 0.761707 | −(0.353055)−(0.110828)Asn+(0.009580)Gln−(0.015968)Thr+(0.013565)Tyr |
| 38 | 0.761707 | −(1.085254)−(0.174519)Asn+(0.008311)Gln+(0.113737)Cit+(0.006277)Lys |
| 39 | 0.760666 | −(0.358042)−(0.161549)Asn+(0.008444)Gln−(0.009559)His+(0.103329)Met |
| 40 | 0.759625 | (2.803408)−(0.164396)Asn+(0.107454)Cit−(0.008003)Val+(0.142717)Met |
| 41 | 0.758585 | (2.767317)−(0.131136)Asn−(0.010041)Gly+(0.011450)Gln−(0.102443)ABA |
| 42 | 0.758585 | (1.155333)−(0.127510)Asn+(0.008631)Gln−(0.081059)ABA+(0.007773)Orn |
| 43 | 0.758585 | −(0.104683)−(0.107655)Asn+(0.009811)Gln−(0.013617)Thr+(0.003180)Ile |
| 44 | 0.758585 | −(1.524677)+(0.007845)Gln−(0.039271)Thr−(0.067655)ABA+(0.079116)Met |
| 45 | 0.758585 | −(0.123011)−(0.109069)Asn+(0.009750)Gln−(0.013609)Thr+(0.002678)Leu |
| 46 | 0.758585 | (1.820080)−(0.145234)Asn+(0.008275)Gln−(0.015819)Val+(0.026689)Leu |
| 47 | 0.758585 | (0.764210)−(0.135070)Asn+(0.008717)Gln−(0.075339)ABA+(0.015149)Phe |
| 48 | 0.758585 | −(0.181810)−(0.171263)Asn+(0.007880)Gln+(0.118328)Met−(0.008979)Ile |
| 49 | 0.757544 | −(0.761012)+(0.023156)Glu−(0.133846)Asn+(0.009203)Gln+(0.002187)Tyr |
| 50 | 0.757544 | −(2.314005)−(0.010614)Pro+(0.008527)Gln−(0.041967)Thr+(0.118388)Met |
| 51 | 0.757544 | (1.048695)−(0.123864)Asn+(0.008796)Gln−(0.078556)ABA+(0.000892)Val |
| 52 | 0.757544 | (0.871100)−(0.138183)Asn+(0.008024)Gln+(0.022075)Tyr−(0.005898)Val |
| 53 | 0.757544 | −(0.210215)+(0.023682)Glu−(0.014645)Ser−(0.124762)Asn+(0.010672)Gln |
| 54 | 0.757544 | −(0.351726)+(0.004977)Gln−(0.085397)ABA+(0.084276)Met−(0.053748)Phe |
| 55 | 0.757544 | (1.199480)−(0.121239)Asn+(0.008920)Gln−(0.002142)Arg−(0.073886)ABA |
| 56 | 0.757544 | −(0.735214)−(0.167628)Asn+(0.008270)Gln+(0.092223)Met+(0.001535)Lys |
| 57 | 0.756504 | −(0.881382)−(0.162264)Asn+(0.008811)Gln+(0.113603)Cit+(0.002036)Leu |
| 58 | 0.756504 | (0.817119)−(0.134446)Asn+(0.008538)Gln−(0.083361)ABA+(0.015687)Tyr |
| 59 | 0.756504 | (1.312633)−(0.122425)Asn+(0.008717)Gln−(0.074448)ABA−(0.001985)Trp |
| 60 | 0.756504 | −(0.354978)−(0.159241)Asn+(0.008377)Gln−(0.022156)Orn+(0.116062)Met |
| 61 | 0.756504 | (1.750053)−(0.014172)Ser−(0.114748)Asn+(0.009907)Gln−(0.073689)ABA |
| 62 | 0.756504 | (1.198155)+(0.000567)Pro−(0.124581)Asn+(0.008735)Gln−(0.075564)ABA |
| 63 | 0.756504 | −(0.169377)−(0.137829)Asn+(0.008266)Gln−(0.025537)Orn+(0.011769)Lys |
| 64 | 0.756504 | −(0.675101)+(0.023958)Glu−(0.131827)Asn+(0.009293)Gln−(0.001208)His |
| 65 | 0.756504 | −(0.030548)−(0.108053)Asn+(0.009658)Gln+(0.004021)His−(0.014271)Thr |
| 66 | 0.756504 | (1.510318)−(0.132295)Asn+(0.008954)Gln−(0.014257)Val+(0.033359)Ile |
| 67 | 0.756504 | (0.308960)−(0.104362)Asn+(0.009657)Gln−(0.013821)Thr−(0.003545)Trp |
| 68 | 0.755463 | −(1.146617)−(0.170857)Asn+(0.008728)Gln+(0.113829)Cit+(0.014358)Phe |

FIG.53

| RANK | VALUE | FORMULA |
|---|---|---|
| 69 | 0.755463 | −(0.449099)−(0.168225)Asn+(0.008432)Gln−(0.012461)Tyr+(0.123011)Met |
| 70 | 0.755463 | −(0.720881)+(0.023869)Glu−(0.132646)Asn+(0.009277)Gln |
| 71 | 0.755463 | (0.328677)−(0.015867)Ser−(0.133410)Asn+(0.009501)Gln+(0.007034)Lys |
| 72 | 0.755463 | −(0.713232)+(0.023461)Glu−(0.128960)Asn+(0.009576)Gln−(0.003594)Arg |
| 73 | 0.755463 | (2.148170)−(0.156060)Asn+(0.135159)Cit−(0.105971)ABA+(0.017657)Lys |
| 74 | 0.754422 | −(0.686861)−(0.160017)Asn+(0.008702)Gln+(0.114466)Cit |
| 75 | 0.754422 | (1.023914)−(0.140522)Asn+(0.008604)Gln+(0.002833)Ala−(0.080797)ABA |
| 76 | 0.754422 | (0.642834)−(0.013378)Ser−(0.102469)Asn+(0.010720)Gln−(0.011517)Thr |
| 77 | 0.754422 | (0.177157)−(0.001364)Pro−(0.103844)Asn+(0.009699)Gln−(0.013324)Thr |
| 78 | 0.754422 | −(0.890399)−(0.161384)Asn+(0.008859)Gln+(0.113972)Cit+(0.002770)Ile |
| 79 | 0.753382 | −(0.830662)+(0.023344)Glu−(0.135521)Asn+(0.009263)Gln+(0.004023)Phe |
| 80 | 0.753382 | (0.205172)−(0.103105)Asn+(0.009775)Gln−(0.013722)Thr−(0.005059)Orn |
| 81 | 0.753382 | (0.109939)−(0.106023)Asn+(0.009701)Gln−(0.013727)Thr |
| 82 | 0.753382 | −(0.551911)−(0.158942)Asn+(0.008659)Gln+(0.114397)Cit−(0.002333)Trp |
| 83 | 0.753382 | −(0.739037)+(0.004980)Gln+(0.040096)Cit−(0.087272)ABA−(0.022368)Trp |
| 84 | 0.753382 | −(0.481900)+(0.022510)Glu−(0.133397)Asn−(0.001483)Gly+(0.009588)Gln |
| 85 | 0.753382 | (1.563630)−(0.015829)Ser−(0.115205)Asn+(0.009723)Gln−(0.003031)Val |
| 86 | 0.753382 | (4.013703)−(0.134271)Asn−(0.015523)Val+(0.146647)Met+(0.020236)Ile |
| 87 | 0.753382 | (1.519117)−(0.010188)Pro−(0.139672)Asn+(0.121124)Cit+(0.124338)Met |
| 88 | 0.753382 | (4.410123)−(0.146142)Asn−(0.019804)Val+(0.135573)Met+(0.023032)Leu |
| 89 | 0.753382 | −(0.515339)−(0.156960)Asn+(0.008846)Gln−(0.005857)His+(0.117887)Cit |
| 90 | 0.753382 | (1.206839)−(0.123307)Asn+(0.008742)Gln−(0.074567)ABA |
| 91 | 0.752341 | (1.215762)−(0.123141)Asn+(0.008746)Gln−(0.000233)His−(0.074588)ABA |
| 92 | 0.752341 | (2.727608)+(0.021872)Glu−(0.111625)Asn−(0.088248)ABA+(0.097942)Met |
| 93 | 0.752341 | (0.413852)−(0.013857)Ser−(0.124276)Asn+(0.009653)Gln+(0.008547)Tyr |
| 94 | 0.752341 | (3.153887)−(0.120607)Asn−(0.001112)Gly−(0.070752)ABA+(0.120204)Met |
| 95 | 0.752341 | −(0.491609)+(0.026218)Glu−(0.123182)Asn+(0.009447)Gln−(0.015676)Orn |
| 96 | 0.752341 | (0.108601)−(0.104978)Asn+(0.009835)Gln−(0.013335)Thr−(0.001779)Arg |
| 97 | 0.752341 | (2.901963)−(0.121833)Asn+(0.000336)Ala−(0.068766)ABA+(0.115851)Met |
| 98 | 0.751301 | (0.489851)−(0.023775)Ser−(0.006762)Pro+(0.007645)Gln−(0.079143)ABA |
| 99 | 0.751301 | −(0.364680)−(0.118802)Asn+(0.009291)Gln−(0.015511)Thr+(0.007230)Lys |
| 100 | 0.751301 | (0.907587)−(0.012361)Ser−(0.121400)Asn−(0.002414)Gly+(0.010329)Gln |

FIG.55

| RANK | VALUE | FORMULA |
|---|---|---|
| 1 | 0.774194 | (7.622e-01)Asn-(4.336e-02)Gln-(6.428e-01)Cit+(6.352e-02)Arg+(8.352e-01) |
| 2 | 0.773153 | (8.404e-01)Asn-(4.564e-02)Gln+(5.364e-01)ABA-(6.271e-02)Lys-(4.553e+00) |
| 3 | 0.773153 | (8.590e-01)Asn+(3.395e-02)Gly-(4.525e-02)Gln-(5.088e-01)Met-(2.908e+00) |
| 4 | 0.772112 | (8.518e-01)Asn-(4.421e-02)Gln+(3.860e-02)Arg-(5.206e-01)Met+(1.524e+00) |
| 5 | 0.772112 | (7.757e-01)Asn-(3.330e-02)Gln+(4.351e-02)Val-(6.287e-01)Met-(6.110e+00) |
| 6 | 0.772112 | -(8.595e-02)Glu+(8.307e-01)Asn-(4.039e-02)Gln-(5.486e-01)Cit+(3.011e+00) |
| 7 | 0.771072 | -(8.209e-02)Glu+(8.927e-01)Asn-(4.329e-02)Gln-(4.411e-01)Met+(3.342e+00) |
| 8 | 0.770031 | (7.206e-01)Asn-(4.030e-02)Gln-(6.767e-01)Cit+(1.458e-01)Orn-(4.434e-01) |
| 9 | 0.770031 | (5.927e-02)Pro+(7.594e-01)Asn-(3.899e-02)Gln-(6.468e-01)Met+(5.196e-01) |
| 10 | 0.770031 | (5.294e-02)Ser+(8.132e-01)Asn-(4.342e-02)Gln-(5.780e-01)Cit-(2.549e+00) |
| 11 | 0.768991 | (7.584e-01)Asn-(3.702e-02)Gln-(6.332e-01)Met+(1.498e-01)Phe-(1.755e+00) |
| 12 | 0.768991 | (8.364e-01)Asn-(5.481e-02)Gln+(5.446e-01)ABA-(2.930e-02)Leu-(7.868e+00) |
| 13 | 0.76795 | (8.215e-01)Asn-(3.725e-02)Gln-(5.670e-01)Cit-(4.797e-02)Tyr+(2.461e+00) |
| 14 | 0.76795 | -(5.809e-02)Gln+(3.495e-01)Thr+(5.872e-02)Val-(9.333e-01)Met+(8.794e+00) |
| 15 | 0.76795 | (8.344e-01)Asn-(3.530e-02)Gln-(5.492e-01)Cit-(2.874e-02)Lys+(2.695e+00) |
| 16 | 0.766909 | (7.779e-02)Ser+(8.475e-01)Asn-(4.495e-02)Gln-(5.232e-01)Met-(2.851e+00) |
| 17 | 0.765869 | -(3.036e-01)Glu+(9.466e-01)Asn-(6.298e-02)Gln+(8.850e-02)Val-(1.371e+01) |
| 18 | 0.764828 | (8.053e-01)Asn-(3.814e-02)Gln-(5.901e-01)Met+(4.243e-02)Leu+(8.580e-02) |
| 19 | 0.764828 | (8.703e-01)Asn-(5.586e-02)Gln+(4.842e-01)ABA-(7.045e-02)Phe-(6.736e+00) |
| 20 | 0.763788 | -(8.351e-01)Asn+(5.667e-02)Gln-(5.460e-01)ABA+(3.617e-02)Ile+(7.878e+00) |
| 21 | 0.763788 | (6.632e-01)Asn-(5.200e-01)Cit+(2.905e-01)ABA-(4.532e-01)Met-(9.921e+00) |
| 22 | 0.761707 | -(1.775e-01)Glu+(6.434e-01)Asn+(7.445e-02)Val-(7.410e-01)Met-(1.896e+01) |
| 23 | 0.761707 | (8.668e-01)Asn-(4.039e-02)Gln-(4.971e-01)Met+(1.518e+00) |
| 24 | 0.761707 | (7.945e-01)Asn-(3.652e-02)Gln+(6.988e-02)Tyr-(6.022e-01)Met+(1.210e-01) |
| 25 | 0.761707 | -(2.070e-01)Glu+(9.564e-01)Asn-(8.918e-02)Gln+(1.856e-01)Thr-(9.440e-01) |
| 26 | 0.760666 | (8.592e-01)Asn-(4.025e-02)Gln+(1.803e-03)Ala-(5.101e-01)Met+(1.414e+00) |
| 27 | 0.760666 | (7.994e-01)Asn-(3.630e-02)Gln-(5.841e-01)Met+(1.359e-01)Trp-(4.653e+00) |
| 28 | 0.759625 | (8.588e-01)Asn-(5.456e-02)Gln+(5.031e-01)ABA-(8.034e-02)Tyr-(6.116e+00) |
| 29 | 0.759625 | (8.751e-01)Asn-(5.510e-02)Gln-(1.143e-02)Ala+(4.807e-01)ABA-(7.415e+00) |
| 30 | 0.759625 | (8.212e-01)Asn+(2.290e-02)Gly-(4.352e-02)Gln-(5.685e-01)Cit-(2.526e+00) |
| 31 | 0.759625 | -(9.733e-01)Asn+(8.222e-02)Gln-(1.721e-01)Thr+(1.273e-01)Tyr+(2.843e-01) |
| 32 | 0.758585 | -(1.541e-01)Glu+(9.647e-02)Ser+(9.809e-01)Asn-(6.903e-02)Gln-(5.223e+00) |
| 33 | 0.758585 | -(6.753e-02)Gln+(3.466e-01)Thr+(6.146e-01)ABA-(7.055e-01)Met+(1.250e+01) |
| 34 | 0.758585 | -(8.551e-01)Asn+(6.239e-02)Gln-(2.700e-02)Arg-(5.140e-01)ABA+(9.633e+00) |

FIG.56

| RANK | VALUE | FORMULA |
|---|---|---|
| 35 | 0.758585 | (8.763e-01)Asn-(4.022e-02)Gln-(4.800e-01)Met-(6.371e-03)Lys+(1.818e+00) |
| 36 | 0.758585 | -(9.847e-01)Asn+(8.733e-02)Gln-(1.464e-01)Thr-(3.671e-02)Val+(1.310e+01) |
| 37 | 0.757544 | (7.990e-01)Asn+(6.153e-02)Gly-(6.614e-02)Gln+(5.945e-01)ABA-(1.841e+01) |
| 38 | 0.757544 | (9.695e-01)Asn-(5.745e-02)Gln+(2.211e-01)Orn-(8.834e-02)Lys-(2.027e-01) |
| 39 | 0.757544 | (8.601e-01)Asn-(5.868e-02)Gln+(5.067e-01)ABA-(2.600e-03)Orn-(9.322e+00) |
| 40 | 0.757544 | -(3.723e-02)Gln+(6.143e-01)ABA-(6.621e-01)Met+(4.276e-01)Phe+(2.207e+00) |
| 41 | 0.757544 | (8.256e-01)Asn-(4.092e-02)Gln+(8.006e-02)His-(5.570e-01)Met-(9.679e-01) |
| 42 | 0.756504 | -(8.508e-02)Pro+(6.330e-02)Gln-(3.239e-01)Thr+(9.401e-01)Met-(1.680e+01) |
| 43 | 0.756504 | (9.857e-01)Asn-(5.665e-02)Gln-(1.507e-01)Tyr+(4.943e-02)Val-(8.738e+00) |
| 44 | 0.756504 | (7.963e-01)Asn-(4.012e-02)Gln+(4.485e-02)His-(6.019e-01)Cit-(9.336e-01) |
| 45 | 0.756504 | (9.743e-01)Asn-(4.977e-02)Gln+(1.243e-01)Val-(1.809e-01)Leu-(1.951e+01) |
| 46 | 0.756504 | (8.609e-01)Asn-(5.888e-02)Gln+(5.054e-01)ABA-(9.349e+00) |
| 47 | 0.755463 | -(8.571e-01)Asn+(5.952e-02)Gln-(5.098e-01)ABA-(4.390e-02)Trp+(1.176e+01) |
| 48 | 0.755463 | (7.818e-01)Asn-(4.158e-02)Gln+(1.512e-01)Orn-(6.035e-01)Met+(7.054e-01) |
| 49 | 0.755463 | (8.243e-01)Asn-(3.743e-02)Gln-(5.624e-01)Cit-(5.340e-02)Phe+(2.335e+00) |
| 50 | 0.755463 | (8.764e-01)Asn-(6.002e-02)Gln+(4.778e-01)ABA+(8.253e-03)Val-(1.087e+01) |
| 51 | 0.755463 | (5.040e-02)Gln+(4.296e-01)Cit-(8.727e-01)ABA-(2.266e-01)Trp-(7.943e+00) |
| 52 | 0.755463 | (8.316e-02)Ser+(9.936e-01)Asn+(2.144e-02)Gly-(7.286e-02)Gln-(1.207e+01) |
| 53 | 0.755463 | (9.642e-01)Asn-(6.050e-02)Gln+(1.175e-01)Val-(2.301e-01)Ile-(1.767e+01) |
| 54 | 0.755463 | (6.728e-01)Asn-(4.427e-01)Cit+(3.523e-02)Val-(5.917e-01)Met-(1.182e+01) |
| 55 | 0.754422 | (9.769e-02)Ser+(9.905e-01)Asn-(6.667e-02)Gln-(6.993e-02)Tyr-(7.261e+00) |
| 56 | 0.754422 | -(9.778e-01)Asn+(8.146e-02)Gln-(1.913e-01)Thr+(2.767e-02)Ala+(1.371e+00) |
| 57 | 0.754422 | (6.675e-01)Asn+(8.567e-02)Val-(7.300e-01)Met-(1.191e-01)Ile-(2.090e+01) |
| 58 | 0.754422 | (4.914e-02)Pro+(6.154e-01)Asn-(5.434e-01)Cit-(5.689e-01)Met-(6.579e+00) |
| 59 | 0.754422 | -(9.807e-01)Asn+(8.817e-02)Gln-(1.561e-01)Thr-(7.776e-02)Trp+(9.464e+00) |
| 60 | 0.754422 | -(1.578e-01)Glu+(9.844e-01)Asn-(6.681e-02)Gln+(4.021e-02)Arg+(4.159e-01) |
| 61 | 0.753382 | (1.085e-01)Ser+(8.188e-01)Asn-(6.584e-02)Gln+(5.598e-01)ABA-(1.638e+01) |
| 62 | 0.753382 | -(9.851e-01)Asn+(8.664e-02)Gln-(1.485e-01)Thr-(6.356e-03)Arg+(5.268e+00) |
| 63 | 0.753382 | (9.494e-02)Ser+(9.825e-01)Asn-(9.083e-02)Gln+(1.318e-01)Thr-(1.084e+01) |
| 64 | 0.753382 | -(8.128e-01)Asn+(7.659e-02)Gln-(1.250e-01)Thr-(5.638e-01)ABA+(1.076e+01) |
| 65 | 0.753382 | (4.275e-02)Pro+(7.586e-01)Asn-(4.098e-02)Gln-(6.488e-01)Cit-(7.690e-01) |
| 66 | 0.753382 | (9.970e-01)Asn+(3.020e-02)Gly-(6.026e-02)Gln-(3.748e-02)Lys-(5.192e+00) |
| 67 | 0.753382 | (8.288e-01)Asn-(3.821e-02)Gln-(5.583e-01)Cit-(5.583e-03)Ala+(1.296e+00) |
| 68 | 0.752341 | -(9.850e-01)Asn+(8.592e-02)Gln-(1.497e-01)Thr+(5.227e+00) |

FIG.57

| RANK | VALUE | FORMULA |
|---|---|---|
| 69 | 0.752341 | (9.951e-01)Asn+(3.511e-02)Gly-(6.484e-02)Gln-(6.631e-02)Tyr-(6.235e+00) |
| 70 | 0.752341 | -(1.044e-01)Pro+(6.026e-02)Gln-(8.397e-01)ABA+(5.294e-01)Met-(1.983e+01) |
| 71 | 0.752341 | -(1.609e-01)Glu+(9.850e-01)Asn-(6.231e-02)Gln+(2.877e-03)Ala+(3.921e-01) |
| 72 | 0.752341 | (1.031e-01)Ser+(9.924e-01)Asn-(6.487e-02)Gln-(1.548e-02)Ala-(8.062e+00) |
| 73 | 0.752341 | (8.129e-01)Asn-(3.635e-02)Gln-(5.782e-01)Met+(5.952e-02)Ile-(4.285e-01) |
| 74 | 0.751301 | -(9.765e-01)Asn+(9.357e-02)Gln-(1.544e-01)Thr-(1.180e-01)Orn+(6.992e+00) |
| 75 | 0.751301 | (6.654e-01)Asn+(6.673e-03)Gly+(3.570e-01)ABA-(6.556e-01)Met-(1.724e+01) |
| 76 | 0.751301 | (8.139e-01)Asn-(3.900e-02)Gln-(5.797e-01)Cit+(6.725e-01) |
| 77 | 0.751301 | -(9.846e-01)Asn+(8.657e-02)Gln-(1.509e-01)Thr-(1.724e-02)Ile+(6.106e+00) |
| 78 | 0.751301 | (7.283e-01)Asn+(1.082e-01)Val-(6.640e-01)Met-(1.303e-01)Leu-(2.292e+01) |
| 79 | 0.751301 | (3.558e-02)Pro+(9.852e-01)Asn-(9.035e-02)Gln+(1.415e-01)Thr-(6.960e+00) |
| 80 | 0.751301 | (1.077e-01)Ser+(9.909e-01)Asn-(6.080e-02)Gln-(5.303e-02)Lys-(6.370e+00) |
| 81 | 0.75026 | -(1.438e-01)Glu+(9.876e-01)Asn-(6.037e-02)Gln-(2.008e-02)Tyr+(1.088e+00) |
| 82 | 0.75026 | -(1.670e-01)Glu+(9.783e-01)Asn-(6.276e-02)Gln+(1.058e-01)Trp-(4.684e+00) |
| 83 | 0.75026 | -(1.273e-01)Glu+(6.608e-01)Asn+(4.803e-01)ABA-(5.625e-01)Met-(1.592e+01) |
| 84 | 0.75026 | (4.461e-02)Ser+(6.448e-01)Asn+(3.634e-01)ABA-(6.709e-01)Met-(1.943e+01) |
| 85 | 0.75026 | -(2.106e-01)Glu+(9.519e-01)Asn-(7.217e-02)Gln+(2.104e-01)Orn-(6.691e-01) |
| 86 | 0.75026 | (1.366e-01)Ser+(9.867e-01)Asn-(7.572e-02)Gln+(4.503e-02)Val-(2.208e+01) |
| 87 | 0.75026 | -(9.847e-01)Asn+(8.513e-02)Gln+(1.693e-02)His-(1.512e-01)Thr+(4.545e+00) |
| 88 | 0.75026 | -(9.848e-01)Asn+(8.660e-02)Gln-(1.504e-01)Thr-(5.751e-03)Leu+(5.591e+00) |
| 89 | 0.75026 | (9.860e-01)Asn+(3.717e-02)Gly-(8.990e-02)Gln+(1.354e-01)Thr-(1.014e+01) |
| 90 | 0.75026 | (9.767e-01)Asn-(7.867e-02)Gln+(1.480e-01)Thr-(1.337e-01)Phe-(6.059e-01) |
| 91 | 0.74922 | (1.140e-01)Ser+(9.906e-01)Asn-(7.346e-02)Gln+(1.808e-02)Leu-(1.216e+01) |
| 92 | 0.74922 | (9.963e-01)Asn+(3.783e-02)Gly-(7.248e-02)Gln+(2.609e-02)Arg-(9.448e+00) |
| 93 | 0.74922 | (9.966e-01)Asn+(4.103e-02)Gly-(7.070e-02)Gln+(1.345e-02)Leu-(1.052e+01) |
| 94 | 0.74922 | (2.406e-02)Pro+(8.643e-01)Asn-(6.290e-02)Gln+(4.985e-01)ABA-(1.050e+01) |
| 95 | 0.74922 | -(8.739e-02)Pro+(5.639e-02)Gln+(5.997e-01)Cit-(7.934e-01)ABA-(1.819e+01) |
| 96 | 0.74922 | -(9.816e-01)Asn+(7.483e-02)Gln-(1.629e-01)Thr+(6.653e-02)Lys-(6.095e-02) |
| 97 | 0.74922 | (7.090e-01)Asn-(4.339e-02)Arg+(3.499e-01)ABA-(6.107e-01)Met-(1.465e+01) |
| 98 | 0.74922 | -(5.243e-02)Gln+(3.233e-01)Thr-(8.980e-01)Met+(2.937e-01)Trp+(2.537e+00) |
| 99 | 0.74922 | -(2.050e-01)Glu+(6.854e-02)Pro+(9.737e-01)Asn-(7.136e-02)Gln-(1.239e+00) |
| 100 | 0.74922 | (9.949e-01)Asn+(5.484e-02)Gly-(7.378e-02)Gln+(4.153e-02)Val-(2.047e+01) |

FIG.59

| RANK | VALUE | FORMULA FORMULA |
|---|---|---|
| 1 | 0.848605 | (Glu+Gln)/(Val+Thr+Ser)+(Cit+Met)/(Asn) |
| 2 | 0.843797 | (Glu+Gln)/(Val+Pro+Ser)+(Cit+Met)/(Asn) |
| 3 | 0.843446 | (Met)/(Asn)+(Glu+Gln+Lys)/(LNAA+Thr+Ser) |
| 4 | 0.84301 | (Gln+Gly)/(Val+Thr)+(Glu+Cit+Met)/(Asn) |
| 5 | 0.842134 | (Gln+Tyr)/(Val+ABA)+(Glu+Cit+Met)/(Asn) |
| 6 | 0.841135 | (Gln+Leu)/(Val+ABA)+(Glu+Cit+Met)/(Asn) |
| 7 | 0.840059 | (Glu+Gln)/(BCAA+Thr+Ser)+(Cit+Met)/(Asn) |
| 8 | 0.839956 | (Glu+Gln)/(BCAA+Pro+Thr)+(Cit+Met)/(Asn) |
| 9 | 0.839785 | (Glu+Gln)/(BCAA+Arg+Thr)+(Cit+Met)/(Asn) |
| 10 | 0.839377 | (Gln)/(Val+ABA)+(Glu+Cit+Met)/(Asn) |
| 11 | 0.839165 | (Met)/(Asn)+(Glu+Gln+Ile)/(BCAA+Thr+Ser) |
| 12 | 0.838577 | (Glu+Gln)/(Arg+Val+Thr)+(Cit+Met)/(Asn) |
| 13 | 0.838368 | (Gln)/(Val+Ser)+(Glu+Cit+Met)/(ABA+Asn) |
| 14 | 0.838252 | (Glu+Gln)/(AAA+Arg+Val)+(Cit+Met)/(Asn) |
| 15 | 0.837726 | (Gln+Leu)/(AAA+Arg+Val)+(Cit+Met)/(Asn) |
| 16 | 0.837078 | (Glu+Gln)/(AAA+Thr+Ser)+(Cit+Met)/(An) |
| 17 | 0.836923 | (Gln+Ile)/(AAA+Arg+Val)+(Cit+Met)/(Asn) |
| 18 | 0.836859 | (Glu+Gln)/(Arg+Val+Ser)+(Cit+Met)/(Asn) |
| 19 | 0.836538 | (Met)/(Asn)+(Glu+Gln+Ile)/(LNAA+Thr+Ser) |
| 20 | 0.83648 | (Glu+Met)/(Asn)+(Gln+Tyr+Gly)/(Val+Thr) |
| 21 | 0.836351 | (Glu+Gln)/(BCAA+Arg+Pro)+(Cit+Met)/(Asn) |
| 22 | 0.836316 | (Glu+Met)/(Asn)+(Gln+Gly)/(Val+Orn+Thr) |
| 23 | 0.836245 | (Met)/(Asn)+(Glu+Gln)/(BCAA+Trp+Thr+Ser) |
| 24 | 0.836231 | (Met)/(Asn)+(Glu+Gln+Leu)/(LNAA+Phe+Ser) |
| 25 | 0.836219 | (Gln+Leu)/(AAA+Val+Ser)+(Cit+Met)/(Asn) |
| 26 | 0.836203 | (Met)/(Asn)+(Gln+Lys)/(LNAA+Orn+Thr+Ser) |
| 27 | 0.836036 | (Gln)/(AAA+Arg+Val+ABA)+(Cit+Met)/(Asn) |
| 28 | 0.835973 | (Glu+Gln)/(AAA+Val+Thr)+(Cit+Met)/(Asn) |
| 29 | 0.835828 | (Glu+Gln)/(BCAA+Orn+Thr)+(Cit+Met)/(Asn) |
| 30 | 0.835753 | (Met)/(Asn)+(Glu+Gln+Cit)/(BCAA+Thr+Ser) |
| 31 | 0.835732 | (Glu+Gln)/(Val+Pro+Thr)+(Cit+Met)/(Asn) |
| 32 | 0.83564 | (Met)/(Asn)+(Glu+Gln+Leu)/(LNAA+Ser+ABA) |
| 33 | 0.83562 | (Gln+Lys)/(Val+Thr+Ser)+(Cit+Met)/(Asn) |
| 34 | 0.835529 | (Glu+Gln)/(BCAA+Pro+Ser)+(Cit+Met)/(Asn) |

FIG.60

| RANK | VALUE | FORMULA FORMULA |
|---|---|---|
| 35 | 0.835322 | (Gln+Lys)/(LNAA+Arg+Thr)+(Cit+Met)/(Asn) |
| 36 | 0.835288 | (Glu+Gln)/(LNAA+Thr+ABA)+(Cit+Met)/(Asn) |
| 37 | 0.835257 | (Glu+Met)/(Asn)+(Gln+Gly+Leu)/(Val+Thr) |
| 38 | 0.835224 | (Met)/(Asn)+(Glu+Gln+Ile)/(LNAA+Phe+Ser) |
| 39 | 0.83512 | (Gln+Gly)/(Val+Ser)+(Glu+Cit+Met)/(Asn) |
| 40 | 0.834895 | (Glu+Gln)/(AAA+Val+Pro)+(Cit+Met)/(Asn) |
| 41 | 0.834709 | (Cit+Met)/(Asn)+(Glu+Gln+Tyr)/(LNAA+Thr) |
| 42 | 0.834623 | (Met)/(Asn)+(Glu+Gln+Lys)/(LNAA+Arg+Thr) |
| 43 | 0.834531 | (Glu+Gln)/(Arg+Val+Pro)+(Cit+Met)/(Asn) |
| 44 | 0.834477 | (Glu+Cit+Met)/(Asn)+(Gln+Tyr+Ie)/(Val) |
| 45 | 0.834469 | (Met)/(Asn)+(Glu+Gln)/(BCAA+Thr+Ser+ABA) |
| 46 | 0.834271 | (Cit+Met)/(Asn)+(Gln+Lys+Leu)/(LNAA+Arg) |
| 47 | 0.834256 | (Glu+Met)/(Asn)+(Gln+Cit+Gly)/(Val+Thr) |
| 48 | 0.834231 | (Met)/(Asn)+(Glu+Gln+Ile)/(LNAA+Ser+ABA) |
| 49 | 0.834135 | (Met)/(Asn)+(Glu+Gln+Ile+Lys)/(LNAA+Thr) |
| 50 | 0.834054 | (Gln+Gly)/(Val+Phe)+(Glu+Cit+Met)/(Asn) |
| 51 | 0.833854 | (Gln+Lys)/(Arg+Val+Pro)+(Cit+Met)/(Asn) |
| 52 | 0.833842 | (Glu+Met)/(Asn)+(Gln+Gly)/(Val+Thr) |
| 53 | 0.833767 | (Gln)/(Arg+Val+Orn+Thr)+(Cit+Met)/(Asn) |
| 54 | 0.833754 | (Glu+Met)/(Asn)+(Gln+Gly)/(Val+Thr+ABA) |
| 55 | 0.833741 | (Glu+Met)/(Asn)+(Gln+Gly)/(Val+Ser+ABA) |
| 56 | 0.83364 | (Met)/(ABA+Asn)+(Glu+Gln)/(LNAA+Thr+Ser) |
| 57 | 0.833602 | (Glu+Met)/(Asn)+(Gln+Lys+Gly)/(Val+Thr) |
| 58 | 0.833533 | (Gln)/(LNAA+Thr+Ser+ABA)+(Cit+Met)/(Asn) |
| 59 | 0.833526 | (Met)/(Asn)+(Glu+Gln+Cit)/(LNAA+Arg+Thr) |
| 60 | 0.833355 | (Met)/(Asn)+(Glu+Gln+Ile+Lys)/(LNAA+Ser) |
| 61 | 0.833326 | (Gln)/(LNAA+AAA+Thr+Ser)+(Met)/(ABA+Asn) |
| 62 | 0.833299 | (Glu+Gln)/(BCAA+Arg+Ser)+(Cit+Met)/(Asn) |
| 63 | 0.833199 | (Glu+Gln)/(LNAA+Thr+Ser)+(Cit+Met)/(Asn) |
| 64 | 0.833092 | (Gln)/(BCAA+Arg+Phe+Thr)+(Cit+Met)/(Asn) |
| 65 | 0.833054 | (Gln)/(Arg+Val+Thr+ABA)+(Cit+Met)/(Asn) |
| 66 | 0.83302 | (Met)/(Asn)+(Glu+Gln+Ile)/(AAA+Val+Ser) |
| 67 | 0.833001 | (Glu+Met)/(Asn)+(Gln+Tyr+Gly)/(Val+Ser) |
| 68 | 0.832974 | (Gln)/(Arg+Val+Phe+Thr)+(Cit+Met)/(Asn) |

FIG.61

| RANK | VALUE | FORMULA |
|---|---|---|
| 69 | 0.832924 | (Met)/(Asn)+(Glu+Gln)/(BCAA+Orn+Thr+Ser) |
| 70 | 0.832923 | (Gln)/(Arg+Val+Trp+Ser)+(Cit+Met)/(Asn) |
| 71 | 0.832883 | (Glu+Gln)/(LNAA+Arg+Pro)+(Cit+Met)/(Asn) |
| 72 | 0.832853 | (Gln)/(Val+Pro+Phe+Thr)+(Cit+Met)/(Asn) |
| 73 | 0.832809 | (Gln+Tyr)/(AAA+Arg+Val)+(Cit+Met)/(Asn) |
| 74 | 0.832753 | (Met)/(ABA+Asn)+(Glu+Gln)/(LNAA+AAA+Ser) |
| 75 | 0.832674 | (Met)/(Asn)+(Glu+Gln+Cit)/(LNAA+Phe+Thr) |
| 76 | 0.832656 | (Cit+Met)/(Asn)+(Glu+Gln+Lys)/(LNAA+Thr) |
| 77 | 0.832648 | (Gln+Lys)/(BCAA+Thr+Ser)+(Cit+Met)/(Asn) |
| 78 | 0.832618 | (Met)/(Asn)+(Glu+Gln)/(AAA+Val+Thr+Ser) |
| 79 | 0.832597 | (Glu+Cit+Met)/(Asn)+(Gln+Ile+Leu)/(Val) |
| 80 | 0.832529 | (Gln)/(AAA+Arg+Val+Phe)+(Cit+Met)/(Asn) |
| 81 | 0.832504 | (Met)/(Asn)+(Glu+Gln)/(BCAA+His+Thr+Ser) |
| 82 | 0.832487 | (Met)/(Asn)+(Glu+Gln+Leu)/(LNAA+Thr+Ser) |
| 83 | 0.832365 | (Gln+Lys)/(LNAA+Thr+ABA)+(Cit+Met)/(Asn) |
| 84 | 0.832356 | (Glu+Gln)/(BCAA+His+Thr)+(Cit+Met)/(Asn) |
| 85 | 0.832352 | (Gln+Ile)/(Val)+(Glu+Cit+Met)/(Asn) |
| 86 | 0.83234 | (Glu+Gln)/(LNAA+Arg+ABA)+(Cit+Met)/(Asn) |
| 87 | 0.832319 | (Met)/(Asn)+(Glu+Gln)/(BCAA+Thr+Ser) |
| 88 | 0.832315 | (Gln)/(Arg+Val+Pro+Ser)+(Cit+Met)/(Asn) |
| 89 | 0.832297 | (Glu+Gln)/(Val+His+Thr)+(Cit+Met)/(Asn) |
| 90 | 0.832292 | (Glu+Cit+Met)/(Asn)+(Gln+Tyr+Leu)/(Val) |
| 91 | 0.832197 | (Gln)/(Arg+Val+Pro+Phe)+(Cit+Met)/(Asn) |
| 92 | 0.832196 | (Gln)/(LNAA+Phe+Thr+Ser)+(Met)/(ABA+Asn) |
| 93 | 0.832171 | (Cit+Met)/(Asn)+(Glu+Gln+Leu)/(LNAA+Thr) |
| 94 | 0.832159 | (Gln+Lys)/(Arg+Val+Thr)+(Cit+Met)/(Asn) |
| 95 | 0.832025 | (Glu+Gln)/(BCAA+Arg+Orn)+(Cit+Met)/(Asn) |
| 96 | 0.831967 | (Met)/(ABA+Asn)+(Glu+Gln)/(LNAA+Pro+Ser) |
| 97 | 0.831951 | (Met)/(Asn)+(Glu+Gln+Ile+Leu)/(LNAA+Ser) |
| 98 | 0.831864 | (Gln+Ala)/(LNAA+Pro+Thr)+(Cit+Met)/(Asn) |
| 99 | 0.831831 | (Gln+Lys)/(LNAA+Pro+Ser)+(Cit+Met)/(Asn) |
| 100 | 0.831734 | (Gln+Ile)/(Val+ABA)+(Glu+Cit+Met)/(Asn) |

STRESS EVALUATING APPARATUS, METHOD, SYSTEM AND PROGRAM AND RECORDING MEDIUM THEREFOR

This application is a Continuation of PCT/JP2007/065139, filed Aug. 2, 2007, which claims priority from Japanese patent application JP 2006-213918, filed Aug. 4, 2006.

BACKGROUND OF THE INVENTION

1. Field of the Invention

The present invention relates to a method of evaluating stress by utilizing the concentration of amino acids in blood (plasma), as well as a stress-evaluating apparatus, a stress-evaluating method, a stress-evaluating system, a stress-evaluating program and a recording medium.

2. Description of the Related Art

It is known that when physical and mental adaptation to environmental changes, human relations and fatigue is difficult, stress is caused and there occur various symptoms such as imbalanced lifestyle habit and eating disorder. Such symptoms are estimated as the origin of lifestyle-related diseases such as obesity, hypertension, hyperlipidemia and diabetes mellitus, and how stress is early noticed and coped with is an important task for preventing lifestyle-related diseases.

In diagnosis (stress finding) of mental disorders caused by stress, an interview sheet is widely used and includes ICD-10 (International Classification of Diseases, $10^{th}$ edition) prepared by World Health Organization (WHO) and DSM-IV (Diagnostic and Statistical Manual of Mental Disorders) prepared by American Psychiatric Association (APA).

The method of objectively measuring stress includes an electrophysiological method of measuring brain waves and heart rates (see Japanese Patent No. 3070346) and biochemical methods of measuring stress protein (see Japanese Patent No. 3429043 and Japanese Patent No. 3445038) and expression of various genes (see JP-A-2003-274949, JP-A-2004-208547, JP-A-2005-143420, JP-A-2005-312435 and JP-A-2006-15).

In addition, it is known that resistance to stress is enhanced when amino acids are ingested (see WO2005/07408), and that the concentrations of amino acids in blood vary under stress.

In plasma from patients with major depressive illness, Altamura C et al. (see "Altamura C, Maes M, Dai J, Meltzer H Y (1995) Eur Neuropsychopharmacol.5. Suppl 71-5.") show that the concentrations of taurine, serine/glycine are increased and the concentration of glycine is decreased; Mitani H et al. (see "Mitani H, Shirayama Y, Yamada T, Maeda K, Ashby C R Jr, Kawahara R (2006) Prog Neuropsychopharmacol Biol Psychiatry. 30(6). 1155-8.") show that the concentrations of taurine, glycine, glutamine and glutaric acid are increased; Mauri M C et al. (see "Mauri M C, Ferrara A, Boscati L, Bravin S, Zamberlan F, Alecci M, Invernizzi G (1998) Neuropsychobiology. 37(3).124-9." and "Mauri M C, Boscati L, Volonteri L S, Scalvini M E, Steinhilber C P, Laini V, Zamberlan F (2001) Neuropsychobiology. 44(3).134-8.") show the concentrations of lysine, taurine, glutamic acid, tyrosine/LNAAs (the sum total of valine, leucine, isoleucine, tyrosine and phenylalanine) are increased and the concentration of tryptophan/LNAAs is decreased; and Kishimoto (see "Eiji Kishimoto (1993), Medicine of Brain and Sprit, Vol. 4, No. 2, April, 1993") shows that the concentrations of tryptophan, tyrosine, lysine, leucine, isoleucine, phenylalanine, methionine, alanine, glutamic acid, arginine and histidine are decreased.

In addition, Altamura C et al. (see Nonpatent Literature 1) show that major depressive illness can be discriminated by a linear discriminant using glycine, glutamic acid and taurine, and Mauri M C et al. (Nonpatent Literatures 3 and 4) show that tyrosine/LNAAs, tryptophan/LNAAs, can serve as indicators of the pharmaceutical effect of an antidepressant.

However, the results in the interview sheet used in finding and diagnosis of stress are often subject to a subject's subjectivity, which causes a problem of reduced accuracy in the results in the interview sheet.

For extracting stress evidence by highly accurate diagnosis, an index capable of objectively diagnosing stress without a subject's subjectivity has been desired. However, in the methods of measuring brain waves and heart rates, stress protein or expression of various genes among the methods of objectively diagnosing stress as described above, there is a problem that measurement of the diagnostic index and interpretation of measurement results are difficult and measuring instruments used therein are poor in general versatility so that these methods are not widely accepted.

SUMMARY OF THE INVENTION

It is an object of the present invention to at least partially solve the problems in the conventional technology. The present invention was made in view of the problems described above, and for example, an object of the present invention is to provide a method of accurately evaluating a state of stress by utilizing the concentrations of amino acids which among amino acids in blood, are related to a state of stress, as well as a stress-evaluating apparatus, a stress-evaluating method, a stress-evaluating system, a stress-evaluating program and a recording medium.

The present inventors made extensive study for solving the problem, and as a result, they identified amino acid variables useful for discrimination between states under stress loading by the concentrations of amino acids in blood, and found that a correlation equation (index) using the amino acid variables correlates significantly with mental diseases based on stress finding, particularly with the progress of depressive illness, and the present invention was thereby completed. Specifically, the present inventors paid attention to a difference between the amino acid concentration in plasma from healthy subjects and the amino acid concentration in plasma from those with finding of stress, and they developed an index for objectively and accurately diagnosing stress by measuring the amino acid concentration in plasma. The amino acids in plasma can be measured inexpensively, rapidly and easily and will highly possibly be distributed as a diagnostic index to solve the problem of the method of objectively measuring stress. The present invention encompasses the following:

To solve the problem and achieve the object described above, a method of evaluating stress according to the present invention includes a measuring step of measuring amino acid concentration data on the concentration value of amino acid in blood collected from a subject to be examined, and a concentration value criterion evaluating step of evaluating a stress state including at least depressive illness and major depressive illness in the subject, based on the concentration value of at least one of Lys, His, ABA (ABA is α-ABA (aminobutyric acid)), Asn, Phe, Leu, Ile, Val, Trp, Tyr and Met contained in the amino acid concentration data of the subject measured at the measuring step.

Another aspect of the present invention is the method of evaluating stress, wherein the concentration value criterion evaluating step further includes a concentration value criterion discriminating step of discriminating between depressive illness and non-depressive illness or between major depressive illness and non-major depressive illness in the subject, based on the concentration value of at least one of Lys, His, ABA, Asn, Phe, Leu, Ile, Val, Trp, Tyr and Met contained in the amino acid concentration data of the subject measured at the measuring step.

Still another aspect of the present invention is the method of evaluating stress, wherein the concentration criterion evaluating step further includes a discriminant value calculating step of calculating a discriminant value that is a value of multivariate discriminant, based on both the concentration value of at least one of Lys, His, ABA, Asn, Phe, Leu, Ile, Val, Trp, Tyr and Met contained in the amino acid concentration data of the subject measured at the measuring step and a previously established multivariate discriminant with the concentration of the amino acid as variable, and a discriminant value criterion evaluating step of evaluating the stress state in the subject, based on the discriminant value calculated at the discriminant value calculating step, and the multivariate discriminant contains at least one of Lys, His, ABA, Asn, Phe, Leu, Ile, Val, Trp, Tyr and Met as the variable.

Still another aspect of the present invention is the method of evaluating stress, wherein the discriminant value criterion evaluating step further includes a discriminant value criterion discriminating step of discriminating between depressive illness and non-depressive illness or between major depressive illness and non-major depressive illness in the subject based on the discriminant value calculated at the discriminant value calculating step, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating stress, wherein the multivariate discriminant in discriminating between depressive illness and non-depressive illness at the discriminant value criterion discriminating step is formula 1 or 2 below, or a logistic regression equation with Ser, Glu, Cys and Lys as variables or a linear discriminant with Ser, Glu, Cys and Lys as variables.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

Still another aspect of the present invention is the method of evaluating stress, wherein the multivariate discriminant in discriminating between major depressive illness and non-major depressive illness at the discriminant value criterion discriminating step is:

formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

The present invention also relates to a stress-evaluating apparatus. One aspect of the present invention is a stress-evaluating apparatus including a control unit and a memory unit to evaluate a stress state including at least depressive illness and major depressive illness in a subject to be evaluated, wherein the control unit includes a discriminant value-calculating unit that calculates a discriminant value that is a value of multivariate discriminant, based on both the concentration value of at least one of Lys, His, ABA, Asn, Phe, Leu, Ile, Val, Trp, Tyr and Met contained in previously obtained amino acid concentration data on the concentration value of amino acid in the subject and a multivariate discriminant with the concentration of the amino acid as variable stored in the memory unit, and a discriminant value criterion-evaluating unit that evaluates the stress state in the subject, based on the discriminant value calculated by the discriminant value-calculating unit, and the multivariate discriminant contains at least one of Lys, His, ABA, Asn, Phe, Leu, Ile, Val, Trp, Tyr and Met as the variable.

Another aspect of the present invention is the stress-evaluating apparatus, wherein the discriminant value criterion-evaluating unit further includes a discriminant value criterion-discriminating unit that discriminates between depressive illness and non-depressive illness or between major depressive illness in the subject based on the discriminant value calculated by the discriminant value-calculating unit, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the stress-evaluating apparatus, wherein the multivariate discriminant in the discriminant value criterion-discriminating unit discriminating between depressive illness and non-depressive illness is formula 1 or 2 below, or a logistic regression equation with Ser, Glu, Cys and Lys as variables or a linear discriminant with Ser, Glu, Cys and Lys as variables.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

Still another aspect of the present invention is the stress-evaluating apparatus, wherein the multivariate discriminant in the discriminant value criterion-discriminating unit discriminating between major depressive illness and non-major depressive illness is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Still another aspect of the present invention is the stress-evaluating apparatus, wherein the control unit further includes a multivariate discriminant-preparing unit that prepares the multivariate discriminant to be stored in the memory unit, based on stress state information containing the amino acid concentration data and stress state index data on an index for indicating the stress state, stored in the memory unit, the multivariate discriminant-preparing unit further includes a candidate multivariate discriminant-preparing unit that prepares a candidate multivariate discriminant that is a candidate of the multivariate discriminant, based on a predetermined discriminant-preparing method from the stress state information, a candidate multivariate discriminant-verifying unit that verifies the candidate multivariate discriminant prepared by the candidate multivariate discriminant-preparing unit, based on a predetermined verifying method, and a variable-selecting unit that selects a variable of the candidate multivariate discriminant based on a predetermined variable-selecting method from the verification result obtained by the candidate multivariate discriminant-verifying unit, thereby selecting a combination of the amino acid concentration data contained in the stress state information used in preparing the candidate multivariate discriminant, and the multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the variable-selecting unit.

The present invention also relates to a stress-evaluating method. One aspect of the present invention is the stress-evaluating method of evaluating a stress state including at least depressive illness and major depressive illness in a subject to be evaluated which is carried out with an information processing apparatus including a control unit and a memory unit, the method including a discriminant value calculating step of calculating a discriminant value that is a value of multivariate discriminant, based on both the concentration value of at least one of Lys, His, ABA, Asn, Phe, Leu, Ile, Val, Trp, Tyr and Met contained in previously obtained amino acid concentration data on the concentration value of amino acid in the subject and a multivariate discriminant with the concentration of the amino acid as variable stored in the memory unit, and a discriminant value criterion evaluating step of evaluating the stress state in the subject, based on the discriminant value calculated at the discriminant value calculating step, that are executed by the control unit, and the multivariate discriminant contains at least one of Lys, His, ABA, Asn, Phe, Leu, Ile, Val, Trp, Tyr and Met as the variable.

Another aspect of the present invention is the stress-evaluating method, wherein the discriminant value criterion evaluating step further includes a discriminant value criterion discriminating step of discriminating between depressive illness and non-depressive illness or between major depressive and non-major depressive illness in the subject based on the discriminant value calculated at the discriminant value calculating step, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the stress-evaluating method, wherein the multivariate discriminant in discriminating between depressive illness and non-depressive illness at the discriminant value criterion discriminating step is formula 1 or 2 below, or a logistic regression equation with Ser, Glu, Cys and Lys as variables or a linear discriminant with Ser, Glu, Cys and Lys as variables.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

Still another aspect of the present invention is the stress-evaluating method, wherein the multivariate discriminant in discriminating between major depressive illness and non-major depressive illness at the discriminant value criterion discriminating step is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Still another aspect of the present invention is the stress-evaluating method, wherein the method further includes a multivariate discriminant preparing step of preparing the multivariate discriminant to be stored in the memory unit, based on stress state information containing the amino acid concentration data and stress state index data on an index for indicating the stress state, stored in the memory unit, that is executed by the control unit, the multivariate discriminant preparing step further includes a candidate multivariate discriminant preparing step of preparing a candidate multivariate discriminant that is a candidate of the multivariate discriminant, based on a predetermined discriminant-preparing method from the stress state information, a candidate multivariate discriminant verifying step of verifying the candidate multivariate discriminant prepared at the candidate multivariate discriminant preparing step, based on a predetermined verifying method, and a variable selecting step of selecting a variable of the candidate multivariate discriminant based on a predetermined variable-selecting method from the verification result obtained at the candidate multivariate discriminant verifying step, thereby selecting a combination of the amino acid concentration data contained in the stress state information used in preparing the candidate multivariate discriminant, and at the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the variable selecting step.

The present invention also relates to a stress-evaluating system. One aspect of the present invention is the stress-evaluating system, including a stress-evaluating apparatus having a control unit and a memory unit to evaluate a stress state including at least depressive illness and major depressive illness in a subject to be evaluated, and an information communication terminal apparatus that provides amino acid concentration data on the concentration value of amino acid in the subject connected to each other communicatively via a network, the information communication terminal apparatus including an amino acid concentration data-sending unit that transmits the amino acid concentration data of the subject to the stress-evaluating apparatus, and an evaluation result-receiving unit that receives the evaluation result of the stress state of the subject transmitted from the stress-evaluating apparatus, the control unit of the stress-evaluating apparatus including an amino acid concentration data-receiving unit that receives the amino acid concentration data of the subject transmitted from the information communication terminal apparatus, a discriminant value-calculating unit that calculates a discriminant value that is a value of multivariate discriminant, based on both the concentration value of at least one of Lys, His, ABA, Asn, Phe, Leu, Ile, Val, Trp, Tyr and Met contained in the amino acid concentration data of the subject received by the amino acid concentration data-receiving unit and a multivariate discriminant with the concentration of the amino acid as variable stored in the memory unit, a discriminant value criterion-evaluating unit that evaluates the stress state in the subject, based on the discriminant value calculated by the discriminant value-calculating unit, and an evaluation result-sending unit that transmits the evaluation result of the subject obtained by the discriminant value criterion-evaluating unit to the information communication terminal apparatus, and the multivariate discriminant contains at least one of Lys, His, ABA, Asn, Phe, Leu, Ile, Val, Trp, Tyr and Met as the variable.

Another aspect of the present invention is the stress-evaluating system, wherein the discriminant value criterion-evaluating unit further includes a discriminant value criterion-discriminating unit that discriminates between depressive illness and non-depressive illness or between major depressive illness in the subject based on the discriminant value calculated by the discriminant value-calculating unit, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the stress-evaluating system, wherein the multivariate discriminant in the discriminant value criterion-discriminating unit discriminating between depressive illness and non-depressive illness is formula 1 or 2 below, or a logistic regression equation with Ser, Glu, Cys and Lys as variables or a linear discriminant with Ser, Glu, Cys and Lys as variables.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

Still another aspect of the present invention is the stress-evaluating system, wherein the multivariate discriminant in the discriminant value criterion-discriminating unit discriminating between major depressive illness and non-major depressive illness is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Still another aspect of the present invention is the stress-evaluating system, wherein the control unit of the stress-evaluating apparatus further includes a multivariate discriminant-preparing unit that prepares the multivariate discriminant to be stored in the memory unit, based on stress state information containing the amino acid concentration data and stress state index data on an index for indicating the stress state, stored in the memory unit, the multivariate discriminant-preparing unit further includes a candidate multivariate discriminant-preparing unit that prepares a candidate multivariate discriminant that is a candidate of the multivariate discriminant, based on a predetermined discriminant-preparing method from the stress state information, a candidate multivariate discriminant-verifying unit that verifies the candidate multivariate discriminant prepared by the candidate multivariate discriminant-preparing unit, based on a predetermined verifying method, and a variable-selecting unit that selects a variable of the candidate multivariate discriminant based on a predetermined variable-selecting method from the verification result obtained by the candidate multivariate discriminant-verifying unit, thereby selecting a combination of the amino acid concentration data contained in the stress state information used in preparing the candidate multivariate discriminant, and the multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the variable-selecting unit.

The present invention also relates to a stress-evaluating program. One aspect of the present invention is the stress-evaluating program that makes an information processing apparatus including a control unit and a memory unit execute a method of evaluating a stress state including at least depressive illness and major depressive illness in a subject to be evaluated, the method including a discriminant value calculating step of calculating a discriminant value that is a value of multivariate discriminant, based on both the concentration value of at least one of Lys, His, ABA, Asn, Phe, Leu, Ile, Val, Trp, Tyr and Met contained in previously obtained amino acid concentration data on the concentration value of amino acid in the subject and a multivariate discriminant with the concentration of the amino acid as variable stored in the memory unit, and a discriminant value criterion evaluating step of evaluating the stress state in the subject, based on the discriminant value calculated at the discriminant value calculating step, that are executed by the control unit, and the multivariate discriminant contains at least one of Lys, His, ABA, Asn, Phe, Leu, Ile, Val, Trp, Tyr and Met as the variable.

Another aspect of the present invention is the stress-evaluating program, wherein the discriminant value criterion evaluating step further includes a discriminant value criterion discriminating step of discriminating between depressive illness and non-depressive illness or between major depressive and non-major depressive illness in the subject based on the discriminant value calculated at the discriminant value calculating step, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the stress-evaluating program, wherein the multivariate discriminant in discriminating between depressive illness and non-depressive illness at the discriminant value criterion discriminating step is formula 1 or 2 below, or a logistic regression equation with Ser, Glu, Cys and Lys as variables or a linear discriminant with Ser, Glu, Cys and Lys as variables.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

Still another aspect of the present invention is the stress-evaluating program, wherein the multivariate discriminant in discriminating between major depressive illness and non-major depressive illness at the discriminant value criterion discriminating step is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Still another aspect of the present invention is the stress-evaluating program, wherein the method further includes a multivariate discriminant preparing step of preparing the multivariate discriminant to be stored in the memory unit, based on stress state information containing the amino acid concentration data and stress state index data on an index for indicating the stress state, stored in the memory unit, that is executed by the control unit, the multivariate discriminant preparing step further includes a candidate multivariate discriminant preparing step of preparing a candidate multivariate discriminant that is a candidate of the multivariate discriminant, based on a predetermined discriminant-preparing method from the stress state information, a candidate multivariate discriminant verifying step of verifying the candidate multivariate discriminant prepared at the candidate multivariate discriminant preparing step, based on a predetermined verifying method, and a variable-selecting unit that selects a variable of the candidate multivariate discriminant based on a predetermined variable-selecting method from the verification result obtained at the candidate multivariate discriminant verifying step, thereby selecting a combination of the amino acid concentration data contained in the stress state information used in preparing the candidate multivariate discriminant, and at the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the variable selecting step.

The present invention also relates to a recording medium. One aspect of the computer-readable recording medium including the stress-evaluating program recorded thereon.

EFFECTS OF THE INVENTION

According to the method of evaluating stress of the present invention, amino acid concentration data on the concentration value of amino acid in blood collected from a subject to be evaluated is measured, and a stress state in the subject is evaluated based on the concentration value of at least one of Lys, His, ABA, Asn, Phe, Leu, Ile, Val, Trp, Tyr and Met contained in the measured amino acid concentration data of the subject. Thus, the concentrations of the amino acids which among amino acids in blood, are related to a stress state can be utilized to bring about an effect of enabling accurate evaluation of a stress state.

According to the method of evaluating stress of the present invention, discrimination between depressive illness and non-depressive illness or between major depressive illness and non-major depressive illness in the subject is conducted based on the concentration value of at least one of Lys, His, ABA, Asn, Phe, Leu, Ile, Val, Trp, Tyr and Met contained in the amino acid concentration data of the subject measured. Thus, the concentrations of the amino acids which among amino acids in blood, are useful for discriminating between depressive illness and non-depressive illness or between major depressive illness and non-major depressive illness can be utilized to bring about an effect of enabling accurate discrimination between the 2 groups of depressive illness and non-depressive illness or between the 2 groups of major depressive illness and non-major depressive illness.

According to the method of evaluating stress of the present invention, a discriminant value that is a value of multivariate discriminant is calculated based on both the concentration value of at least one of Lys, His, ABA, Asn, Phe, Leu, Ile, Val, Trp, Tyr and Met contained in the amino acid concentration data of the subject measured and a previously established multivariate discriminant with the concentration of the amino acid of at least one of Lys, His, ABA, Asn, Phe, Leu, Ile, Val, Trp, Tyr and Met as the variable, and the stress state in the subject is evaluated based on the discriminant value calculated. Thus, a discriminant value obtained in a multivariate discriminant wherein the concentrations of amino acids which among amino acids in blood, are related to a stress state are variables can be utilized to bring about an effect of enabling accurate evaluation of a stress state.

According to the method of evaluating stress of the present invention, discrimination between depressive illness and non-depressive illness or between major depressive illness and non-major depressive illness in the subject is conducted based on the discriminant value calculated, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant (e.g., fractional expression) using amino acid variables useful for discriminating between the 2 groups of depressive illness and non-depressive illness or between the 2 groups of major depressive illness and non-major depressive illness can be utilized to bring about an effect of enabling more accurate discrimination between the 2 groups of depressive illness and non-depressive illness or between the 2 groups of major depressive illness and non-major depressive illness.

According to the method of evaluating stress of the present invention, the multivariate discriminant in discriminating between depressive illness and non-depressive illness is formula 1 or 2 below, or a logistic regression equation with Ser, Glu, Cys and Lys as variables or a linear discriminant with Ser, Glu, Cys and Lys as variables. Thus, a discriminant value obtained in a multivariate discriminant useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

According to the method of evaluating stress of the present invention, the multivariate discriminant in discriminating between major depressive illness and non-major depressive illness is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

According to the stress-evaluating apparatus, the stress-evaluating method and the stress-evaluating program of the present invention, a discriminant value that is a value of multivariate discriminant is calculated based on both the concentration value of at least one of Lys, His, ABA, Asn, Phe, Leu, Ile, Val, Trp, Tyr and Met contained in previously obtained amino acid concentration data of the subject and multivariate discriminant with the concentration of the amino acid of at least one of Lys, His, ABA, Asn, Phe, Leu, Ile, Val, Trp, Tyr and Met as variable, stored in the memory unit, and a stress state including at least depressive illness and major depressive illness in the subject is evaluated based on the discriminant value calculated. Thus, a discriminant value obtained in a multivariate discriminant wherein the concentrations of amino acids which among amino acids in blood, are related to a stress state are variables can be utilized to bring about an effect of enabling accurate evaluation of a stress state.

According to the stress-evaluating apparatus, the stress-evaluating method and the stress-evaluating program of the present invention, discrimination between depressive illness and non-depressive illness or between major depressive illness and non-major depressive illness in the subject is conducted based on the discriminant value calculated, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant (e.g., fractional expression) using amino acid variables useful for discriminating between the 2 groups of depressive illness and non-depressive illness or between the 2 groups of major depressive illness and non-major depressive illness can be utilized to bring about an effect of enabling more accurate discrimination between the 2 groups of depressive illness and non-depressive illness or between the 2 groups of major depressive illness and non-major depressive illness.

According to the stress-evaluating apparatus, the stress-evaluating method and the stress-evaluating program of the present invention, the multivariate discriminant in discriminating between depressive illness and non-depressive illness is formula 1 or 2 below, or a logistic regression equation with Ser, Glu, Cys and Lys as variables or a linear discriminant with Ser, Glu, Cys and Lys as variables. Thus, a discriminant value obtained in a multivariate discriminant using amino acid variables useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

According to the stress-evaluating apparatus, the stress-evaluating method and the stress-evaluating program of the present invention, the multivariate discriminant in discriminating between major depressive illness and non-major depressive illness is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

According to the stress-evaluating apparatus, the stress-evaluating method and the stress-evaluating program of the present invention, a multivariate discriminant to be stored in a memory unit is prepared based on the stress state information stored in the memory unit, including amino acid concentration data and stress state index data on an index for indicating a stress state. Specifically, (1) a candidate multivariate discriminant that is a candidate of multivariate discriminant is prepared from the stress state information, according to a predetermined discriminant-preparing method, (2) the prepared candidate multivariate discriminant is verified based on a predetermined verification method, (3) based on a predetermined variable-selecting method, variables in the candidate multivariate discriminant are selected from the verification results in (2), thereby selecting a combination of amino acid concentration data contained in the stress state information used in preparing of a candidate multivariate discriminant, and (4) based on verification results accumulated by executing (1), (2) and (3) repeatedly, a candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a stress state (specifically a multivariate discriminant correlating significantly with a stress state (more specifically, a multivariate discriminant useful for discrimination of the 2 groups of depressive illness and non-depressive illness, a multivariate discriminant useful for discrimination of the 2 groups of major depressive illness and non-major depressive illness).

According to the stress-evaluating system of the present invention, the information communication terminal apparatus first transmits amino acid concentration data of a subject to be evaluated to the stress-evaluating apparatus. The stress-evaluating apparatus receives the amino acid concentration data of the subject transmitted from the information communication terminal apparatus, calculates a discriminant value that is the value of the multivariate discriminant based on both the concentration value of at least one of Lys, His, ABA, Asn, Phe, Leu, Ile, Val, Trp, Tyr and Met contained in the received amino acid concentration data of the subject and the multivariate discriminant with amino acid concentration as variable stored in the memory unit, where the concentration value of at least one of Lys, His, ABA, Asn, Phe, Leu, Ile, Val, Trp, Tyr and Met is contained as a variable, and evaluates the stress state in the subject based on the calculated discriminant value, and transmits the evaluation result of the subject to the information communication terminal apparatus. Then, the information communication terminal apparatus receives the evaluation result of the subject concerning the stress state transmitted from the stress-evaluating apparatus. Thus, a discriminant value obtained in a multivariate discriminant wherein the concentrations of amino acids which among amino acids in blood, are related to a stress state are variables can be utilized to bring about an effect of enabling accurate evaluation of a stress state.

According to the stress-evaluating system of the present invention, discrimination between depressive illness and non-depressive illness or between major depressive illness and non-major depressive illness in the subject is conducted based on the discriminant value calculated, and the multivariate discriminant is expressed by one fractional expression or the sum of a plurality of the fractional expressions and contains at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant (e.g., fractional expression) using amino acid variables useful for discriminating between the 2 groups of depressive illness and non-depressive illness or between the 2 groups of major depressive illness and non-major depressive illness can be utilized to bring about an effect of enabling more accurate discrimination between the 2 groups of depressive illness and non-depressive illness or between the 2 groups of major depressive illness and non-major depressive illness.

According to the stress-evaluating system of the present invention, the multivariate discriminant in discriminating between depressive illness and non-depressive illness is formula 1 or 2 below, or a logistic regression equation with Ser, Glu, Cys and Lys as variables or a linear discriminant with Ser, Glu, Cys and Lys as variables. Thus, a discriminant value obtained in a multivariate discriminant useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

According to the stress-evaluating system of the present invention, the multivariate discriminant in discriminating between major depressive illness and non-major depressive illness is formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

According to the stress-evaluating system of the present invention, a multivariate discriminant to be stored in a memory unit is prepared based on the stress state information stored in the memory unit, including amino acid concentration data and stress state index data on an index for indicating a stress state. Specifically, (1) a candidate multivariate discriminant that is a candidate of multivariate discriminant is prepared from the stress state information, according to a predetermined discriminant-preparing method, (2) the prepared candidate multivariate discriminant is verified based on a predetermined verification method, (3) based on a predetermined variable-selecting method, variables in the candidate multivariate discriminant are selected from the verification results in (2), thereby selecting a combination of amino acid concentration data contained in the stress state information used in preparing of a candidate multivariate discriminant, and (4) based on verification results accumulated by executing (1), (2) and (3) repeatedly, a candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a stress state (specifically a multivariate discriminant correlating significantly with a stress state (more specifically, a multivariate discriminant useful for discrimination of the 2 groups of depressive illness and non-depressive illness, a multivariate discriminant useful for discrimination of the 2 groups of major depressive illness and non-major depressive illness).

According to the recording medium of the present invention, the stress-evaluating program recorded on the recording medium is read and executed by the computer, thereby allowing the computer to execute the stress-evaluating program, thus bringing about an effect of obtaining the same effect as in the stress-evaluating program.

When a state of stress is evaluated (specifically discrimination between depressive illness and non-depressive illness or discrimination between major depressive illness and non-major depressive illness is conducted) in the present invention, the concentrations of other metabolites (biological metabolites), metabolome data (organic acid, fatty acid, nucleic acid etc.), transcriptome data, proteome data, the protein expression level, the age and sex of the subject, biological indices, or the like may be used in addition to the amino acid concentration data. When a state of stress is evaluated (specifically discrimination between depressive illness and non-depressive illness or discrimination between major depressive illness and non-major depressive illness is conducted) in the present invention, the concentrations of other metabolites (biological metabolites), metabolome data (organic acid, fatty acid, nucleic acid etc.), transcriptome data, proteome data, the protein expression level, the age and sex of the subject, biological indices or the like may be used as variables in the multivariate discriminant in addition to the amino acid concentration data.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of the information stored in the user information file 106*a*;

FIG. 8 is a chart showing an example of the information stored in the amino acid concentration data file 106*b*;

FIG. 9 is a chart showing an example of the information stored in the stress state information file 106*c*;

FIG. 10 is a chart showing an example of the information stored in the designated stress state information file 106*d*;

FIG. 11 is a chart showing an example of the information stored in the candidate multivariable discriminant file 106*e*1;

FIG. 12 is a chart showing an example of the information stored in the verification result file 106*e*2;

FIG. 13 is a chart showing an example of the information stored in the selected stress state information file 106*e*3;

FIG. 14 is a chart showing an example of the information stored in the multivariable discriminant file 106*e*4;

FIG. 15 is a chart showing an example of the information stored in the discriminant value file 106*f*;

FIG. 24 is a chart showing a plurality of indices having performance equivalent to the logistic regression equation shown in Example 2, which maximizes the performance of discriminating the 2 groups of a healthy group and a group with finding of depressive illness;

FIG. 25 is a chart showing a plurality of indices having performance equivalent to the logistic regression equation shown in Example 2, which maximizes the performance of discriminating the 2 groups of a healthy group and a group with finding of depressive illness;

FIG. 26 is a chart showing a plurality of indices having performance equivalent to the logistic regression equation shown in Example 2, which maximizes the performance of discriminating the 2 groups of a healthy group and a group with finding of depressive illness;

FIG. 28 is a chart showing a plurality of indices having performance equivalent to the logistic regression equation shown in Example 2, which maximizes the performance of discriminating the 2 groups of a healthy group and a group with finding of major depressive illness;

FIG. 29 is a chart showing a plurality of indices having performance equivalent to the logistic regression equation shown in Example 2, which maximizes the performance of discriminating the 2 groups of a healthy group and a group with finding of major depressive illness;

FIG. 30 is a chart showing a plurality of indices having performance equivalent to the logistic regression equation shown in Example 2, which maximizes the performance of discriminating the 2 groups of a healthy group and a group with finding of major depressive illness;

FIG. 32 is a chart showing a plurality of indices having performance equivalent to the linear discriminant shown in Example 2, which maximizes the performance of discriminating the 2 groups of a healthy group and a group with finding of depressive illness;

FIG. 33 is a chart showing a plurality of indices having performance equivalent to the linear discriminant shown in Example 2, which maximizes the performance of discriminating the 2 groups of a healthy group and a group with finding of depressive illness;

FIG. 34 is a chart showing a plurality of indices having performance equivalent to the linear discriminant shown in Example 2, which maximizes the performance of discriminating the 2 groups of a healthy group and a group with finding of depressive illness;

FIG. 36 is a chart showing a plurality of indices having performance equivalent to the linear discriminant shown in Example 2, which maximizes the performance of discriminating the 2 groups of a healthy group and a group with finding of major depressive illness;

FIG. 37 is a chart showing a plurality of indices having performance equivalent to the linear discriminant shown in Example 2, which maximizes the performance of discriminating the 2 groups of a healthy group and a group with finding of major depressive illness;

FIG. 38 is a chart showing a plurality of indices having performance equivalent to the linear discriminant shown in Example 2, which maximizes the performance of discriminating the 2 groups of a healthy group and a group with finding of major depressive illness;

FIG. 40 is a chart showing a list of indices having the same diagnostic performance as that of index 1;

FIG. 41 is a chart showing a list of indices having the same diagnostic performance as that of index 1;

FIG. 42 is a chart showing a list of indices having the same diagnostic performance as that of index 1;

FIG. 44 is a chart showing a list of indices having the same diagnostic performance as that of index 3;

FIG. 45 is a chart showing a list of indices having the same diagnostic performance as that of index 3;

FIG. 46 is a chart showing a list of indices having the same diagnostic performance as that of index 3;

FIG. 51 is a chart showing a plurality of indices having performance equivalent to the logistic regression equation shown in Example 7, which maximizes the performance of discriminating the 2 groups of a healthy group and a group with finding of major depressive illness;

FIG. 52 is a chart showing a plurality of indices having performance equivalent to the logistic regression equation shown in Example 7, which maximizes the performance of discriminating the 2 groups of a healthy group and a group with finding of major depressive illness;

FIG. 53 is a chart showing a plurality of indices having performance equivalent to the logistic regression equation shown in Example 7, which maximizes the performance of discriminating the 2 groups of a healthy group and a group with finding of major depressive illness;

FIG. 55 is a chart showing a plurality of indices having performance equivalent to the linear discriminant equation shown in Example 7, which maximizes the performance of discriminating the 2 groups of a healthy group and a group with finding of major depressive illness;

FIG. 56 is a chart showing a plurality of indices having performance equivalent to the linear discriminant equation shown in Example 7, which maximizes the performance of discriminating the 2 groups of a healthy group and a group with finding of major depressive illness;

FIG. 57 is a chart showing a plurality of indices having performance equivalent to the linear discriminant equation shown in Example 7, which maximizes the performance of discriminating the 2 groups of a healthy group and a group with finding of major depressive illness;

FIG. 59 is a chart showing a list of indices having the same diagnostic performance as that of index 7;

FIG. 60 is a chart showing a list of indices having the same diagnostic performance as that of index 7;

FIG. 61 is a chart showing a list of indices having the same diagnostic performance as that of index 7;

DETAILED DESCRIPTION OF THE PREFERRED EMBODIMENTS

Hereinafter, an embodiment (first embodiment) of the method of evaluating stress of the present invention and an embodiment (second embodiment) of the stress-evaluating apparatus, the stress-evaluating method, the stress-evaluating system, the stress-evaluating program and the recording medium of the present invention are described in detail with reference to the drawings. The present invention is not limited to these embodiments.

First Embodiment 1-1. Outline of the Invention

Figure 1:
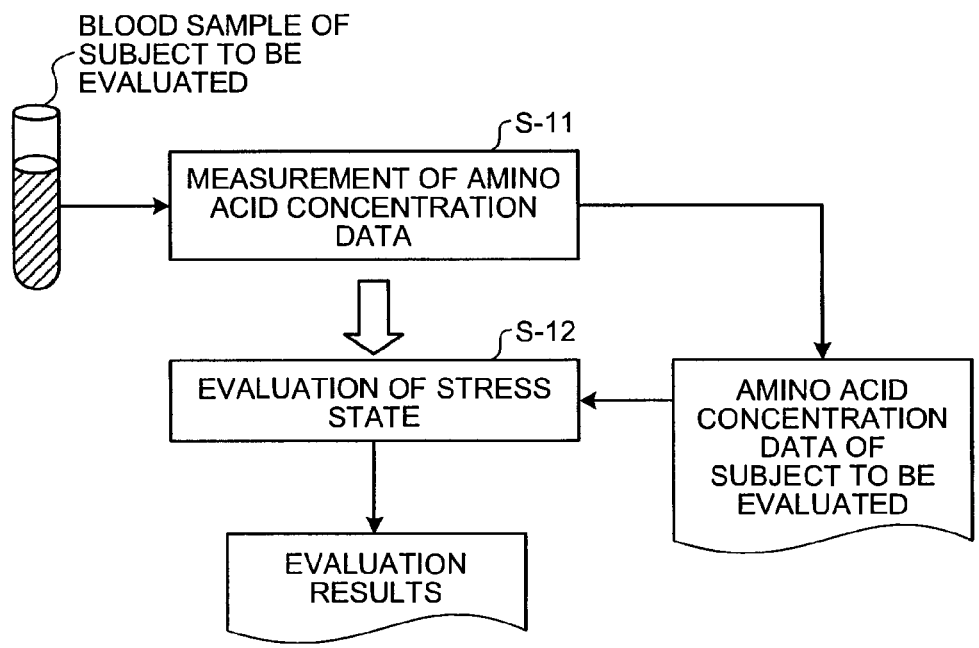
FIG. 1 is a principle configurational diagram showing the basic principle of the present invention.

Here, an outline of the method of evaluating stress of the present invention will be described with reference to FIG. 1. FIG. 1 is a principle configurational diagram showing the basic principle of the present invention.

In the present invention, the amino acid concentration data on concentration values of amino acids in blood collected from a subject (for example, an individual such as animal or human) to be evaluated are first measured (step S-11). The concentrations of amino acids in blood were analyzed in the following manner. A blood sample is collected in a heparin-treated tube, and then the blood plasma is separated by centrifugation of the collected blood sample. All blood plasma samples separated were frozen and stored at −70° C. before measurement of amino acid concentration. Before measurement of amino acid concentration, the blood plasma sample was deproteinized by adding sulfosalicylic acid to a concentration of 3%. An amino acid analyzer and a high-performance liquid chromatography/mass spectrometer (LC/MS) by high-performance liquid chromatography (HPLC) by using ninhydrin reaction in the post column were used for measurement of amino acid concentration. The unit of amino acid concentration is for example molar concentration or weight concentration, which may be subjected to addition, subtraction, multiplication and division by an arbitrary constant.

In the present invention, the stress state in a subject to be evaluated is evaluated based on at least one concentration value of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA (BCAA represents the sum of Val, Leu and Ile; this hereinafter applies), AAA (AAA represents the sum of Tyr, Phe and Trp; this hereinafter applies), and LNAAs (LNAAs represent the sum of Val, Leu, Ile, Tyr, Phe and Trp; this hereinafter applies)) contained in the amino acid concentration data of the subject to be evaluated measured in the step S-11 (step S-12).

According to the present invention described above, amino acid concentration data on the concentration value of amino acid in blood collected from a subject to be evaluated is measured, and a stress state in the subject is evaluated based on the concentration value of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) contained in the measured amino acid concentration data of the subject. Thus, the concentrations of the amino acids which among amino acids in blood, are related to a stress state can be utilized to bring about an effect of enabling accurate evaluation of a stress state.

Before step S-12 is executed, data such as defective and outliers may be removed from the amino acid concentration data of the subject to be evaluated measured in step S-11. Thereby, the state of stress can be more accurately evaluated.

In step S-12, discrimination between depressive illness and non-depressive illness or between major depressive illness and non-major depressive illness in the subject may be conducted based on the concentration value of at least one of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) contained in the amino acid concentration data of the subject measured in step S-11. Specifically, at least one concentration value of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) may be compared with a previously established threshold (cutoff value), thereby discriminating between depressive illness and non-depressive illness or between major depressive illness and non-major depressive illness in the subject. Thus, the concentrations of the amino acids which among amino acids in blood, are useful for discriminating between the 2 groups of depressive illness and non-depressive illness or between the 2 groups of major depressive illness and non-major depressive illness can be utilized to bring about an effect of enabling accurate discrimination between the 2 groups of depressive illness and non-depressive illness or between the 2 groups of major depressive illness and non-major depressive illness.

In step S-12, a discriminant value that is a value of multivariate discriminant is calculated based on both the concentration value of at least one of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) contained in the amino acid concentration data of the subject measured in step S-11 and a previously established multivariate discriminant with the concentration of the amino acid of at least one of Lys, His, ABA, Asn, Phe, Leu, Ile, Val, Trp, Tyr and Met (for example, at least one of Lys, His, ABA, Asn, Phe, Leu, Ile, Val, Trp, Tyr, Met, BCAA, AAA, and LNAAs) as the variable, and the stress state in the subject may be evaluated based on the discriminant value calculated. Thus, a discriminant value obtained in a multivariate discriminant wherein the concentrations of amino acids which among amino acids in blood, are related to a stress state are variables can be utilized to bring about an effect of enabling accurate evaluation of a stress state.

In step S-12, discrimination between depressive illness and non-depressive illness or between major depressive illness and non-major depressive illness in the subject may be conducted based on the discriminant value calculated. Specifically, the discriminant value calculated may be compared with a previously established threshold (cutoff value), thereby discriminating between depressive illness and non-depressive illness or between major depressive illness and non-major depressive illness in the subject. The multivariate discriminant may be expressed by one fractional expression or the sum of a plurality of the fractional expressions and may contain at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant (e.g., fractional expression) using amino acid variables useful for discriminating between the 2 groups of depressive illness and non-depressive illness or between the 2 groups of major depressive illness and non-major depressive illness can be utilized to bring about an effect of enabling more accurate discrimination between the 2 groups of depressive illness and non-depressive illness or between the 2 groups of major depressive illness and non-major depressive illness.

In discriminating between depressive illness and non-depressive illness in step S-12, the multivariate discriminant may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions and may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant. Thus, a discriminant value obtained in a multivariate discriminant useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

In discriminating between major depressive illness and non-major depressive illness in step S-12, the multivariate discriminant may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a stress state, regardless of the unit of amino acid concentration in the amino acid concentration data as input data.

In a fractional expression, the numerator of the fractional expression is expressed by the sum of amino acids A, B, C etc. and/or the denominator of the fractional expression is expressed by the sum of amino acids a, b, c etc. The fractional expression also includes the sum of fractional expressions α, β, γ etc. (for example, α+β) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each variable and the value for a constant term may be any real numbers. In combinations where variables in the numerator and variables in the denominator in the fractional expression are switched with each other, the positive (or negative) sign is generally reversed in correlation with objective variables, but because their correlation is maintained, such combinations can be assumed to be equivalent to one another in discrimination, and thus the fractional expression also includes combinations where variables in the numerator and variables in the denominator in the fractional expression are switched with each other.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When stress state is evaluated (specifically discrimination between depressive illness and non-depressive illness or discrimination between major depressive illness and non-major depressive illness) in the present invention, the concentrations of other metabolites (biological metabolites), metabolome data (organic acid, fatty acid, nucleic acid etc.), transcriptome data, proteome data, the protein expression level, the age and sex of the subject, biological indices or the like may be used in addition to the amino acid concentration data. When stress state is evaluated (specifically discrimination between depressive illness and non-depressive illness or discrimination between major depressive illness and non-major depressive illness) in the present invention, the concentrations of other metabolites (biological metabolites), the concentrations of other metabolites (biological metabolites), metabolome data (organic acid, fatty acid, nucleic acid etc.), transcriptome data, proteome data, the protein expression level, the age and sex of the subject, biological indices or the like may be used as variables in the multivariate discriminant in addition to the amino acid concentration.

1-2. Method of Evaluating Stress in Accordance with the First Embodiment

Figure 2:
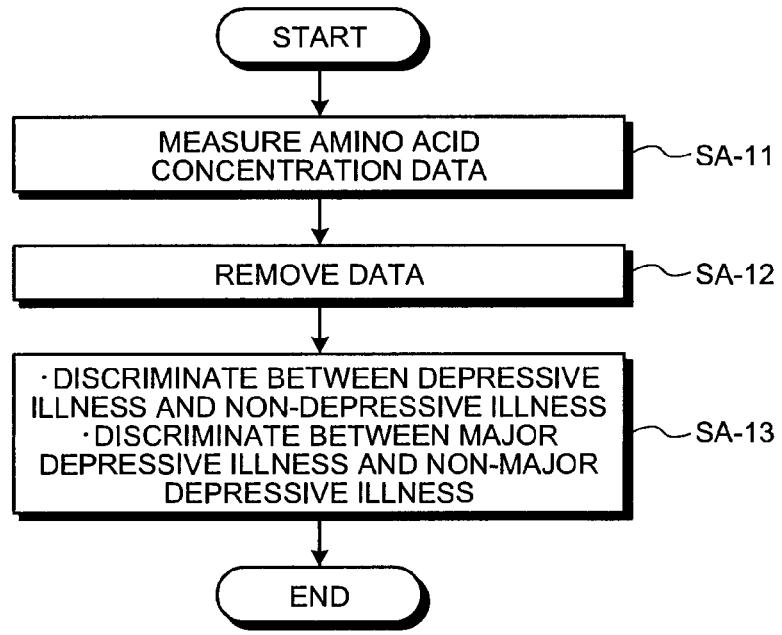
FIG. 2 is a flowchart showing one example of the method of evaluating stress according to the first embodiment.

Herein, the method of evaluating stress according to the first embodiment is described with reference to FIG. 2. FIG. 2 is a flowchart showing one example of the method of evaluating stress according to the first embodiment.

From blood collected from an individuals such as animal or human, amino acid concentration data on the concentration values of amino acids are measured (step SA-11). Measurement of the concentration values of amino acids is conducted by the method described above.

From the amino acid concentration data measured in step SA-11, data such as defective and outliers are then removed (step SA-12).

Then, at least one concentration value of Lys, His, ABA, Asn, Phe, Leu, Ile, Val, Trp, Tyr and Met contained in the amino acid concentration data of the individual from which defective and outliers have been removed in step SA-12 is compared with a previously established threshold (cutoff value), thereby discriminating between depressive illness and non-depressive illness or between major depressive illness and non-major depressive illness in the individual (step SA-13).

1-3. Summary of the First Embodiment and Other Embodiments

In the method of evaluating stress as described above in detail, (1) amino acid concentration data are measured from blood collected from an individual, (2) data such as defective and outliers are removed from the measured amino acid concentration data of the individual, and (3) at least one concentration value of Lys, His, ABA, Asn, Phe, Leu, Ile, Val, Trp, Tyr and Met contained in the amino acid concentration data of the individual from which defective and outliers have been removed is compared with a previously established threshold (cutoff value), thereby discriminating between depressive illness and non-depressive illness or between major depressive illness and non-major depressive illness in the individual. Thus, the concentrations of the amino acids which among amino acids in blood, are useful for discriminating between the 2 groups of depressive illness and non-depressive illness or between the 2 groups of major depressive illness and non-major depressive illness can be utilized to bring about an effect of enabling accurate discrimination between the 2 groups of depressive illness and non-depressive illness or between the 2 groups of major depressive illness and non-major depressive illness.

According to the method of evaluating stress, a discriminant value may be calculated based on both the concentration value of at least one of Lys, His, ABA, Asn, Phe, Leu, Ile, Val, Trp, Tyr and Met contained in the amino acid concentration data of the individual from which defective and outliers have been removed in step SA-12 and the previously established multivariate discriminant with the concentrations of at least one of Lys, His, ABA, Asn, Phe, Leu, Ile, Val, Trp, Tyr and Met as variable, and the calculated discriminant value may be compared with a previously established threshold (cutoff value), thereby discriminating between depressive illness and non-depressive illness or between major depressive illness and non-major depressive illness in the individual. The multivariate discriminant may be expressed by one fractional expression or the sum of a plurality of the fractional expressions and may contain at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant using amino acid variables useful for discriminating between the 2 groups of depressive illness and non-depressive illness or between the 2 groups of major depressive illness and non-major depressive illness can be utilized to bring about an effect of enabling accurate discrimination between the 2 groups of depressive illness and non-depressive illness or between the 2 groups of major depressive illness and non-major depressive illness.

In discriminating between depressive illness and non-depressive illness in step S-13, the multivariate discriminant may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions and may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant. Thus, a discriminant value obtained in a multivariate discriminant useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

In discriminating between major depressive illness and non-major depressive illness in step S-13, the multivariate discriminant may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions and may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a stress state, regardless of the unit of amino acid concentration in the amino acid concentration data as input data.

Second Embodiment 2-1. Outline of the Invention

Figure 3:
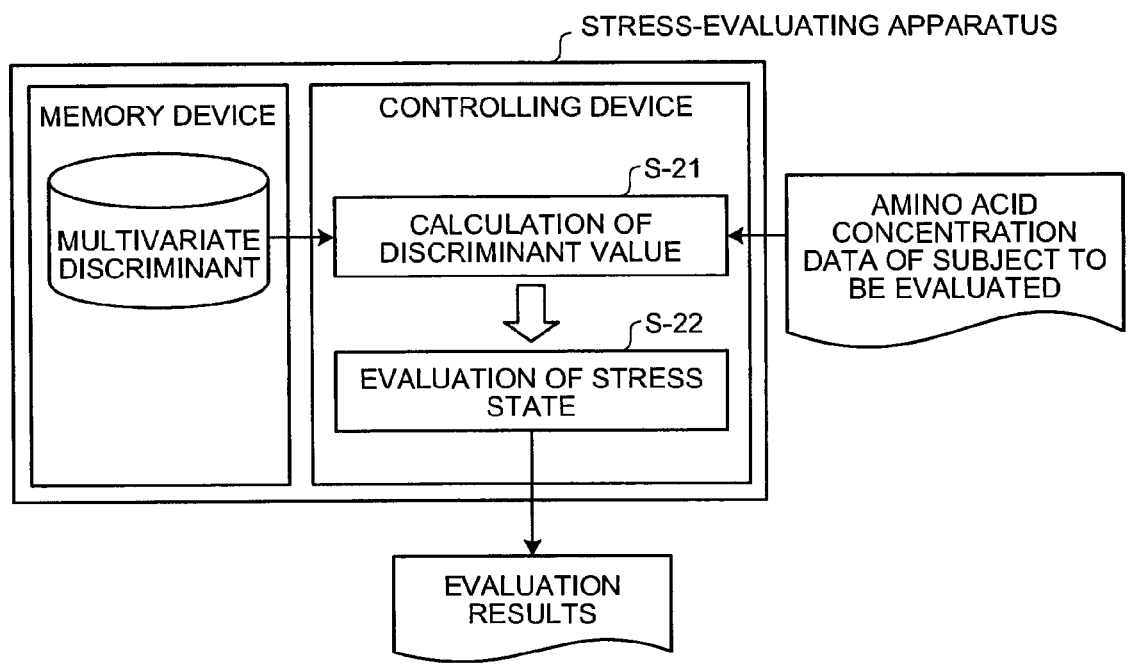
FIG. 3 is a principle configurational diagram showing the basic principle of the present invention.

Herein, an outline of the stress-evaluating apparatus, the stress-evaluating method, the stress-evaluating system, the stress-evaluating program and the recording medium of the present invention are described in detail with reference to FIG. 3. FIG. 3 is a principle configurational diagram showing the basic principle of the present invention.

In the present invention, a discriminant value that is the value of multivalent discriminant is calculated in a control device based on both the previously obtained concentration value of at least one of Lys, His, ABA, Asn, Phe, Leu, Ile, Val, Trp, Tyr and Met (for example, at least one of Lys, His, ABA, Asn, Phe, Leu, Ile, Val, Trp, Tyr, Met, BCAA, AAA, and LNAAs) contained in the amino acid concentration data of a subject to be evaluated (for example, an individual such as animal or human) and the previously established multivariate discriminant with the concentration value of at least one of Lys, His, ABA, Asn, Phe, Leu, Ile, Val, Trp, Tyr and Met (for example, at least one of Lys, His, ABA, Asn, Phe, Leu, Ile, Val, Trp, Tyr, Met, BCAA, AAA, and LNAAs) as variables, stored in the memory device (step S-21).

In the present invention, stress state including depressive illness and major depressive illness in the subject to be evaluated is evaluated in the control device based on the discriminant value calculated in step S-21 (step S-22).

According to the present invention described above, a discriminant value that is a value of multivariate discriminant is calculated based on both the concentration value of at least one of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) contained in previously obtained amino acid concentration data on the concentration value of amino acid in the subject and a multivariate discriminant with the concentration of the amino acid as variable stored in the memory device, where the concentration value of at least one of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) is contained as the variable, and the stress state including depressive illness and major depressive illness in the subject is evaluated based on the calculated discriminant value. Thus, a discriminant value obtained in a multivariate discriminant wherein the concentrations of amino acids which among amino acids in blood, are related to a stress state are variables can be utilized to bring about an effect of enabling accurate evaluation of a stress state.

In step S-22, discrimination between depressive illness and non-depressive illness or between major depressive illness and non-major depressive illness in the subject may be conducted based on the discriminant value calculated in step S-21. Specifically, the discriminant value may be compared with a previously established threshold (cutoff value), thereby discriminating between depressive illness and non-depressive illness or between major depressive illness and non-major depressive illness in the subject. The multivariate discriminant may be expressed by one fractional expression or the sum of a plurality of the fractional expressions and may contain at least one of Lys, His, ABA, Asn, Phe, Leu, Ile, Val, Trp, Tyr and Met (for example, at least one of Lys, His, ABA, Asn, Phe, Leu, Ile, Val, Trp, Tyr, Met, BCAA, AAA, and LNAAs) as the variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant (e.g., fractional expression) using amino acid variables useful for discriminating between the 2 groups of depressive illness and non-depressive illness or between the 2 groups of major depressive illness and non-major depressive illness can be utilized to bring about an effect of enabling more accurate discrimination between the 2 groups of depressive illness and non-depressive illness or between the 2 groups of major depressive illness and non-major depressive illness In discriminating between depressive illness and non-depressive illness in step S-22, the multivariate discriminant in step S-21 may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions and may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant. Thus, a discriminant value obtained in a multivariate discriminant using amino acid variables useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

In discriminating between major depressive illness and non-major depressive illness in step S-22, the multivariate discriminant in step S-21 may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

The multivariate discriminants described above can be prepared by a method described in International Publication WO 2004/052191 that is an international application filed by the present applicant or by a method (multivariate discriminant-preparing processing described later) described in International Publication PCT/JP2006/304398 that is an international application filed by the present applicant. Any multivariate discriminants obtained by these methods can be preferably used in evaluation of a stress state, regardless of the unit of amino acid concentration in the amino acid concentration data as input data.

In a fractional expression, the numerator of the fractional expression is expressed by the sum of amino acids A, B, C etc. and/or the denominator of the fractional expression is expressed by the sum of amino acids a, b, c etc. The fractional expression also includes the sum of fractional expressions α, β, γ etc. (for example, α+β) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each variable and the value for a constant term may be any real numbers. In combinations where variables in the numerator and variables in the denominator in the fractional expression are switched with each other, the positive (or negative) sign is generally reversed in correlation with objective variables, but because their correlation is maintained, such combinations can be assumed to be equivalent to one another in discrimination, and thus the fractional expression also includes combinations where variables in the numerator and variables in the denominator in the fractional expression are switched with each other.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When stress state is evaluated (specifically discrimination between depressive illness and non-depressive illness or discrimination between major depressive illness and non-major depressive illness) in the present invention, the concentrations of other metabolites (biological metabolites), metabolome data (organic acid, fatty acid, nucleic acid etc.), transcriptome data, proteome data, the protein expression level, the age and sex of the subject, biological indices or the like may be used in addition to the amino acid concentration data. When stress state is evaluated (specifically discrimination between depressive illness and non-depressive illness or discrimination between major depressive illness and non-major depressive illness) in the present invention, the concentrations of other metabolites (biological metabolites), the concentrations of other metabolites (biological metabolites), metabolome data (organic acid, fatty acid, nucleic acid etc.), transcriptome data, proteome data, the protein expression level, the age and sex of the subject, biological indices or the like may be used as variables in the multivariate discriminant in addition to the amino acid concentration.

Here, the summary of the multivariate discriminant-preparing processing (steps 1 to 4) is described in detail.

First, from stress state information including amino acid concentration data and stress state index data concerning an index showing a stress state stored in a memory device, a candidate multivariate discriminant that is a candidate for a multivariate discriminant (e.g., $y=a_1 x_1 + a_2 x_2 + \ldots + a_n x_n$, y: stress state index data, $x_i$: amino acid concentration data, $a_i$: constant, i=1, 2, . . . , n) is prepared by a predetermined discriminant-preparing method at the control device (step 1). Data containing defective and outliers may be removed in advance from the stress state information.

In step 1, a plurality of candidate multivariate discriminants may be prepared from the stress state information by using a plurality of different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of candidate multivariate discriminant groups may be prepared simultaneously and concurrently by using a plurality of different algorithms with stress state information which is multivariate data composed of amino acid concentration data and stress state index data obtained by analyzing blood samples from a large number of healthy groups and groups with finding of stress. For example, two different candidate multivariate discriminants may be formed by performing discriminant analysis and logistic regression analysis simultaneously with different algorithms. Alternatively, a candidate multivariate discriminant may be formed by converting stress state information with the candidate multivariate discriminant prepared by performing principal component analysis and then performing discriminant analysis of the converted stress state information. In this way, it is possible to finally prepare a candidate multivariate discriminant suitable for diagnostic condition.

The candidate multivariate discriminant prepared by principal component analysis is a linear expression consisting of amino acid variables maximizing the variance of all amino acid concentration data. The candidate multivariate discriminant prepared by discriminant analysis is a high-powered expression (including exponential and logarithmic expressions) consisting of amino acid variables minimizing the ratio of the sum of the variances in respective groups to the variance of all amino acid concentration data. The candidate multivariate discriminant prepared by using support vector machine is a high-powered expression (including kernel function) consisting of amino acid variables maximizing the boundary between groups. The candidate multivariate discriminant prepared by multiple regression analysis is a high-powered expression consisting of amino acid variables minimizing the sum of the distances from all amino acid concentration data. The candidate multivariate discriminant prepared by logistic regression analysis is a fraction expression having, as a component, the natural logarithm having a linear expression consisting of amino acid variables maximizing the likelihood as the exponent. The k-means method is a method of searching k pieces of neighboring amino acid concentration data in various groups designating the group containing the greatest number of the neighboring points as its data-belonging group, and selecting an amino acid variable that makes the group to which input amino acid concentration data belong agree well with the designated group. The cluster analysis is a method of clustering the points closest in entire amino acid concentration data. The decision tree is a method of ordering amino acid variables and predicting the group of amino acid concentration data from the pattern possibly held by the higher-ordered amino acid variable.

Returning to the description of the multivariate discriminant-preparing processing, the candidate multivariate discriminant prepared in step 1 is verified (mutually verified) in the control device by a particular verification method (step 2). Verification of the candidate multivariate discriminant is performed on each other to each candidate multivariate discriminant prepared in step 1.

In step 2, at least one of the discrimination rate, sensitivity, specificity, information criterion, and the like of the candidate multivariate discriminant may be verified by at least one of the bootstrap method, holdout method, leave-one-out method, and the like. In this way, it is possible to prepare a candidate multivariate discriminant higher in predictability or reliability, by taking the stress state information and the diagnostic condition into consideration.

The discrimination rate is the rate of the data wherein the stress state evaluated according to the present invention is correct, in all input data. The sensitivity is the rate of the stress states judged correct according to the present invention in the stress states declared in the input data. The specificity is the rate of the stress states judged correct according to the present invention in the stress states described healthy in the input data. The information criterion is the sum of the number of the variables in the candidate evaluation function prepared step 1 and the difference in number between the stress states evaluated according to the present invention and those described in input data. The predictability is the average of the discrimination rate, sensitivity, or specificity obtained by repeating verification of the candidate evaluation function. The reliability is the variance of the discrimination rate, sensitivity, or specificity obtained by repeating verification of the candidate evaluation function.

Returning to the description of the multivariate discriminant-preparing processing, a combination of amino acid concentration data contained in the stress state information used in preparing the candidate multivariate discriminant is selected by selecting a variable of the candidate multivariate discriminant from the verification result in step 2 according to a predetermined variable selection method in the control device (step 3). The selection of amino acid variable is performed on each candidate multivariate discriminant prepared in step 1. In this way, it is possible to select the amino acid variable of the candidate multivariate discriminant properly. The step 1 is executed once again by using the stress state information including the amino acid concentration data selected in step 3.

From the verification result in step 2, an amino acid variable of the candidate multivariate discriminant may be selected in step 3, based on at least one of stepwise method, best path method, local search method, and genetic algorithm.

The best path method is a method of selecting an amino acid variable by optimizing the evaluation index of the candidate multivariate discriminant while eliminating the variables contained in the candidate multivariate discriminant one by one.

Returning to the description of the multivariate discriminant-preparing processing, the steps 1, 2 and 3 are repeatedly performed in the control device, and based on verification results thus accumulated, a candidate multivariate discriminant used as multivariate discriminant is selected from a plurality of candidate multivariate discriminants, thereby preparing the multivariate discriminant (step 4). In selection of the candidate multivariate discriminants, there are cases where the optimum multivariate discriminant is selected from candidate multivariate discriminants prepared in the same method or the optimum multivariate discriminant is selected from all candidate multivariate discriminants.

As described above, processing for preparation of candidate multivariate discriminants based on stress state information, verification of the candidate multivariate discriminants, and selection of variables in the candidate multivariate discriminants are performed in a series of operations in a systematized manner in the multivariate discriminant-preparing processing, whereby the optimum multivariate discriminant for evaluation of stress state can be prepared. In other words, in the multivariate discriminant-preparing processing, amino acid concentration is used in multivariate statistical analysis, and for selecting the optimum and robust combination of variables, the variable selection method is combined with cross-validation to extract a multivariate discriminant having high diagnosis performance. Logistic regression equation, linear discriminant function, support vector machine, Mahalanobis' generalized distance, multiple regression analysis, cluster analysis and the like can be used in the multivariate discriminant.

2-2. System Configuration

Hereinafter, the configuration of the stress-evaluating system according to the second embodiment (hereinafter referred to sometimes as the present system) will be described with reference to FIGS. 4 to 20. This system is merely one example, and the present invention is not limited thereto.

Figure 4:
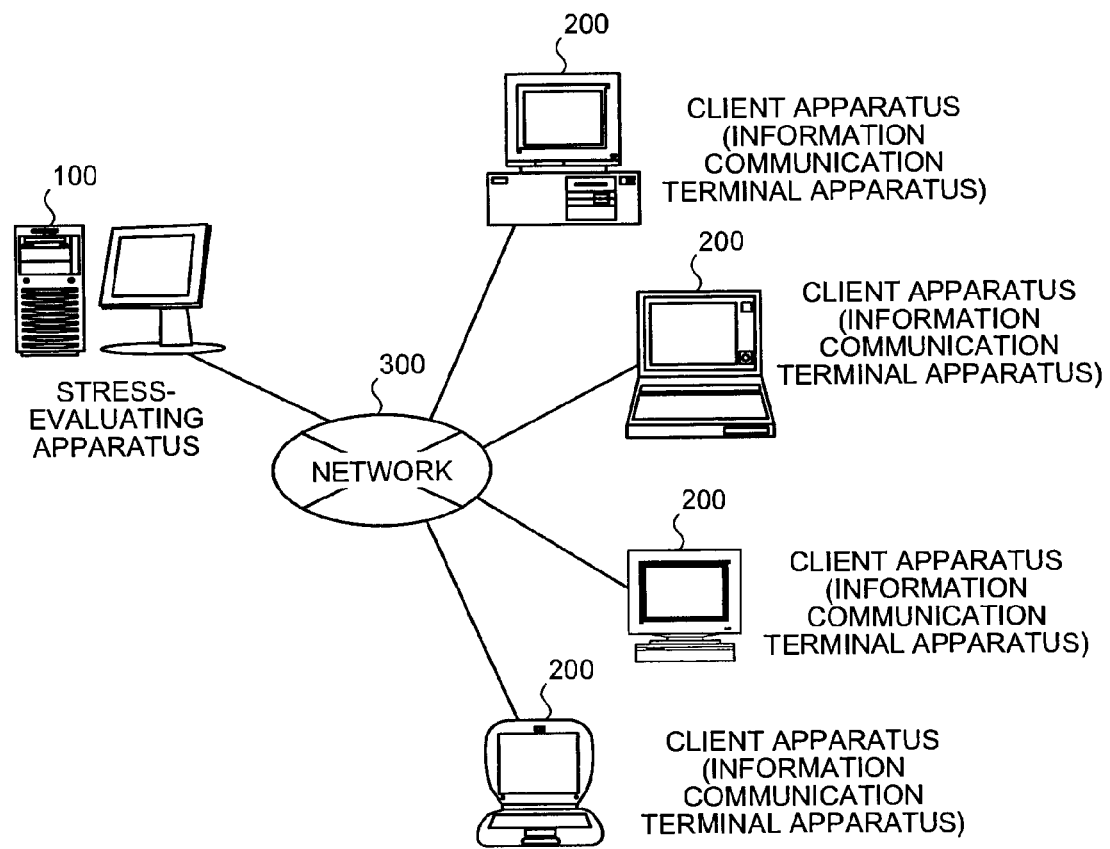
FIG. 4 is a diagram showing an example of the entire configuration of the present system.
Figure 5:
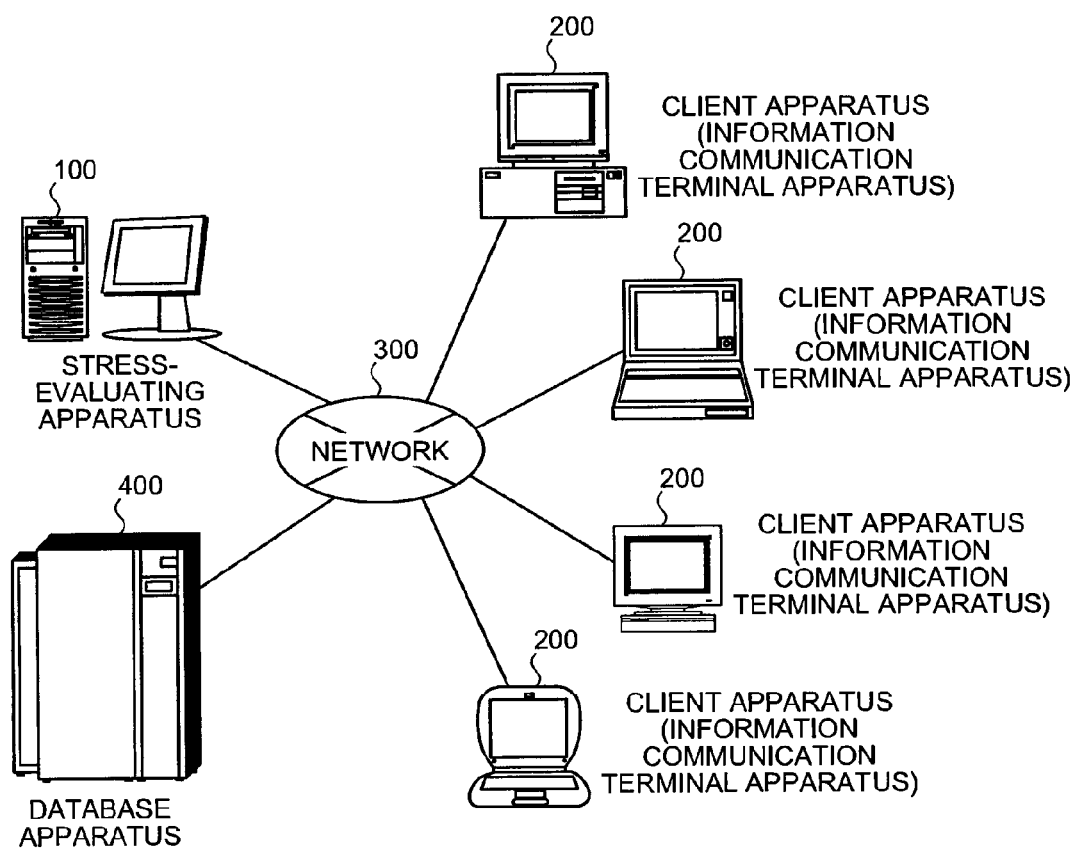
FIG. 5 is a diagram showing another example of the entire configuration of the present system.

First, the entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which a stress-evaluating apparatus 100 that evaluates a stress state in a subject to be evaluated, and a client apparatus 200 (corresponding to the information communication terminal apparatus of the present invention) which provides the amino acid concentration data on the concentration values of amino acids in the subject, are communicatively connected to each other via a network 300.

In the present system as shown in FIG. 5, in addition to the stress-evaluating apparatus 100 and the client apparatus 200, a database apparatus 400 storing, for example, the stress state information used in preparing a multivariate discriminant and the multivariate discriminant used in evaluating a stress state in the stress-evaluating apparatus 100, may be communicatively connected via the network 300. In this configuration, the information on a stress state etc. are provided via the network 300 from the stress-evaluating apparatus 100 to the client apparatuses 200 and the database apparatus 400, or from the client apparatuses 200 and the database apparatus 400 to the stress-evaluating apparatus 100. The "information on a stress state" is information on the measured values of particular items of the stress state of organisms including human. The information on a stress state is generated in the stress-evaluating apparatus 100, client apparatus 200, and other apparatuses (e.g., various measuring apparatuses) and stored mainly in the database apparatus 400.

Figure 6:
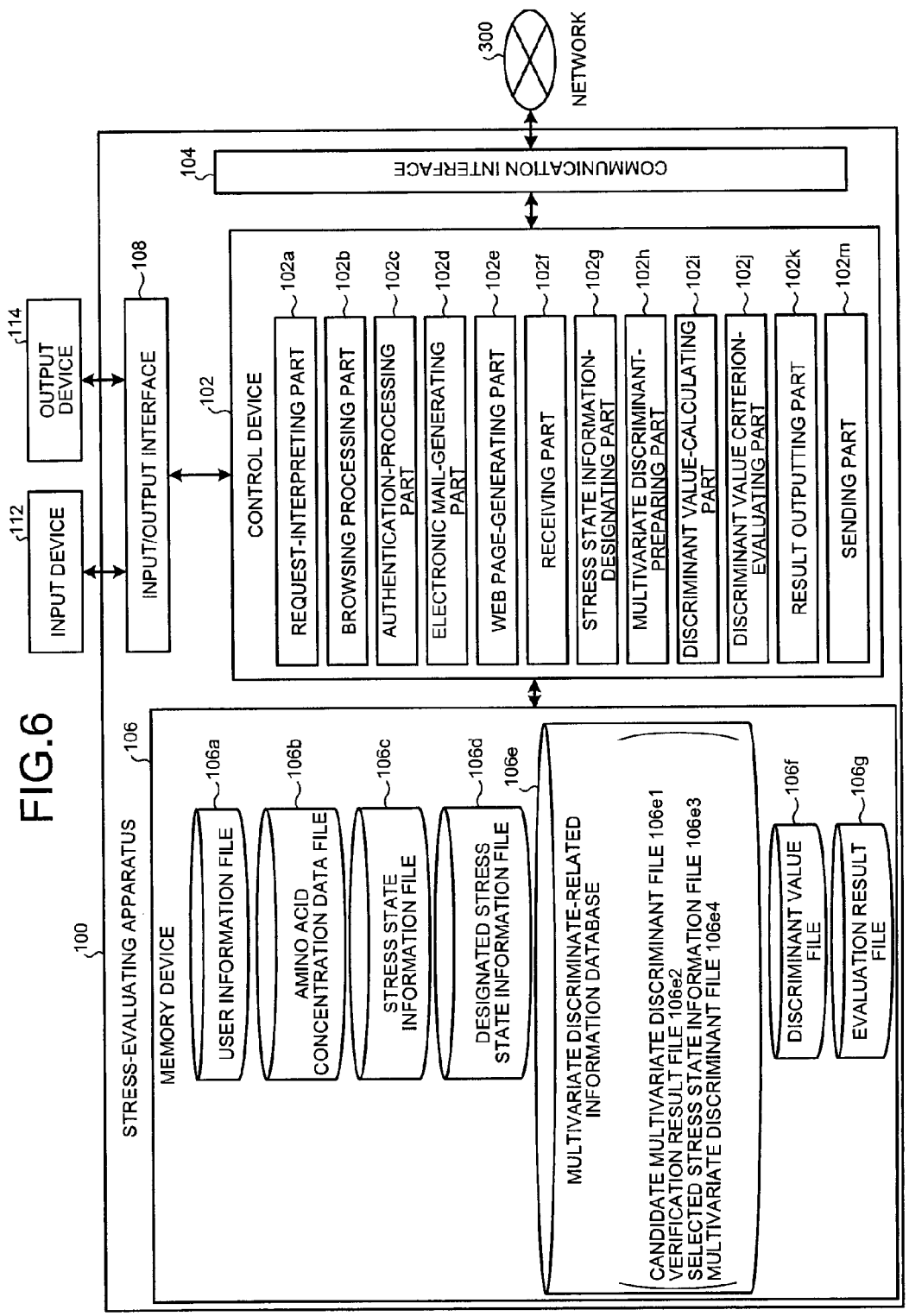
FIG. 6 is a block diagram showing an example of the configuration of the stress-evaluating apparatus 100 in the present system.

Now, the configuration of the stress-evaluating apparatus 100 in the present system will be described with reference to FIGS. 6 to 18. FIG. 6 is a block diagram showing an example of the configuration of the stress-evaluating apparatus 100 in the present system, showing conceptually only the region relevant to the present invention.

The stress-evaluating apparatus 100 includes a control device 102, such as CPU (Central Processing Unit), that integrally controls the stress-evaluating apparatus 100, a communication interface 104 that connects the stress-evaluating apparatus 100 to the network 300 communicatively via communication apparatuses such as router and a wired or wireless communication line such as private line, a memory device 106 that stores various databases, tables, files and others, and an input/output interface 108 connected to an input device 112 and an output device 114, that are connected to each other communicatively via any communication channel. The stress-evaluating apparatus 100 may be present together with various analyzers (e.g., amino acid analyzer) in a same housing. Typical configuration of disintegration/integration of the stress-evaluating apparatus 100 is not limited to that shown in the figure, and all or a part of it may be disintegrated or integrated functionally or physically in any unit, for example, according to various loads applied. For example, a part of the processing may be performed via a CGI (Common Gateway Interface).

The memory device 106 is a storage means, and examples thereof include memory apparatuses such as RAM (Random Access Memory) and ROM (Read Only Memory), fixed disk drives such as hard disk, flexible disk, optical disk, and the like. The memory device 106 stores computer programs giving instructions to CPU for various processing, together with OS (Operating System). As shown in the figure, the memory device 106 stores a user information file 106*a*, an amino acid concentration data file 106*b*, a stress state information file 106*c*, a designated stress state information file 106*d*, a multivariate discriminant-related information database 106*e*, a discriminant value file 106*f* and an evaluation result file 106*g*.

The user information file 106*a* stores a user information on users. FIG. 7 is a chart showing an example of the information stored in the user information file 106*a*. As shown in FIG. 7, the information stored in the user information file 106*a* includes user ID (identification) for identifying the user uniquely, user password for authentication of the user, user name, organization ID uniquely identifying the organization of the user, department ID for uniquely identifying the department of the user organization, department name, and electronic mail address of the user that are correlated to one another. Returning to FIG. 6, the amino acid concentration data file 106*b* stores amino acid concentration data on amino acid concentration values. FIG. 8 is a chart showing an example of the information stored in the amino acid concentration data file 106*b*. As shown in FIG. 8, the information stored in the amino acid concentration data file 106*b* includes individual number for uniquely identifying an individual (sample) as a subject to be evaluated and amino acid concentration data that are correlated to one another. In FIG. 8, the amino acid concentration data are assumed to be numerical values, i.e., on continuous scale, but the amino acid concentration data may be expressed on nominal scale or ordinal scale. In the case of nominal or ordinal scale, any number may be allocated to each state for analysis. The amino acid concentration data may be combined with other biological information (e.g., sex difference, age, height, weight, BMI index, abdominal circumference, insulin resistance index, uric acid level, blood glucose level, neutral fat, body fat percentage, total cholesterol, HDL cholesterol, LDL cholesterol, systolic pressure, diastolic pressure, hemoglobin A1c, arteriosclerosis index, smoking, alcohol consumption, digitalized electrocardiogram waveform, enzyme concentration, gene expression level, brain waves, heart rates, cortisol, hippocampal volume, cerebral blood flow rate, brain-derived neurotrophic factor, amylase activity, chromogranin A, dopamine, and concentrations of metabolites other than amino acids).

Returning to FIG. 6, the stress state information file 106*c* stores the stress state information used in preparing a multivariate discriminant. FIG. 9 is a chart showing an example of the information stored in the stress state information file 106*c*. As shown in FIG. 9, the information stored in the stress state information file 106*c* includes individual (sample) number, stress state index data (T) corresponding to the stress state index (index $T_1$, index $T_2$, index $T_3$ . . . ), and amino acid concentration data that are correlated to one another. In FIG. 9, the stress state index data and the amino acid concentration data are assumed to be numerical values, i.e., on continuous scale, but the stress state index data and the amino acid concentration data may be expressed on nominal scale or ordinal scale. In the case of nominal or ordinal scale, any number may be allocated to each state for analysis. The stress state index data is a single known state index serving as a marker of stress state, and numerical data may be used.

Returning to FIG. 6, the designated stress state information file 106*d* stores the stress state information designated in the stress state information-designating part 102*g* described below. FIG. 10 is a chart showing an example of the information stored in the designated stress state information file 106*d*. As shown in FIG. 10, the information stored in the designated stress state information file 106*d* includes individual number, designated stress state index data, and designated amino acid concentration data that are correlated to one another.

Returning to FIG. 6, the multivariate discriminant-related information database 106*e* is composed of a candidate multivariate discriminant file 106*e*1 storing the candidate multivariate discriminant prepared in the candidate multivariate discriminant-preparing part 102*h*1 described below; a verification result file 106*e*2 storing the verification results in the candidate multivariate discriminant-verifying part 102*h*2 described below; a selected stress state information file 106*e*3 storing the stress state information containing the combination of amino acid concentration data selected in the variable-selecting part 102*h*3 described below; and a multivariate discriminant file 106*e*4 storing the multivariate discriminant prepared in the multivariate discriminant-preparing part 102*h* described below.

The candidate multivariate discriminant file 106*e*1 stores the candidate multivariate discriminant prepared in the candidate multivariate discriminant-preparing part 102*h*1 described below. FIG. 11 is a chart showing an example of the information stored in the candidate multivariate discriminant file 106*e*1. As shown in FIG. 11, the information stored in the candidate multivariate discriminant file 106e1 includes rank, and candidate multivariate discriminant (e.g., $F_1$ (Gly, Leu, Phe, ... ), $F_2$ (Gly, Leu, Phe, ... ), or $F_3$ (Gly, Leu, Phe, ... ) in FIG. 11) that are correlated to each other.

Returning to FIG. 6, the verification result file 106e2 stores the verification results verified in the candidate multivariate discriminant-verifying part 102h2 described below. FIG. 12 is a chart showing an example of the information stored in the verification result file 106e2. As shown in FIG. 12, the information stored in the verification result file 106e2 includes rank, candidate multivariate discriminant (e.g., $F_k$ (Gly, Leu, Phe, ... ), $F_m$ (Gly, Leu, Phe, ... ), Fl (Gly, Leu, Phe, ... ) in FIG. 12), and the verification results of each candidate multivariate discriminant (e.g., evaluation value of each candidate multivariate discriminant) that are correlated to one another.

Returning to FIG. 6, the selected stress state information file 106e3 stores the stress state information including the combination of amino acid concentration data corresponding to the variable selected in the variable-selecting part 102h3 described below. FIG. 13 is a chart showing an example of the information stored in the selected stress state information file 106e3. As shown in FIG. 13, the information stored in the selected stress state information file 106e3 includes individual number, the stress state index data designated in the stress state information-designating part 102g described below, and the amino acid concentration data selected in the variable-selecting part 102h3 described below that are correlated to one another.

Returning to FIG. 6, the multivariate discriminant file 106e4 stores the multivariate discriminant prepared in the multivariate discriminant-preparing part 102h described below. FIG. 14 is a chart showing an example of the information stored in the multivariate discriminant file 106e4. As shown in FIG. 14, the information stored in the multivariate discriminant file 106e4 includes rank, multivariate discriminant (e.g., $F_p$ (Phe, ... ), $F_p$ (Gly, Leu, Phe), $F_k$ (Gly, Leu, Phe, ... ) in FIG. 14), a threshold corresponding to each discriminant-preparing method, and verification results of each multivariate discriminant (e.g., evaluation value of each multivariate discriminant) that are correlated to one another.

Returning to FIG. 6, the discriminant value file 106f stores the discriminant value calculated in the discriminant value-calculating part 102i described below. FIG. 15 is a chart showing an example of the information stored in the discriminant value file 106f. As shown in FIG. 15, the information stored in the discriminant value file 106f includes individual number for uniquely identifying an individual (sample) as a subject to be evaluated, rank (number for uniquely identifying the multivariate discriminant), and discriminant value that are correlated to one another.

Figures 16, 17:
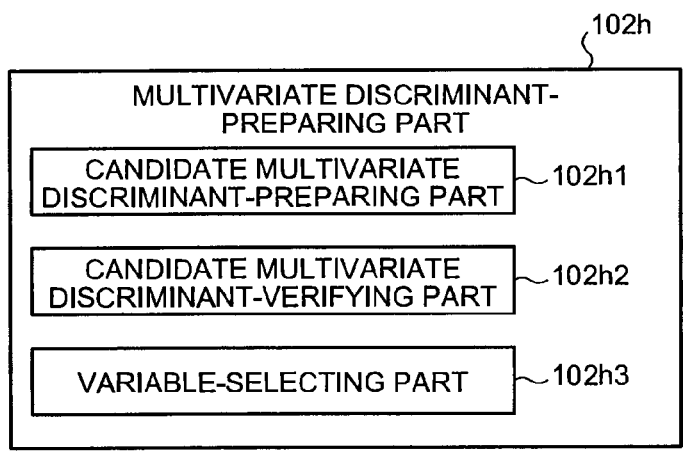
FIG. 16 is a chart showing an example of the information stored in the evaluation result file 106*g*.
FIG. 17 is a block diagram showing the configuration of the multivariable discriminant-preparing part 102*h*.

Returning to FIG. 6, the evaluation result file 106g stores the evaluation results obtained in the discriminant value criterion-evaluating part 102j described below (specifically the discrimination results obtained in the discriminant value criterion-discriminating part 102j1). FIG. 16 is a chart showing an example of the information stored in the evaluation result file 106g. The information stored in the evaluation result file 106g includes individual number for uniquely identifying an individual (sample) as a subject to be evaluated, the previously obtained amino acid concentration data on a subject to be evaluated, the discriminant value calculated in the multivariate discriminant, and the evaluation results on the stress state (specifically, discrimination results as to discrimination between depressive illness and non-depressive illness or discrimination results as to discrimination between major depressive illness and non-major depressive illness) that are correlated to one another.

Returning to FIG. 6, the memory device 106 stores various Web data, CGI programs, and others for providing the client apparatuses 200 with web site information as information other than the information described above. The Web data include various data for displaying the Web page described below and others, and the data are generated as, for example, a HTML (HyperText Markup Language) or XML (Extensible Markup Language) text file. Other temporary files such as files for the components for generation of Web data and for operation, and others are also stored in the memory device 106. In addition, it may store as needed sound files in the WAVE or AIFF (Audio Interchange File Format) format for transmission to the client apparatuses 200 and image files of still image or motion picture in the JPEG (Joint Photographic Experts Group) or MPEG2 (Moving Picture Experts Group phase 2) format.

The communication interface 104 allows communication between the stress-evaluating apparatus 100 and the network 300 (or communication apparatus such as router). Thus, the communication interface 104 has a function to communicate data via a communication line with other terminals.

The input/output interface 108 is connected to the input device 112 and the output device 114. A monitor (including home television), a speaker, or a printer may be used as the output device 114 (hereinafter, the output device 114 may be described as monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs information processing according to these programs. As shown in the figure, the control device 102 includes mainly the request-interpreting part 102a, a browsing processing part 102b, an authentication-processing part 102c, an electronic mail-generating part 102d, a Web page-generating part 102e, a receiving part 102f, a stress state information-designating part 102g, a multivariate discriminant-preparing part 102h, a discriminant value-calculating part 102i, a discriminant value criterion-evaluating part 102j, a result outputting part 102k and a sending part 102m. The control device 102 performs data processing such as removal of data including defective or many outliers and of variables for the defective value-including data in the stress state information transmitted from the database apparatus 400 and in the amino acid concentration data transmitted from the client apparatus 200.

The request-interpreting part 102a interprets the request from the client apparatus 200 or the database apparatus 400 and sends the request to other parts in the control device 102 according to the analytical result. Upon receiving browsing request for various screens from the client apparatus 200, the browsing processing part 102b generates and transmits the web data for these screens. Upon receiving authentication request from the client apparatus 200 or the database apparatus 400, the authentication-processing part 102c performs authentication. The electronic mail-generating part 102d generates an electronic mail including various kinds of information. The Web page-generating part 102e generates a Web page for a user to browse with the client apparatus 200.

The receiving part 102f receives, via the network 300, the information (specifically, the amino acid concentration data, stress state information, multivariate discriminant etc.) transmitted from the client apparatus 200 and the database apparatus 400. The stress state information-designating part 102g designates the objective stress state index data and amino acid concentration data in preparing the multivariate discriminant.

The multivariate discriminant-preparing part 102h generates a multivariate discriminant based on the stress state information received in the receiving part 102f and the stress state information designated in the stress state information-designating part 102g. Specifically, the multivariate discriminant-preparing part 102h generates a multivariate discriminant by selecting a candidate multivariate discriminant to be used as the multivariate discriminant from a plurality of candidate multivariate discriminants, according to the verification results accumulated by repeating the processings in the candidate multivariate discriminant-preparing part 102h1, the candidate multivariate discriminant-verifying part 102h2 and the variable-selecting part 102h3 from the stress state information.

If a previously generated multivariate discriminant is stored in a predetermined region of the memory device 106, the multivariate discriminant-preparing part 102h may generate a multivariate discriminant by selecting a desired multivariate discriminant out of the memory device 106. Alternatively, the multivariate discriminant-preparing part 102h may generate the multivariate discriminant by selecting and downloading a desired multivariate discriminant from the multivariate discriminants previously stored in another computer apparatus (e.g., database apparatus 400).

Hereinafter, the configuration of the multivariate discriminant-preparing part 102h will be described with reference to FIG. 17. FIG. 17 is a block diagram showing the configuration of the multivariate discriminant-preparing part 102h, and only a part in the configuration related to the present invention is shown conceptually. The multivariate discriminant-preparing part 102h has a candidate multivariate discriminant-preparing part 102h1, a candidate multivariate discriminant-verifying part 102h2, and a variable-selecting part 102h3, additionally. The candidate multivariate discriminant-preparing part 102h1 generates a candidate multivariate discriminant that is a candidate of the multivariate discriminant from the stress state information according to a predetermined discriminant-preparing method. Specifically, the candidate multivariate discriminant-preparing part 102h1 may generate a plurality of candidate multivariate discriminants from the stress state information, by using a plurality of different discriminant-preparing methods. The candidate multivariate discriminant-verifying part 102h2 verifies the candidate multivariate discriminants prepared in the candidate multivariate discriminant-preparing part 102h1 according to a particular verification method. Specifically, the candidate multivariate discriminant-verifying part 102h2 may verify at least one of the discrimination rate, sensitivity, specificity, and information criterion of the candidate multivariate discriminants according to at least one of bootstrap method, holdout method, and leave-one-out method. The variable-selecting part 102h3 selects the combination of the amino acid concentration data contained in the stress state information to be used in preparing the candidate multivariate discriminant, by selecting a variable of the candidate multivariate discriminant from the verification results in the candidate multivariate discriminant-verifying part 102h2 according to a particular variable selection method. The variable-selecting part 102h3 may select the variable of the candidate multivariate discriminant from the verification results according to at least one of stepwise method, best path method, local search method, and genetic algorithm.

Returning to FIG. 6, the discriminant value-calculating part 102i calculates a discriminant value that is the value of the multivariate discriminant, based on at least one concentration value of Lys, His, ABA, Asn, Phe, Leu, Ile, Val, Trp, Tyr and Met (for example, at least one concentration value of Lys, His, ABA, Asn, Phe, Leu, Ile, Val, Trp, Tyr, Met, BCAA, AAA, and LNAAs) contained in the amino acid concentration data of a subject to be evaluated received in the receiving part 102f and the multivariate discriminant containing at least one of Lys, His, ABA, Asn, Phe, Leu, Ile, Val, Trp, Tyr and Met (for example, multivariate discriminant containing at least one concentration value of Lys, His, ABA, Asn, Phe, Leu, Ile, Val, Trp, Tyr, Met, BCAA, AAA, and LNAAs) as variables prepared in the multivariate discriminant-preparing part 102h.

The multivariate discriminant may be expressed by one fractional expression or the sum of a plurality of the fractional expressions and may contain at least one of Lys, His, ABA, Asn, Phe, Leu, Ile, Val, Trp, Tyr and Met (for example, at least one of Lys, His, ABA, Asn, Phe, Leu, Ile, Val, Trp, Tyr, Met, BCAA, AAA, and LNAAs) as the variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, When the after-mentioned discriminant value criterion-discriminating part 102j1 discriminates between depressive illness and non-depressive illness, the multivariate discriminant may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

When the after-mentioned discriminant value criterion-discriminating part 102j1 discriminates between major depressive illness and non-major depressive illness, the multivariate discriminant may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Figure 18:
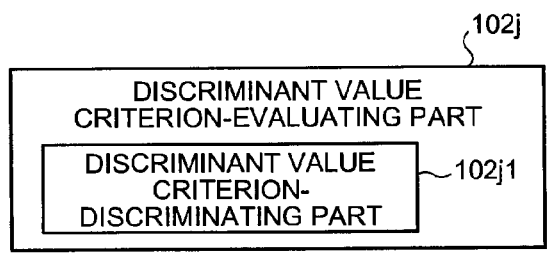
FIG. 18 is a block diagram showing the configuration of the discriminant criterion-evaluating part 102*j*.

Returning to FIG. 6, the discriminant value criterion-evaluating part 102j evaluates a stress state including depressive illness and major depressive illness in the subject to be evaluated, based on the discriminant value calculated in the discriminant value-calculating part 102i. The discriminant value criterion-evaluating part 102j further includes a discriminant value criterion-discriminating part 102j1. Now, the configuration of the discriminant value criterion-evaluating part 102j will be described with reference to FIG. 18. FIG. 18 is a block diagram showing the configuration of the discriminant value criterion-evaluating part 102j, and only a part in the configuration related to the present invention is shown conceptually. Based on the discriminant value, the discriminant value criterion-discriminating part 102j1 discriminates between depressive illness and non-depressive illness or between major depressive illness and non-major depressive illness, in the subject to be evaluated. Specifically, the discriminant value criterion-discriminating part 102j1 compares the discriminant value with a predetermined threshold value (cutoff value), thereby discriminating between depressive illness and non-depressive illness or between major depressive illness and non-major depressive illness, in the subject to be evaluated.

Returning to FIG. 6, the result outputting part 102k outputs, into the output device 114, the processing results in each processing part in the control device 102 (the evaluation results in the discriminant value criterion-evaluating part 102j (specifically the discrimination results in the discriminant value criterion-discriminating part 102j1)) etc.

The sending part 102m sends the evaluation results to the client apparatus 200 that is the sender of the amino acid concentration data of the subject to be evaluated or sends the multivariate discriminant prepared in the stress-evaluating apparatus 100, and the evaluation results, to the database apparatus 400.

Figure 19:
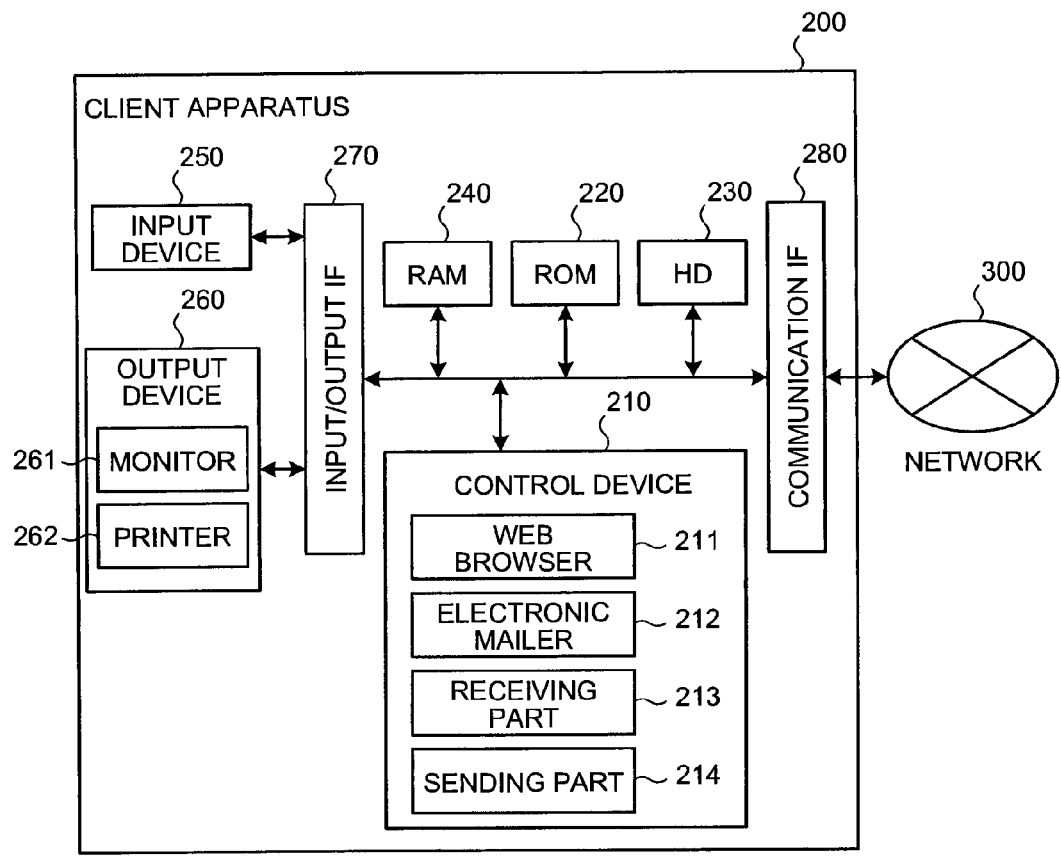
FIG. 19 is a block diagram showing an example of the configuration of the client apparatus 200 in the present system.

Hereinafter, the configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, input/output IF 270, and communication IF 280 that are connected communicatively to one another through a communication channel.

The control device 210 has a Web browser 211, an electronic mailer 212, a receiving part 213, and a sending part 214. The Web browser 211 performs browsing processing of interpreting Web data and displaying the interpreted Web data on a monitor 261 described below. The Web browser 211 may have various plug-in software, such as stream player, having functions to receive, display and feedback streaming screen image. The electronic mailer 212 sends and receives electronic mails using a particular protocol (e.g., SMTP (Simple Mail Transfer Protocol) or POP3 (Post Office Protocol version 3)). The receiving part 213 receives various information, such as the evaluation results transmitted from the stress-evaluating apparatus 100, via the communication IF 280. The sending part 214 sends various information such as the amino acid concentration data on the subject to be evaluated, via communication IF 280, to the stress-evaluating apparatus 100.

The input device 250 is for example a keyboard, a mouse or a microphone. The monitor 261 described below also functions as a pointing device together with a mouse. The output device 260 is an output means for outputting the information received via the communication IF 280, and includes the monitor (including home television) 261 and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as router) communicatively. In other words, the client apparatuses 200 are connected to the network 300 via a communication apparatus such as modem, TA (Terminal Adapter) or router, and a telephone line, or a private line. In this way, the client apparatuses 200 can access to the stress-evaluating apparatus 100 by using a particular protocol.

The client apparatus 200 may be realized by installing software (including programs, data and others) for Web data-browsing function and electronic mail-processing function to information processing apparatus (for example, information processing terminal such as known personal computer, workstation, family computer, Internet TV (Television), PHS (Personal Handyphone System) terminal, mobile phone terminal, mobile unit communication terminal or PDA (Personal Digital Assistants)) connected as needed with peripheral devices such as printer, monitor, and image scanner.

All or a part of processings of the control device 210 in the client apparatus 200 may be performed by a CPU and programs read and executed by the CPU. Thus, computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in an application program server connected via any network to the client apparatus 200, and the client apparatus 200 may download all or a part of them as needed. All or any part of processings of the control device 210 may be realized by hardware such as wired-logic.

Hereinafter, the network 300 in the present system will be described with reference to FIGS. 4 and 5. The network 300 has a function to connect the stress-evaluating apparatus 100, the client apparatuses 200, and the database apparatus 400 mutually, communicatively to one another, and is for example the Internet, intranet, or LAN (Local Area Network (both wired/wireless)). The network 300 may be VAN (Value Added Network), personal computer communication network, public telephone network (including both analog and digital), leased line network (including both analog and digital), CATV (Community Antenna Television) network, portable switched network or portable packet-switched network (including IMT2000 (International Mobile Telecommunication 2000) system, GSM (Global System for Mobile Communications) system, or PDC (Personal Digital Cellular)/PDC-P system), wireless calling network, local wireless network such as Bluetooth (registered trademark), PHS network, satellite communication network (including CS (Communication Satellite), BS (Broadcasting Satellite), and ISDB (Integrated Services Digital Broadcasting)), or the like.

Figure 20:
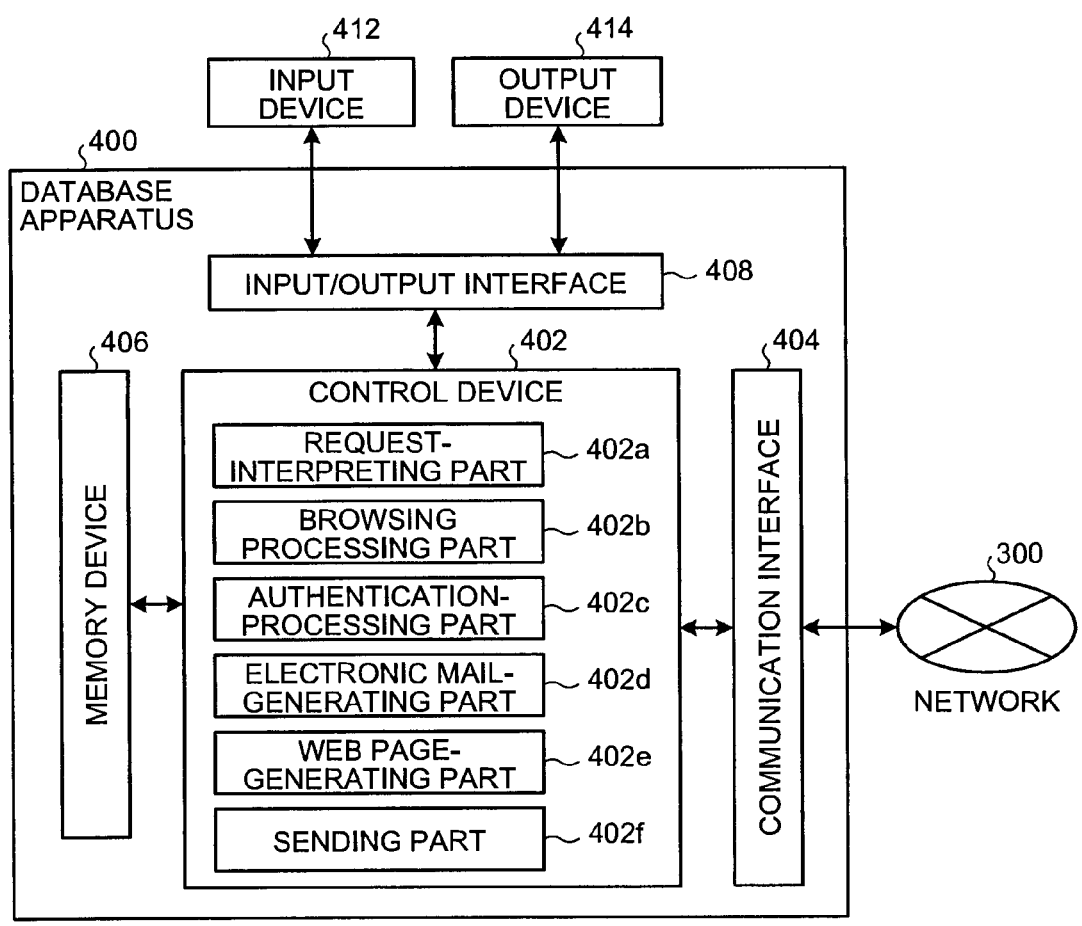
FIG. 20 is a block diagram showing an example of the configuration of the database apparatus 400 in the present system.

Hereinafter, the configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the stress state information used in preparing a multivariate discriminant in the stress-evaluating apparatus 100 or in the database apparatus, the multivariate discriminant prepared in the stress-evaluating apparatus 100, and the evaluation results in the stress-evaluating apparatus 100. As shown in FIG. 20, the database apparatus 400 includes a control device 402, such as CPU, which controls the entire database apparatus 400 integrally, a communication interface 404 connecting the database apparatus to the network 300 communicatively via a communication apparatus such as router and via a wired or wireless communication circuit such as private line, a memory device 406 storing various data, tables and files (for example, file for Web page), and an input/output interface 408 connected to an input device 412 and an output device 414, and these parts are connected communicatively to each other via any communication channel.

The memory device 406 is a storage means, and may be, for example, memory apparatus such as RAM or ROM, fixed disk drive such as harddisk, flexible disk, optical disk, or the like. Various programs used in various processings are stored in the memory device 406. The communication interface 404 allows communication between the database apparatus 400 and the network 300 (or communication apparatus such as router). Thus, the communication interface 404 has a function to communicate data with other terminal via a communication line. The input/output interface 408 is connected to the input device 412 and the output device 414. A monitor (including home television), a speaker, or a printer may be used as the output device 414 (hereinafter, the output device 414 may be described as monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processing according to these programs. As shown in the figure, the control device 402 includes mainly the request-interpreting part 402*a*, a browsing processing part 402*b*, an authentication-processing part 402*c*, an electronic mail-generating part 402*d*, a Web page-generating part 402*e*, and a sending part 402*f*.

The request-interpreting part 402*a* interprets the request from the stress-evaluating apparatus 100 and sends the request to other parts in the control device 402 according to the analytical result. Upon receiving various screen-browsing request from the stress-evaluating apparatus 100, the browsing processing part 402*b* generates and transmits web data for these screens. Upon receipt of authentication request from the stress-evaluating apparatus 100, the authentication-processing part 402*c* performs authentication. The electronic mail-generating part 402*d* generates an electronic mail including various information. The Web page-generating part 402*e* generates a Web page for a user to browse with the client apparatus 200. The sending part 402*f* sends the information such as the stress state information and the multivariate discriminant to the stress-evaluating apparatus 100.

2-3. Processing in the Present System

Figure 21:
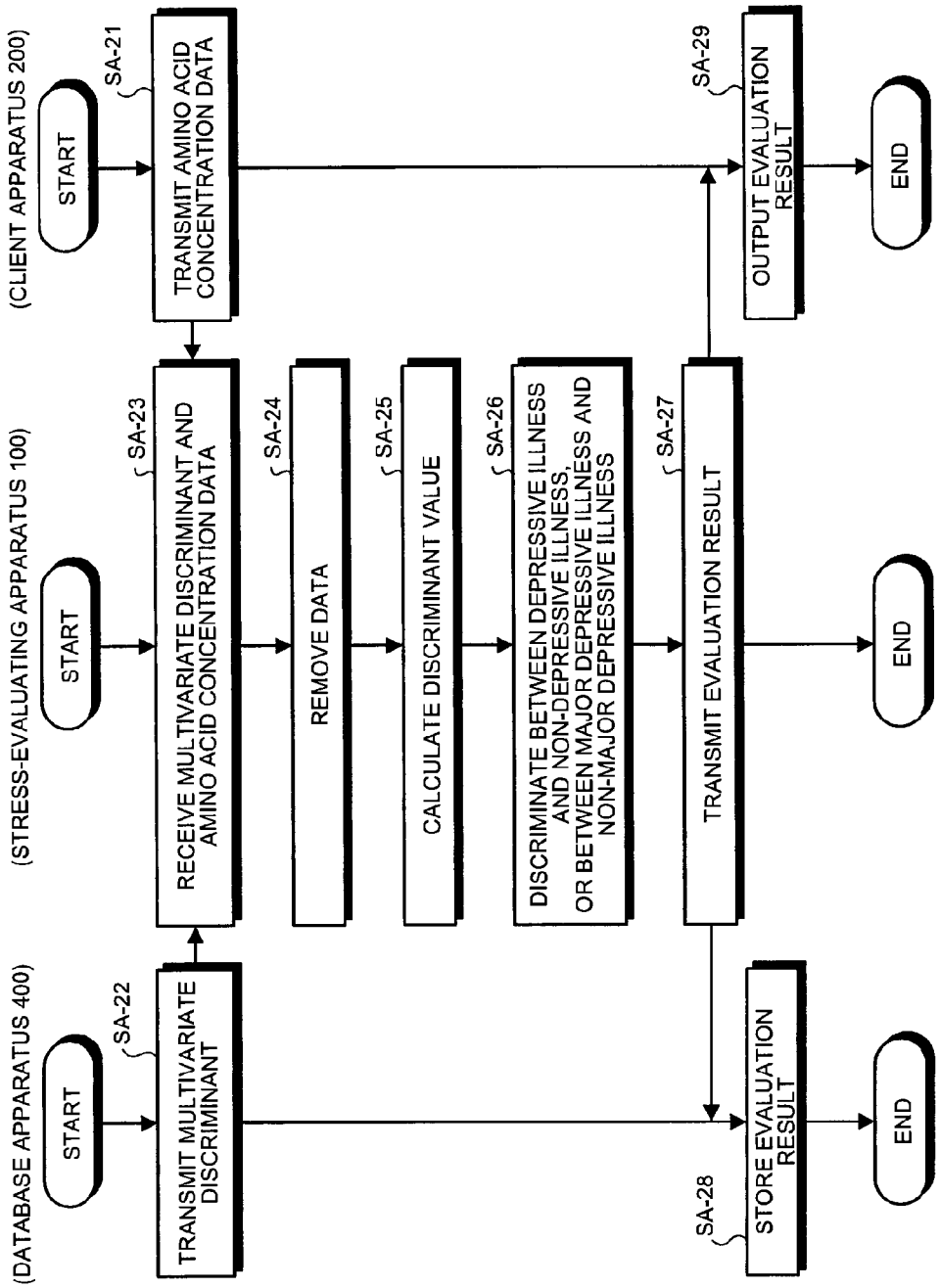
FIG. 21 is a flowchart showing an example of the stress evaluation service processing performed in the present system.

Here, an example of the stress evaluation service processing performed in the present system constituted as described above will be described with reference to FIG. 21. FIG. 21 is a flowchart showing an example of the stress evaluation service processing.

The amino acid concentration data used in the present processing concerns amino acid concentration value obtained by analyzing blood previously collected from an individual. Hereinafter, the method of analyzing blood amino acid will be described briefly. First, a blood sample is collected in a heparin-treated tube, and then the blood plasma is separated by centrifugation of the tube. All blood plasma samples separated are frozen and stored at −70° C. before measurement of amino acid concentration. Before measurement of amino acid concentration, the blood plasma sample is deproteinized by adding sulfosalicylic acid to a concentration of 3%. An amino acid analyzer and a high-performance liquid chromatography/mass spectrometer (LC/MS) by high-performance liquid chromatography (HPLC) by using ninhydrin reaction in the post column were used for measurement of amino acid concentration.

First, the client apparatus 200 accesses the stress-evaluating apparatus 100 when the user specifies the Web site address (such as URL) provided from the stress-evaluating apparatus 100, via the input device 250 on the screen displaying Web browser 211. Specifically, when the user instructs update of the Web browser 211 screen on the client apparatus 200, the Web browser 211 sends the Web site's address provided from the stress-evaluating apparatus 100 by a particular protocol, thereby transmitting a request demanding transmission of the Web page corresponding to the amino acid concentration data transmission screen to the stress-evaluating apparatus 100 based on the routing of the address.

Then, upon receipt of the request from the client apparatus 200, the request-interpreting part 102*a* in the stress-evaluating apparatus 100 analyzes the transmitted request and sends the request to other parts in the control device 102 according to the analytical result. Specifically, when the transmitted request is a request to send the Web page corresponding to the amino acid concentration data transmission screen, mainly the browsing processing part 102*b* in the stress-evaluating apparatus 100 obtains the Web data for display of the Web page stored in a predetermined region of the memory device 106 and sends the obtained Web data to the client apparatus 200. More specifically, upon receiving the Web page transmission request corresponding to the amino acid concentration data transmission screen by the user, the control device 102 in the stress-evaluating apparatus 100 demands input of user ID and user password from the user. If the user ID and password are input, the authentication-processing part 102*c* in the stress-evaluating apparatus 100 examines the input user ID and password by comparing them with the user ID and user password stored in the user information file 106*a* for authentication. Only when the user is authenticated, the browsing processing part 102*b* in the stress-evaluating apparatus 100 sends, to the client apparatus 200, the Web data for displaying the Web page corresponding to the amino acid concentration data transmission screen. The client apparatus 200 is identified with the IP (Internet Protocol) address transmitted from the client apparatus 200 together with the transmission request.

Then, the client apparatus 200 receives, in the receiving part 213, the Web data (for displaying the Web page corresponding to the amino acid concentration data transmission screen) transmitted from the stress-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 sends an identifier for identifying input information and selected items to the stress-evaluating apparatus 100, thereby transmitting the amino acid concentration data of the individual as the subject to be evaluated to the stress-evaluating apparatus 100 (step SA-21). In step SA-21, transmission of the amino acid concentration data may be realized for example by using an existing file transfer technology such as FTP (File Transfer Protocol).

Then, the request-interpreting part 102a of the stress-evaluating apparatus 100 interprets the identifier transmitted from the client apparatus 200 thereby analyzing the request from the client apparatus 200, and requests the database apparatus 400 to send the multivariate discriminant for stress evaluation (specifically for discrimination of the 2 groups of depressive illness and non-depressive illness and for discrimination between the 2 groups of major depressive illness and non-major depressive illness) containing at least one of containing at least one of Lys, His, ABA, Asn, Phe, Leu, Ile, Val, Trp, Tyr and Met as variables.

Then, the request-interpreting part 402a of the database apparatus 400 interprets the transmission request from the stress-evaluating apparatus 100 and transmits, to the stress-evaluating apparatus 100, the multivariate discriminant (for example, the updated newest multivariate discriminant) containing at least one of Lys, His, ABA, Asn, Phe, Leu, Ile, Val, Trp, Tyr and Met as variable, stored in a predetermined region of the memory device 406 (step SA-22).

In step SA-22, the multivariate discriminant may be expressed by one fractional expression or the sum of a plurality of the fractional expressions and may contain at least one of Lys, His, ABA, Asn, Phe, Leu, Ile, Val, Trp, Tyr and Met as the variable in any one of the numerator and denominator or both in the fractional expression constituting the multivariate discriminant, or the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, when discriminating between depressive illness and non-depressive illness in after-mentioned step SA-26, the multivariate discriminant may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

When discriminating between major depressive illness and non-major depressive illness in after-mentioned step SA-26, the multivariate discriminant may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions and may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

Returning to FIG. 21, the stress-evaluating apparatus 100 receives, in the receiving part 102f, the amino acid concentration data of the individual transmitted from the client apparatuses 200, receives the multivariate discriminant transmitted from the database apparatus 400, stores the received amino acid concentration data in a predetermined memory region of the amino acid concentration data file 106b, and stores the received multivariate discriminant in a predetermined memory region of a multivariate discriminant file 106e4 (step SA-23).

In the control device 102 of the stress-evaluating apparatus 100, data such as defective and outliers are then removed from the amino acid concentration data of the individual received in step SA-23 (step SA-24).

Then, the stress-evaluating apparatus 100 calculates a discriminant value in the discriminant value-calculating part 102i, based on the multivariate discriminant received in step SA-23 and at least one concentration of Lys, His, ABA, Asn, Phe, Leu, Ile, Val, Trp, Tyr and Met contained in the amino acid concentration data of the individual from which defective and outliers have been removed in step SA-24 (step SA-25).

Then, the discriminant value criterion-discriminating part 102j1 of the stress-evaluating apparatus 100 compares the discriminant value calculated in step SA-25 with a previously established threshold (cutoff value), thereby discriminating between depressive illness and non-depressive illness and between major depressive illness and non-major depressive illness in the subject to be evaluated, and the discrimination results are stored in a predetermined memory region of the evaluation result file 106g (step SA-26).

The sending part 102*m* of the stress-evaluating apparatus 100 then sends the discrimination results (discrimination results as to discrimination between depressive illness and non-depressive illness or discrimination results as to discrimination between major depressive illness and non-major depressive illness) obtained in step SA-26 to the client apparatus 200 that has sent the amino acid concentration data and to the database apparatus 400 (step SA-27). Specifically, the stress-evaluating apparatus 100 first generates a Web page for display of discrimination results in the Web page-generating part 102*e* and stores the Web data corresponding to the generated Web page, in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the stress-evaluating apparatus 100. The stress-evaluating apparatus 100 then examines the browsing request transmitted from the client apparatus 200 in the browsing processing part 102*b* and reads the Web data corresponding to the Web page for displaying the discrimination results, out of the predetermined memory region of the memory device 106. The sending part 102*m* of the stress-evaluating apparatus 100 then sends the read-out Web data to the client apparatus 200 and simultaneously sends the Web data or the discrimination results to the database apparatus 400.

In step SA-27, the control device 102 of the stress-evaluating apparatus 100 may notify the discrimination results to the user client apparatus 200 by electronic mail. Specifically, the stress-evaluating apparatus 100 first acquires the user electronic mail address in the electronic mail-generating part 102*d* at the transmission timing for example based on the user ID, with reference to the user information stored in the user information file 106*a*. The stress-evaluating apparatus 100 then generates electronic mail data including user name and discrimination result, with the electronic mail address obtained as its mail address in the electronic mail-generating part 102*d*. The sending part 102*m* of the stress-evaluating apparatus 100 then sends the generated data to the user client apparatus 200.

Also in step SA-27, the stress-evaluating apparatus 100 may send the discrimination results to the user client apparatus 200 by using an existing file transfer technology such as FTP.

Returning to FIG. 21, the control device 402 in the database apparatus 400 receives the discrimination results or the Web data transmitted from the stress-evaluating apparatus 100 and stores (accumulates) the received discrimination results or Web data in a predetermined memory region of the memory device 406 (step SA-28).

The receiving part 213 of the client apparatus 200 receives the Web data transmitted from the stress-evaluating apparatus 100, and the received Web data are interpreted with the Web browser 211, to display on the monitor 261 the Web page screen displaying the discrimination result of the individual (step SA-29). When the discrimination results are sent from the stress-evaluating apparatus 100 by electronic mail, the electronic mail transmitted from the stress-evaluating apparatus 100 is received at any timing, and the received electronic mail is displayed on the monitor 261 with the known function of the electronic mailer 212 of the client apparatus 200.

In this way, the user knows discrimination results as to discrimination of 2 groups of depressive illness and non-depressive illness or discrimination results as to discrimination of 2 groups of major depressive illness and non-major depressive illness, in the individual, by browsing the Web page displayed on the monitor 261. The user can print out the content of the Web page displayed on the monitor 261 by a printer 262.

When the discrimination results are transmitted by electronic mail from the stress-evaluating apparatus 100, the user reads the electronic mail displayed on the monitor 261, whereby the user can confirm discrimination results as to discrimination of 2 groups of depressive illness and non-depressive illness or discrimination results as to discrimination of 2 groups of major depressive illness and non-major depressive illness, in the individual. The user may print out the content of the electronic mail displayed on the monitor 261 by the printer 262.

Given the foregoing description, the explanation of the stress evaluation service processing is finished.

2-4. Summary of the Second Embodiment and Other Embodiments

According to the stress-evaluating system described above in detail, the client apparatus 200 sends the amino acid concentration data of the individual to the stress-evaluating apparatus 100, and upon receiving a request from the stress-evaluating apparatus 100, the database apparatus 400 transmits the multivariate discriminant for discrimination between 2 groups of depressive illness and non-depressive illness or for discrimination between 2 groups of major depressive illness and non-major depressive illness, to the stress-evaluating apparatus 100. By the stress-evaluating apparatus 100, (1) amino acid concentration data are received from the client apparatus 200, and simultaneously the multivariate discriminant is received from the database apparatus 400, (2) data such as defective and outliers are removed from the received amino acid concentration data of the individual, (3) a discriminant value is calculated based on at least one concentration value of Lys, His, ABA, Asn, Phe, Leu, Ile, Val, Trp, Tyr and Met contained in the amino acid concentration data of the individual from which defective and outliers have been removed and the received multivariate discriminant, (4) the calculated discriminant value is compared with a previously established threshold, thereby discriminating between depressive illness and non-depressive illness or between major depressive illness and non-major depressive illness, in the individual, and (5) this discrimination result is transmitted to the client apparatus 200 and database apparatus 400. Then, the client apparatus 200 receives and displays the discrimination result transmitted from the stress-evaluating apparatus 100, and the database apparatus 400 receives and stores the discrimination result transmitted from the stress-evaluating apparatus 100. Thus, a discriminant value obtained in a multivariate discriminant using amino acid variables useful for discriminating between the 2 groups of depressive illness and non-depressive illness and between the 2 groups of major depressive illness and non-major depressive illness can be utilized to bring about an effect of enabling accurate discrimination between the 2 groups of depressive illness and non-depressive illness and between the 2 groups of major depressive illness and non-major depressive illness.

When discriminating between depressive illness and non-depressive illness in step SA-26, the multivariate discriminant may be formula 1 or 2 below, or a logistic regression equation with Ser, Glu, Cys and Lys as variables or a linear discriminant with Ser, Glu, Cys and Lys as variables. The multivariate discriminant may be expressed by one fractional expression or the sum of a plurality of the fractional expressions may contain either at least one of Cys, Glu, Tyr and Phe as the variable in the numerator and at least one of Asn, Tau and Lys as the variable in the denominator or at least one of Asn, Tau and Lys as the variable in the numerator and at least one of Cys, Glu, Tyr and Phe as the variable in the denominator, in the fractional expression constituting the multivariate discriminant. Thus, a discriminant value obtained in a multivariate discriminant using amino acid variables useful particularly for discriminating between the 2 groups of depressive illness and non-depressive illness can be utilized to bring about an effect of enabling more accurate discrimination between the 2 groups of depressive illness and non-depressive illness.

$$a_1 \times Cys/Asn + b_1 \times (Glu+Tyr+Phe)/(Tau+Lys) + c_1 \quad \text{(formula 1)}$$

$$a_2 \times Glu/Lys + b_2 \times Met/(Tyr+Phe+Trp) + c_2 \times Ile/Leu + d_2 \times Phe/(Val+Leu+Ile+Tyr+Phe+Trp) + e_2 \quad \text{(formula 2)}$$

wherein $a_1$, $b_1$ and $c_1$ in formula 1 are arbitrary real numbers, and $a_2$, $b_2$, $c_2$, $d_2$, and $e_2$ in formula 2 are arbitrary real numbers.

When discriminating between major depressive illness and non-major depressive illness in after-mentioned step SA-26, the multivariate discriminant may be formula 3, 4, 5, 6 or 7 below, or a logistic regression equation with Ser, Gln, Pro, ABA, Tyr and Trp as the variables, a logistic regression equation with Glu, Asn, Gln, Cit and ABA as the variables, a linear discriminant with Ser, Gln, Pro, ABA, Cys, Ile, Tyr and Trp as the variables or a linear discriminant with Asn, Gln, Tau, Cit and ABA as the variables. The multivariate discriminant may be expressed by one fractional expression or the sum of a plurality of the fractional expressions and may contain either at least one of Phe, Glu and Ser as the variable in the numerator and at least one of Tau, Thr, Val and Lys as the variable in the denominator or at least one of Tau, Thr, Val and Lys as the variable in the numerator and at least one of Phe, Glu and Ser as the variable in the denominator, in the fractional expression constituting the multivariate discriminant. Thus, a discriminant value obtained in a multivariate discriminant using amino acid variables useful particularly for discriminating between the 2 groups of major depressive illness and non-major depressive illness can be utilized to bring about an effect of enabling more accurate discrimination between the 2 groups of major depressive illness and non-major depressive illness.

$$a_3 \times Phe/(Tau+Thr) + b_3 \times (Glu+Ser)/(Val+Lys) + c_3 \quad \text{(formula 3)}$$

$$a_4 \times Gly/Gln + b_4 \times (Glu+Pro+Ile)/(Orn+Trp+ABA) + c_4 \quad \text{(formula 4)}$$

$$a_5 \times Asn + b_5 \times Ala/Trp + c_5 \times ABA/Tyr + d_5 \times Ser/Val + e_5 \quad \text{(formula 5)}$$

$$a_6 \times (Glu+Gln)/(Val+Thr+Ser) + b_6 \times (Cit+Met)/Asn + c_6 \quad \text{(formula 6)}$$

$$a_7 \times Asn/Gln + b_7 \times Cit/ABA + c_7 \times Glu/Arg + d_7 \times Met/(Val+Leu+Ile) + e_7 \quad \text{(formula 7)}$$

wherein $a_3$, $b_3$ and $c_3$ in formula 3 are arbitrary real numbers, $a_4$, $b_4$, and $c_4$ in formula 4 are arbitrary real numbers, $a_5$, $b_5$, $c_5$, $d_5$ and $e_5$ in formula 5 are arbitrary real numbers, $a_6$, $b_6$, and $c_6$ in formula 6 are arbitrary real numbers, and $a_7$, $b_7$, $c_7$, $d_7$ and $e_7$ in formula 7 are arbitrary real numbers.

The multivariate discriminants described above can be prepared by a method described in International Publication WO 2004/052191 that is an international application filed by the present applicant or by a method (multivariate discriminant-preparing processing described in the second embodiment described later) described in International Publication PCT/JP2006/304398 that is an international application filed by the present applicant. Any multivariate discriminants obtained by these methods can be preferably used in evaluation of a stress state, regardless of the unit of amino acid concentration in the amino acid concentration data as input data.

In addition to the second embodiment described above, the stress-evaluating apparatus, the stress-evaluating method, the stress-evaluating system, the stress-evaluating program and the recording medium according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the stress-evaluating apparatus 100 shown in the figures are conceptual and functional and may not be the same physically as those shown in the figure. In addition, all or a part of the operational function of each component and each device in the stress-evaluating apparatus 100 (in particular, processings in control device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may not be configured singly, and may be operated together with plurality of modules and libraries or with a different program such as OS (Operating System) to achieve the function. The program is stored on a recording medium and read mechanically as needed by the stress-evaluating apparatus 100. Any well-known configuration or procedure may be used for reading the programs recorded on the recording medium in each apparatus and for reading procedure and installation of the procedure after reading.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), and the like. Examples of the "fixed physical media" include various media installed in a computer system such as ROM, RAM, and HD. The "communication media" for example stores the program for a short period of time such as communication line and carrier wave when the program is transmitted via a network such as LAN (Local Area Network), WAN (Wide Area Network), or the Internet.

Figure 22:
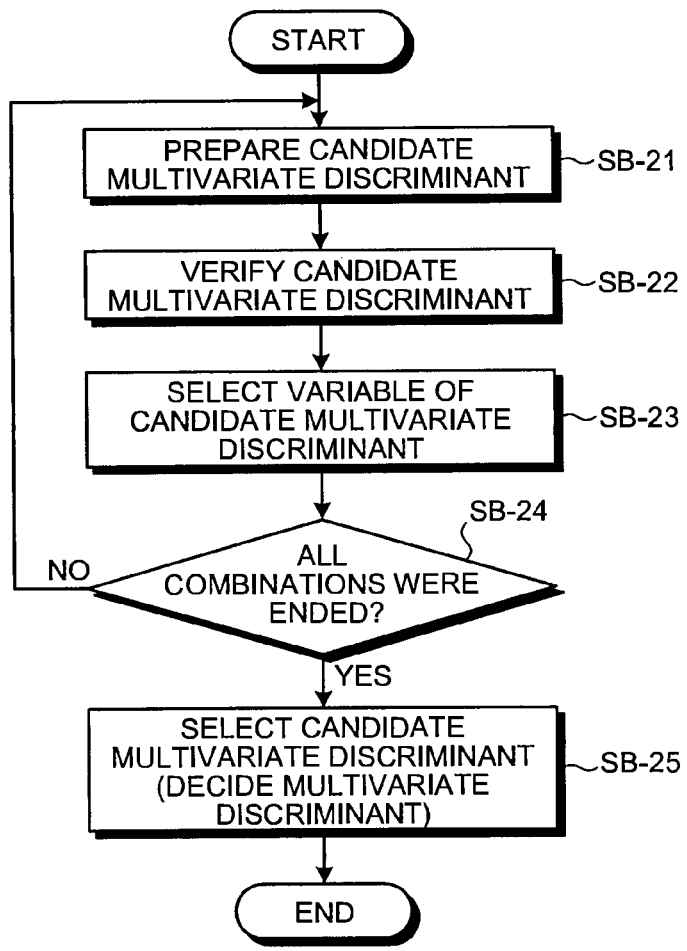
FIG. 22 is a flowchart showing an example of the multivariate discriminant-preparing processing performed in the stress-evaluating apparatus 100 in the present system.

Finally, an example of the multivariate discriminant-preparing processing performed in the stress-evaluating apparatus 100 is described in detail with reference to FIG. 22. FIG. 22 is a flowchart showing an example of the multivariate discriminant-preparing processing. The multivariate discriminant-preparing processing may be performed in the database apparatus 400 handling the stress state information.

In the present description, the stress-evaluating apparatus 100 stores the stress state information previously obtained from the database apparatus 400 in a predetermined memory region of the stress state information file 106c. The stress-evaluating apparatus 100 shall store, in a predetermined memory region of the designated stress state information file 106*d*, the stress state information including the stress state index data and amino acid concentration data designated previously in the stress state information-designating part 102*g*.

According to a predetermined discriminant-preparing method, the candidate multivariate discriminant-preparing part 102*h*1 in the multivariate discriminant-preparing part 102*h* first prepares a candidate multivariate discriminant from the stress state information stored in a predetermine memory region of the designated stress state information file 106*d*, and the prepared candidate multivariate discriminate is stored in a predetermined memory region of the candidate multivariate discriminant file 106*e*1 (step SB-21). Specifically, the candidate multivariate discriminant-preparing part 102*h*1 in the multivariate discriminant-preparing part 102*h* first selects a desired method out of a plurality of different discriminant-preparing methods (including multivariate analysis methods such as principal component analysis, discriminant analysis, support vector machine, multiple regression analysis, logistic regression analysis, k-means method, cluster analysis, and decision tree and the like) and determines the form of the candidate multivariate discriminant to be prepared based on the selected discriminant-preparing method. The candidate multivariate discriminant-preparing part 102*h*1 in the multivariate discriminant-preparing part 102*h* then performs various calculation corresponding to the selected function-selecting method (e.g., average or variance), based on the stress state information. The candidate multivariate discriminant-preparing part 102*h*1 in the multivariate discriminant-preparing part 102*h* then determines the parameters for the calculation result and the determined candidate multivariate discriminant. In this way, a candidate multivariate discriminant is generated based on the selected discriminant-preparing method. When candidate multivariate discriminants are generated simultaneously and concurrently (in parallel) by using a plurality of different discriminant-preparing methods in combination, the processings described above may be executed concurrently for each selected discriminant-preparing method. Alternatively when candidate multivariate discriminants are to be generated in series by using a plurality of different discriminant-preparing methods in combination, for example, candidate multivariate discriminants may be generated by converting stress state information with a candidate multivariate discriminant prepared by performing principal component analysis and performing discriminant analysis of the converted stress state information.

The candidate multivariate discriminant-verifying part 102*h*2 in the multivariate discriminant-preparing part 102*h* verifies (mutually verifies) the candidate multivariate discriminant prepared in step SB-21 according to a particular verification method and stores the verification result in a predetermined memory region of verification result file 106*e*2 (step SB-22). Specifically, the candidate multivariate discriminant-verifying part 102*h*2 in the multivariate discriminant-preparing part 102*h* first generates the verification data to be used in verification of the candidate multivariate discriminant, based on the stress state information stored in a predetermined memory region of the designated stress state information file 106*d*, and verifies the candidate multivariate discriminant according to the generated verification data. If a plurality of candidate multivariate discriminants are generated by using a plurality of different discriminant-preparing methods in step SB-21, the candidate multivariate discriminant-verifying part 102*h*2 in the multivariate discriminant-preparing part 102*h* verifies each candidate multivariate discriminant corresponding to each discriminant-preparing method according to a particular verification method. Here in step SB-22, at least one of the discrimination rate, sensitivity, specificity, information criterion, and the like of the candidate multivariate discriminant may be verified based on at least one method of the bootstrap, holdout, leave-one-out, and other methods. Thus, it is possible to select a candidate multivariate discriminant higher in predictability or reliability, based on the stress state information and diagnostic condition.

Then, the variable-selecting part 102*h*3 in the multivariate discriminant-preparing part 102*h* selects the combination of amino acid concentration data contained in the stress state information to be used in preparing the candidate multivariate discriminant by selecting a variable of the candidate multivariate discriminant from the verification results in step SB-22 according to a particular variable selection method, and stores the stress state information including the selected combination of amino acid concentration data in a predetermined memory region of the selected stress state information file 106*e*3 (step SB-23). When a plurality of candidate multivariate discriminants are generated by using a plurality of different discriminant-preparing methods in step SB-21 and each candidate multivariate discriminant corresponding to each discriminant-preparing method is verified according to a particular verification method in step SB-22, the variable-selecting part 102*h*3 in the multivariate discriminant-preparing part 102*h* selects the variable of the candidate multivariate discriminant for each candidate multivariate discriminant corresponding to the verification result obtained in step SB-22, according to a particular variable selection method in step SB-23. Here in step SB-23, the variable of the candidate multivariate discriminant may be selected from the verification results according to at least one of stepwise method, best path method, local search method, and genetic algorithm. The best path method is a method of selecting a variable by optimizing the evaluation index of the candidate multivariate discriminant while eliminating the variables contained in the candidate multivariate discriminant one by one. In step SB-23, the variable-selecting part 102*h*3 in the multivariate discriminant-preparing part 102*h* may select the combination of amino acid concentration data based on the stress state information stored in a predetermined memory region of the designated stress state information file 106*d*.

The multivariate discriminant-preparing part 102*h* then judges whether all combinations of the amino acid concentration data contained in the stress state information stored in a predetermined memory region of the designated stress state information file 106*d* are processed, and if the judgment result is "End" (Yes in step SB-24), the processing advances to the next step (step SB-25), and if the judgment result is not "End" (No in step SB-24), it returns to step SB-21. The multivariate discriminant-preparing part 102*h* judges whether the processing is performed a predetermined number of times, and if the judgment result is "End" (Yes in step SB-24), the processing may advance to the next step (step SB-25), and if the judgment result is not "End" (No in step SB-24), it returns to step SB-21. The multivariate discriminant-preparing part 102*h* may judge whether the combination of the amino acid concentration data selected in step SB-23 is the same as the combination of the amino acid concentration data contained in the stress state information stored in a predetermined memory region of the designated stress state information file 106*d* or the combination of the amino acid concentration data selected in the previous step SB-23, and if the judgment result is "the same" (Yes in step SB-24), the processing may advance to the next step (step SB-25) and if the judgment result is not "the same" (No in step SB-24), it may return to step SB-21. If the verification result is specifically the evaluation value for each multivariate discriminant, the multivariate discriminant-preparing part 102h may advance to step SB-25 or return to step SB-21, based on the comparison of the evaluation value with a particular threshold corresponding to each discriminant-preparing method.

Then, the multivariate discriminant-preparing part 102h determines the multivariate discriminant based on the verification results by selecting a candidate multivariate discriminant to be used as the multivariate discriminant among the candidate multivariate discriminants, and stores the determined multivariate discriminant (selected candidate multivariate discriminant) in particular memory region of the multivariate discriminant file 106e4 (step SB-25). Here, in step SB-25, for example, the optimal multivariate discriminant may be selected from the candidate multivariate discriminants prepared by the same discriminant-preparing method or from all candidate multivariate discriminants.

These are description of the multivariate discriminant-preparing processing.

EXAMPLE 1

Figure 23:
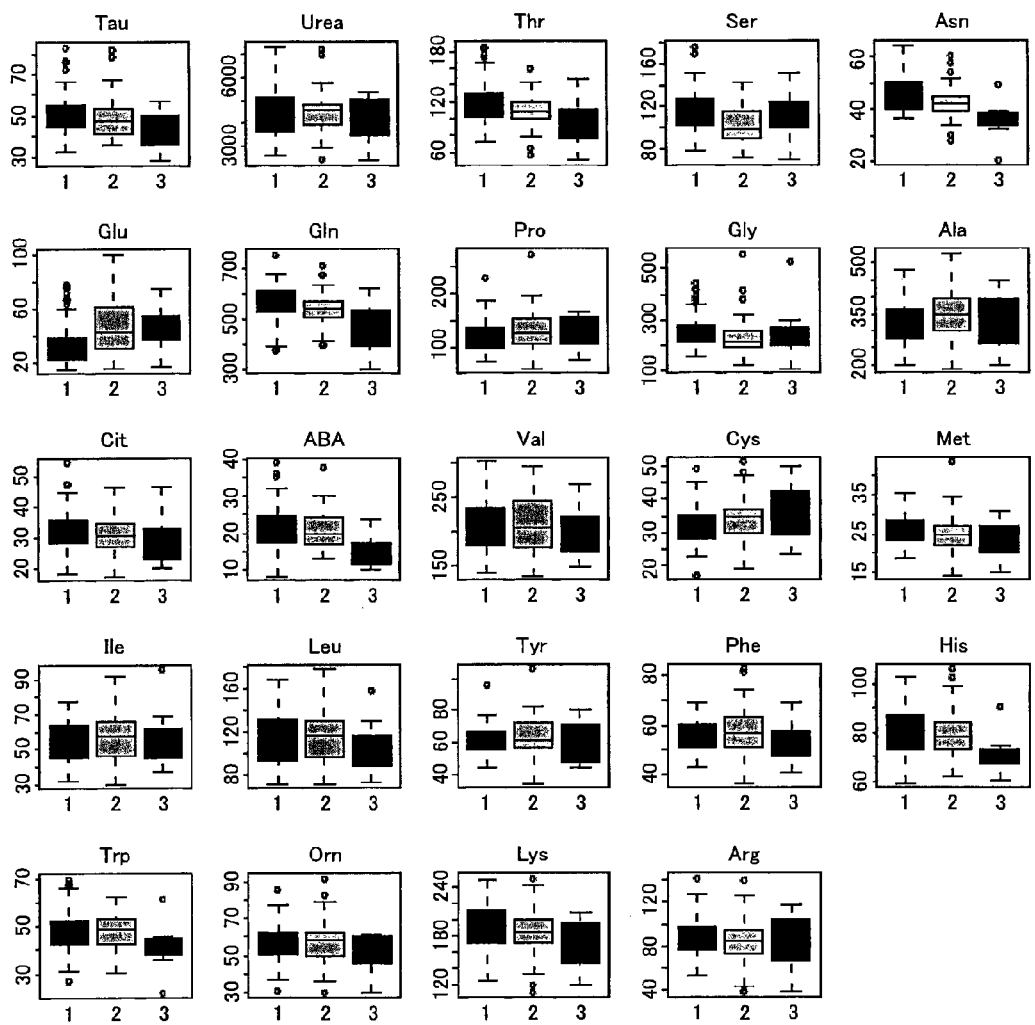
FIG. 23 is a boxplot showing the distribution of amino acid variables among 3 groups of a healthy group, a group with finding of depressive illness and a group with finding of major depressive illness.

From blood samples of a healthy group and a group with finding of stress judged as depressive illness or major depressive illness by results in checking, the concentrations of amino acids in blood were measured by the amino acid analysis method described above. FIG. 23 is a boxplot showing the distribution of amino acid variables in each of the groups (1: healthy group, 2: group with finding of depressive illness, 3: group with finding of major depressive illness) (ordinate: nmol/ml, ABA in the graph is α-ABA, and Cys is Cystine).

The method of diagnosing depressive illness uses the results (that is, in at least one of the following items a to f) in inquiry items corresponding to the items a to f indicative of depressed mood in a professional simplified stress survey sheet to judge depressive illness.
a: Feels gloomy.
b: Feels difficulty in doing anything.
c: Has difficulty in concentrating.
d: Feels depressed.
e: Not feel like working.
f: Feels sad.

The method of diagnosing major depressive illness judges a subject as major depressive illness when the conditions in at least 5 of the following 9 items (A to I) in DSM-IV continue simultaneously for 2 weeks or more.
A: Feels low most of the day.
B: Not interested in anything and not feel comfortable.
C: Loss of appetite or significant increase and decrease in body weight.
D: Has difficulty in sleeping. Awakened at midnight and early morning.
E: Slow in action and speech or seems frustrated or restless.
F: Feels fatigue and feels low.
G: Feels no value in oneself or feels guilty.
H: Cannot focus on one's work or household work and cannot make a decision.
I: Wishes sometimes to disappear from the earth.

For the purpose of discrimination between 2 groups of a healthy group and a group with finding of depressive illness judged as depressive illness, Mann-Whitney test, that is, nonparametric analysis of the 2 groups was carried out. In the group with finding of depressive illness as compared with the healthy group, Lys was significantly decreased (significant difference probability $P<0.05$), and it was revealed that the amino acid variable Lys has an ability to discriminate the 2 groups of a healthy group and a group with finding of depressive illness.

For the purpose of discrimination between 2 groups of a healthy group and a group with finding of major depressive illness, Mann-Whitney test, that is, nonparametric analysis of the 2 groups was carried out. In the group with finding of major depressive illness as compared with the healthy group, Lys, His, ABA and Asn were significantly decreased (significant difference probability $P<0.05$), and it was revealed that the amino acid variables Lys, His, ABA and Asn have an ability to discriminate the 2 groups of a healthy group and a group with finding of major depressive illness.

EXAMPLE 2

With reference to a logistic regression equation and linear discriminant as an example of multivariate discriminant, a discriminant for a healthy group and a group with finding of stress (depressive illness and major depressive illness) was derived from the sample data used in Example 1. The "multivariate discriminant for a healthy group and a group with finding of stress (depressive illness and major depressive illness)" in this embodiment refers to a formula obtained from discrimination analysis results by logistic regression analysis, linear discriminant analysis, Mahalanobis' generalized distance, support vector machine, canonical discriminant analysis, decision tree, or the like.

First, a multivariate discriminant for maximizing the performance of discriminating the 2 groups of a healthy group and a group with finding of depressive illness was searched by logistic analysis (variable selection by a stepwise method of Wald test) to give a logistic regression equation composed of Ser, Glu, Cys and Lys as an index (numerical coefficients of amino acid variables Ser, Glu, Cys and Lys and the constant term were −0.03, 0.04, 0.10, −0.02, and 2.52, respectively). Besides, a plurality of logistic regression equations having the same discrimination performance were obtained. These are shown in FIGS. 24, 25 and 26. The values of coefficients in the formulae in FIGS. 24, 25 and 26 may be those multiplied by a real number.

Figure 27:
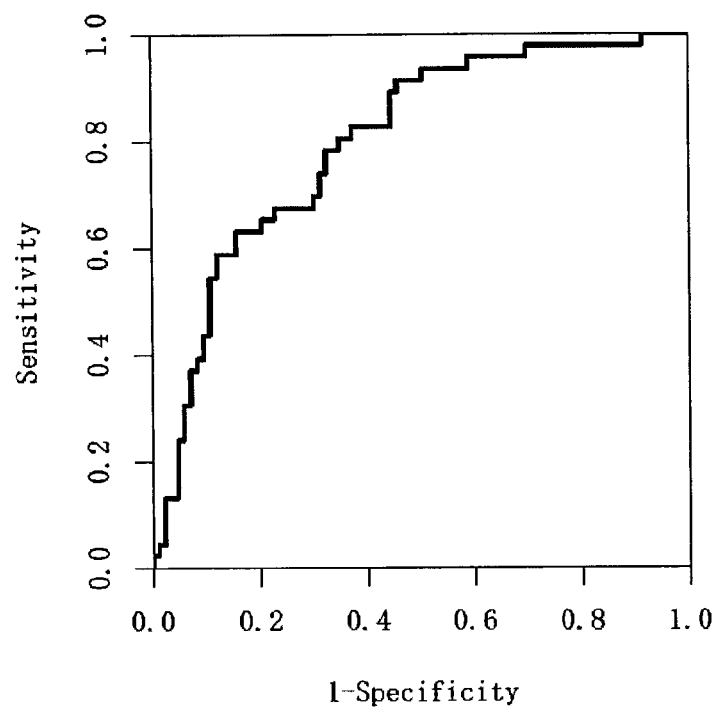
FIG. 27 is a graph showing a ROC curve for evaluation of diagnostic performance between the 2 groups of a healthy group and a group with finding of depressive illness.

Discrimination of the 2 groups of a healthy group and a group with finding of depressive illness by this index was evaluated by the AUC (area under the curve) of the ROC (receiver operating characteristic) curve (FIG. 27), to give an AUC of 0.796±0.038 (95% confidence interval: 0.721 to 0.872), and this index was revealed to be an useful index with high diagnostic performance.

Then, a multivariate discriminant for maximizing the performance of discriminating the 2 groups of a healthy group and a group with finding of major depressive illness was searched by logistic analysis (variable selection by a stepwise method of Wald test) to give a logistic regression equation composed of Ser, Gln, Pro, ABA, Tyr and Trp as an index (numerical coefficients of amino acid variables Ser, Gin, Pro, ABA, Tyr and Trp and the constant term were 0.2, −0.1, 0.4, −2.9, 1.1, −1.7 and 46.8, respectively). Besides, a plurality of logistic regression equations having the same discrimination performance were obtained. These are shown in FIGS. 28, 29 and 30. The values of coefficients in the formulae in FIGS. 28, 29 and 30 may be those multiplied by a real number.

Figure 31:
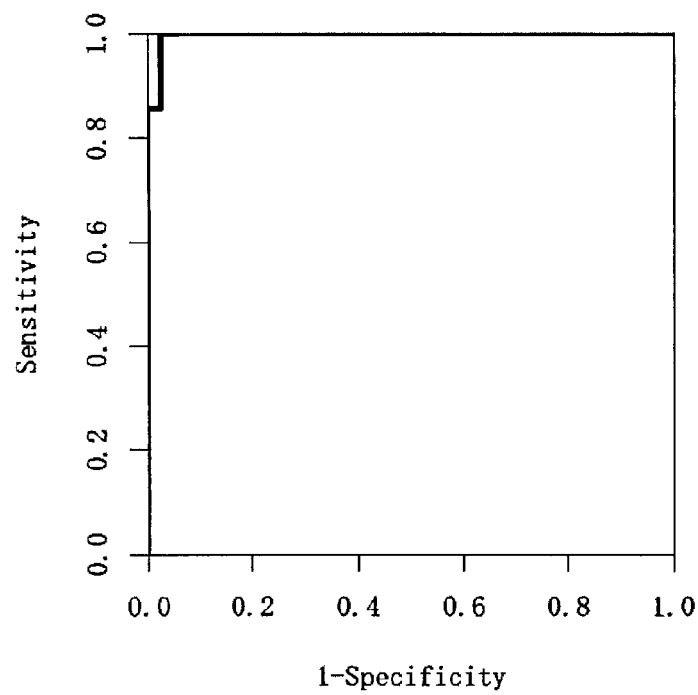
FIG. 31 is a graph showing a ROC curve for evaluation of diagnostic performance between the 2 groups of a healthy group and a group with finding of major depressive illness.

Discrimination of the 2 groups of a healthy group and a group with finding of major depressive illness by this index was evaluated by the AUC of the ROC curve (FIG. 31), to give an AUC of 0.997±0.005 (95% confidence interval: 0.987 to 1.000), and this index was revealed to be an useful index with high diagnostic performance.

Further, a multivariate discriminant for maximizing the performance of discriminating the 2 groups of a healthy group and a group with finding of depressive illness was searched by linear discriminant analysis (variable selection by a stepwise method) to give a discriminant composed of Ser, Glu, Cys and Lys an index (numerical coefficients of amino acid variables Ser, Glu, Cys and Lys and the constant term were −0.03, 0.03, 0.09, −0.02 and 2.47, respectively). Besides, a plurality of linear discriminants having the same discrimination performance were obtained. These are shown in FIGS. 32, 33 and 34. The values of coefficients in the formulae in FIGS. 32, 33 and 34 may be those multiplied by a real number.

Figure 35:
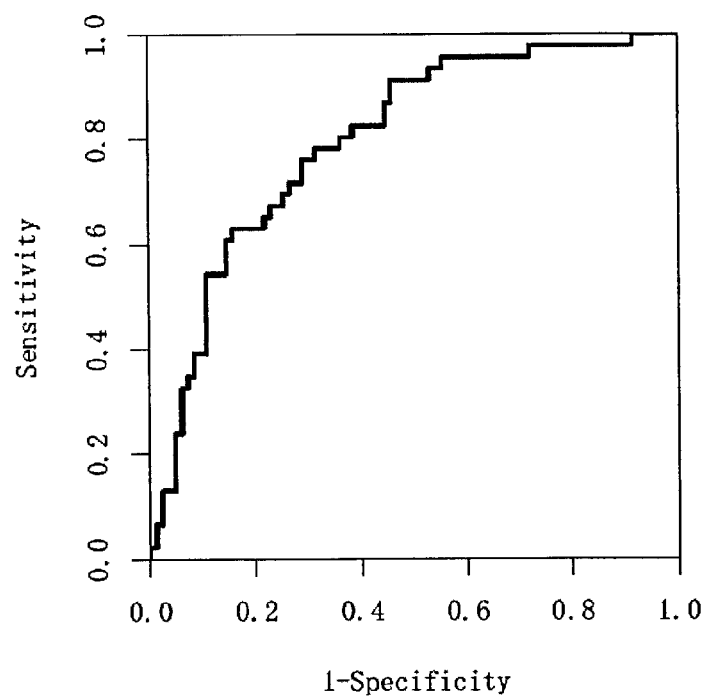
FIG. 35 is a graph showing a ROC curve for evaluation of diagnostic performance between the 2 groups of a healthy group and a group with finding of depressive illness.

Discrimination of the 2 groups of a healthy group and a group with finding of depressive illness by this index was evaluated by the AUC of the ROC curve (FIG. 35), to give an AUC of 0.798±0.038 (95% confidence interval: 0.723 to 0.873), and this index was revealed to be an useful index with high diagnostic performance.

In addition, a multivariate discriminant for maximizing the performance of discriminating the 2 groups of a healthy group and a group with finding of major depressive illness was searched by linear discriminant analysis (variable selection by a stepwise method) to give a discriminant composed of Ser, Gln, Pro, ABA, Cys, Ile, Tyr and Trp as an index (numerical coefficients of amino acid Ser, Gln, Pro, ABA, Cys, Ile, Tyr and Trp and the constant term were −0.02, 0.02, −0.01, 0.11, −0.08, −0.04, −0.04, 0.10 and −5.77, respectively). Besides, a plurality of linear discriminants having the same discrimination performance were obtained. These are shown in FIGS. 36, 37 and 38. The values of coefficients in the formulae in FIGS. 36, 37 and 38 may be those multiplied by a real number.

Figure 39:
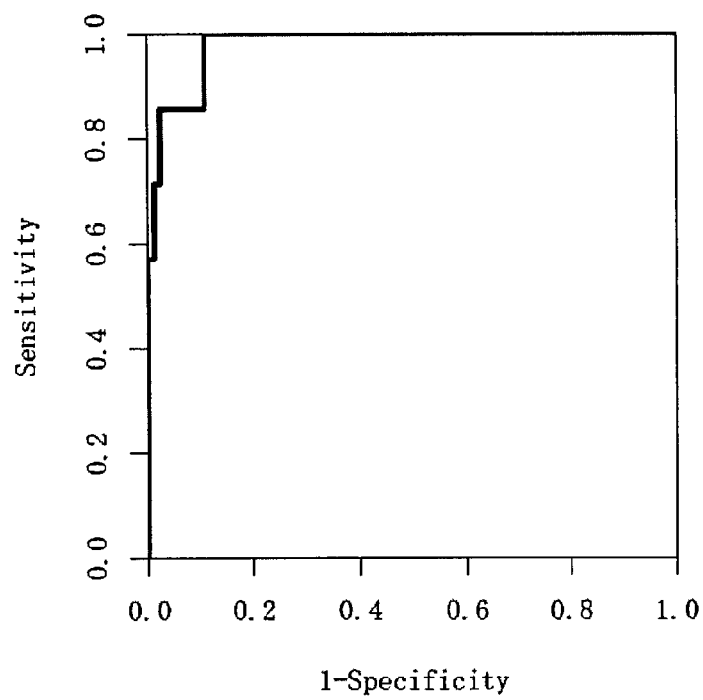
FIG. 39 is a graph showing a ROC curve for evaluation of diagnostic performance between the 2 groups of a healthy group and a group with finding of major depressive illness.

Discrimination of the 2 groups of a healthy group and a group with finding of major depressive illness by this index was evaluated by the AUC of the ROC curve (FIG. 39), to give an AUC of 0.979±0.014 (95% confidence interval: 0.952 to 1.000), and this index was revealed to be an useful index with high diagnostic performance.

From the foregoing results, it was revealed that a formula for accurate discrimination between a healthy group and a group with finding with stress can be derived from the generally used multivariable analysis method. As the variables in the multivariate discriminant for a healthy group and a group with finding of stress, non-amino acid data such as metabolome data (organic acid, fatty acid, nucleic acid etc.), transcriptome data, and proteome data can also be used in addition to amino acid variables in order to improve discrimination performance.

EXAMPLE 3

The sample data used in Example 1 were used. Using a method described in International Publication WO 2004/052191 that is an international application filed by the present applicant, an index for maximizing the performance of discriminating the 2 groups of a healthy group and a group with finding of depressive illness was extensively searched to give index 1 in a plurality of indices having the same performance. Besides, a plurality of multivariate discriminants having the same discrimination performance as that of the index 1 were obtained. These are shown in FIGS. 40, 41 and 42.
Index 1: (Cys)/(Asn)+(Glu+Tyr+Phe)/(Tau+Lys)

Figure 43:
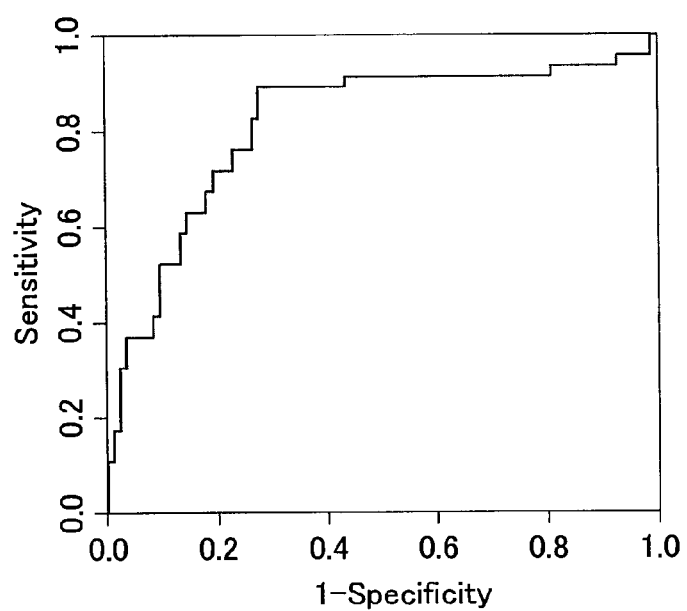
FIG. 43 is a graph showing a ROC curve for evaluation of diagnostic performance between the 2 groups of a healthy group and a group with finding of depressive illness.

Discrimination of the 2 groups a healthy group and a group with finding of depressive illness by the index 1 was evaluated by the AUC of the ROC curve (FIG. 43), to give an AUC of 0.813±0.037 (95% confidence interval: 0.741 to 0.885). When the optimum cutoff value for discrimination of the 2 groups of a healthy group and a group with finding of depressive illness by the index 1 was determined assuming that the incidence in the group with finding of depressive illness was 0.36, the cutoff value was 1.38, and the sensitivity was 89%; the specificity, 72%; and the correct diagnostic rate, 78%, and the index 1 was revealed to be an useful index with high diagnostic performance.

Then, an index for maximizing the performance of discriminating the 2 groups of a healthy group and a group with finding of major depressive illness was extensively searched to give indices 2 and 3 in a plurality of indices having the same performance. Besides, a plurality of multivariate discriminants having the same discrimination performance as that of the index 3 were obtained. These are shown in FIGS. 44, 45 and 46.
Index 2: (Phe)/(Tau+Thr)+(Glu+Ser)/(Val+Lys)
Index 3: (Gly)/(Gln)+(Glu+Pro+Ile)/(Orn+Trp+ABA)

Figure 47:
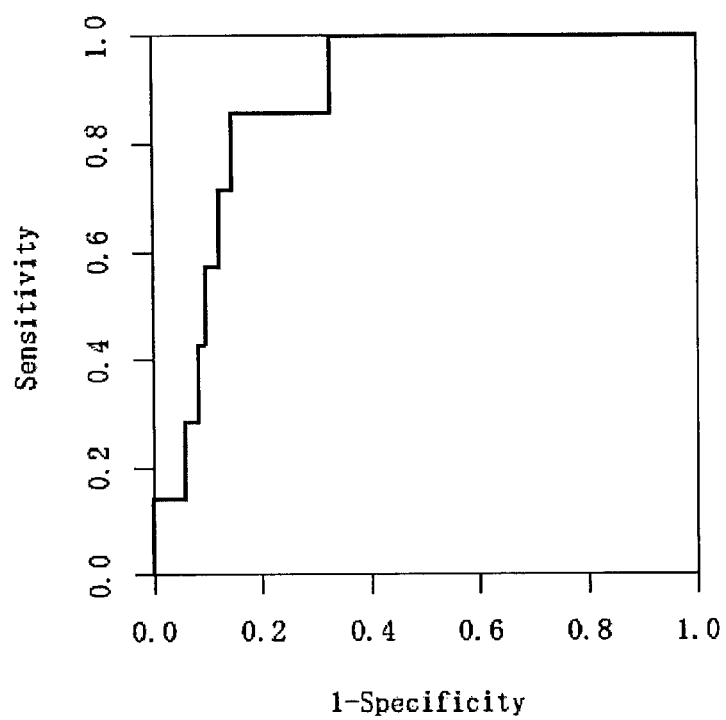
FIG. 47 is a graph showing a ROC curve for evaluation of diagnostic performance between the 2 groups of a healthy group and a group with finding of major depressive illness.

Discrimination of the 2 groups a healthy group and a group with finding of major depressive illness by the index 2 was evaluated by the AUC of the ROC curve (FIG. 47), to give an AUC of 0.881±0.047 (95% confidence interval: 0.709 to 0.974). When the optimum cutoff value for discrimination of the 2 groups of a healthy group and a group with finding of major depressive illness by the index 2 was determined assuming that the incidence in the group with finding of major depressive illness was 0.08, the cutoff value was 0.794, and the sensitivity was 86%; the specificity, 86%; and the correct diagnostic rate, 86%, and the index 2 was revealed to be an useful index with high diagnostic performance.

Figure 48:
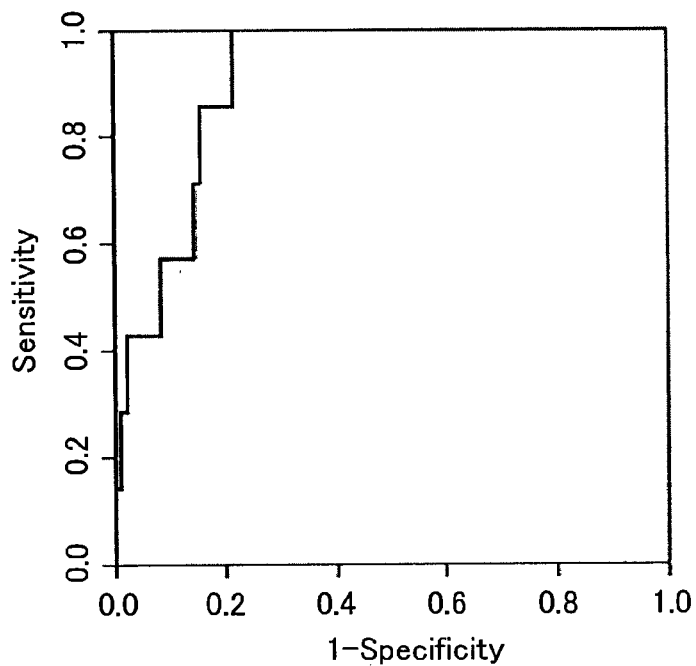
FIG. 48 is a graph showing a ROC curve for evaluation of diagnostic performance between the 2 groups of a healthy group and a group with finding of major depressive illness.

Discrimination of the 2 groups a healthy group and a group with finding of major depressive illness by the index 3 was evaluated by the AUC of the ROC curve (FIG. 48), to give an AUC of 0.909±0.039 (95% confidence interval: 0.832 to 0.985). When the optimum cutoff value for discrimination of the 2 groups of a healthy group and a group with finding of major depressive illness by the index 3 was determined assuming that the incidence in the group with finding of major depressive illness was 0.08, the cutoff value was 2.289, and the sensitivity was 86%; the specificity, 84%; and the correct diagnostic rate, 84%, and the index 3 was revealed to be an useful index with high diagnostic performance.

EXAMPLE 4

The sample data used in Example 1 were used. Using a method described in International Publication WO 2004/052191 that is an international application filed by the present applicant, an index for maximizing the performance of discriminating the 2 groups of a healthy group and a group with finding of depressive illness was extensively searched to give index 4 in a plurality of indices having the same performance.
Index 4: (Glu)/(Lys)+(−5.169)×(Met/AAA)+1.6769×(Ile/Leu)+5.5337×(Phe/LNAAs)

Figure 49:
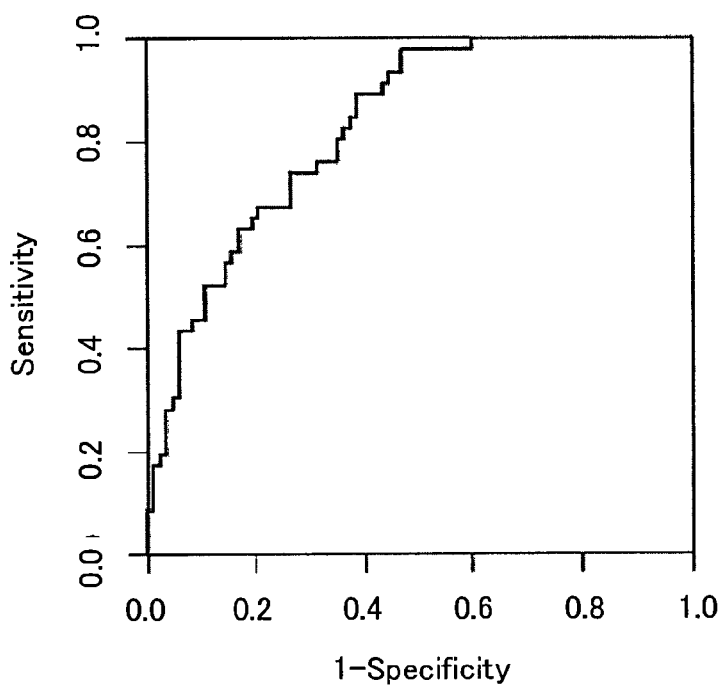
FIG. 49 is a graph showing a ROC curve for evaluation of diagnostic performance between the 2 groups of a healthy group and a group with finding of depressive illness.

Discrimination of the 2 groups a healthy group and a group with finding of depressive illness by the index 4 was evaluated by the AUC of the ROC curve (FIG. 49), to give an AUC of 0.827±0.035 (95% confidence interval: 0.758 to 0.897). When the optimum cutoff value for discrimination of the 2 groups of a healthy group and a group with finding of depressive illness by the index 4 was determined assuming that the incidence in the group with finding of depressive illness was 0.36, the cutoff value was 0.82, and the sensitivity was 74%; the specificity, 71%; and the correct diagnostic rate, 72%, and the index 4 was revealed to be an useful index with high diagnostic performance.

Then, an index for maximizing the performance of discriminating the 2 groups of a healthy group and a group with finding of major depressive illness was extensively searched to give index 5 in a plurality of indices having the same performance.

Index 5: (Asn)+(−2.8556)×(Ala/Trp)+48.6047×(ABA/Tyr)+(−8.4761)×(Ser/Val)

Figure 50:
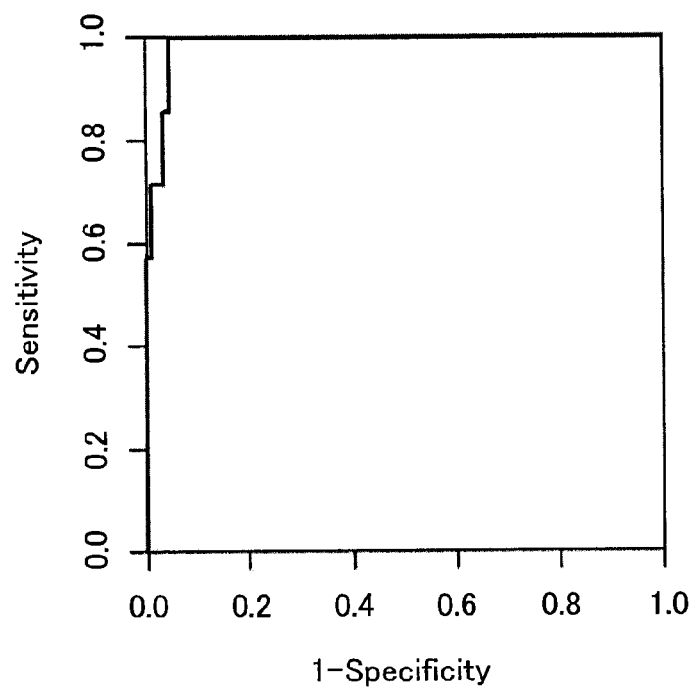
FIG. 50 is a graph showing a ROC curve for evaluation of diagnostic performance between the 2 groups of a healthy group and a group with finding of major depressive illness.

Discrimination of the 2 groups a healthy group and a group with finding of major depressive illness by the index 5 was evaluated by the AUC of the ROC curve (FIG. 50), to give an AUC of 0.986±0.011 (95% confidence interval: 0.965 to 1.000). When the optimum cutoff value for discrimination of the 2 groups of a healthy group and a group with finding of major depressive illness by the index 5 was determined assuming that the incidence in the group with finding of major depressive illness was 0.08, the cutoff value was 27.50, and the sensitivity was 86%; the specificity, 96%; and the correct diagnostic rate, 96%, and the index 5 was revealed to be an useful index with high diagnostic performance.

EXAMPLE 5

As the amino acid variables correlated with a stress level obtained in test results in a stress interview sheet from Tokyo Institute of Psychiatry, Phe, Leu, Ile, Val, Trp, Tyr, Met, BCAA, AAA, and LNAAs (significant difference probability P<0.05) showed a significant correlation (Pearson correlation), and the amino acid variables Phe, Leu, Ile, Val, Trp, Tyr, Met, BCAA, AAA, and LNAAs were revealed to have an ability to evaluate a stress level ranging from depressive illness to major depressive illness.

As the index for indicating a stress level, a stress interview sheet from Tokyo Institute of Psychiatry was used. Its index consists of 4 items, that is, physical and mental phenomenon, personality trait, type A characteristic, and stressor, and the respective items are scored in 3 ranks (point 0, 1 or 2) and added up to indicate a stress level.

EXAMPLE 6

The sample data used in Example 1 were used. Using a method described in International Publication WO 2004/052191 that is an international application filed by the present applicant, an index for maximizing the diagnostic performance of stress level state was extensively searched to give index 6 in a plurality of indices having the same performance.

Index 6: (Phe)+(−21.158)×(Cit/Glu)+6.9843×(Gly/His)

EXAMPLE 7

With reference to a logistic regression equation and linear discriminant as an example of multivariate discriminant, a discriminant for a healthy group and a group with finding of major depressive illness was derived. The "multivariate discriminant for a healthy group and a group with finding of major depressive illness" in this embodiment refers to a formula obtained from discrimination analysis results by logistic regression analysis, linear discriminant analysis, Mahalanobis' generalized distance, support vector machine, canonical discriminant analysis, decision tree, or the like.

First, a multivariate discriminant for maximizing the performance of discriminating the 2 groups of a healthy group and a group with finding of major depressive illness was searched by logistic analysis (variable selection by a stepwise method of Wald test) to give a logistic regression equation composed of Glu, Asn, Gln, Cit and ABA as an index (numerical coefficients of amino acid variables Glu, Asn, Gln, Cit and ABA and the constant term were 0.03, −0.17, 0.01, 0.11, −0.12 and −0.38, respectively). Besides, a plurality of logistic regression equations having the same discrimination performance were obtained. These are shown in FIGS. 51, 52 and 53. The values of coefficients in the formulae in FIGS. 51, 52 and 53 may be those multiplied by a real number.

Figure 54:
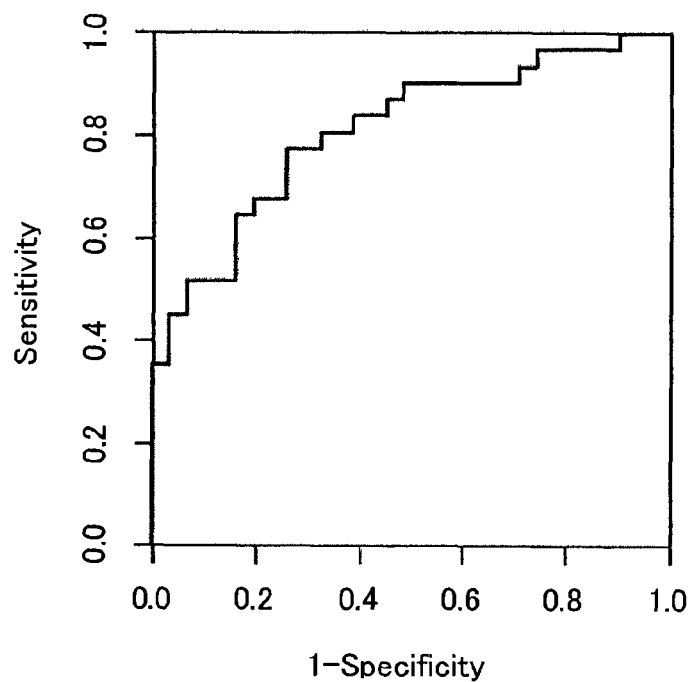
FIG. 54 is a graph showing a ROC curve for evaluation of diagnostic performance between the 2 groups of a healthy group and a group with finding of major depressive illness.

Discrimination of the 2 groups of a healthy group and a group with finding of major depressive illness by this index was evaluated by the AUC of the ROC curve (FIG. 54), to give an AUC of 0.812±0.055 (95% confidence interval: 0.703 to 0.920), and this index was revealed to be an useful index with high diagnostic performance.

Then, a multivariate discriminant for maximizing the performance of discriminating the 2 groups of a healthy group and a group with finding of major depressive illness was searched by linear discriminate analysis (variable selection by a stepwise method of Wald test) to give a linear discriminate composed of Asn, Gln, Tau, Cit and ABA as an index (numerical coefficients of amino acid variables Asn, Gln, Tau, Cit and ABA and the constant term were −0.11, 0.005, 0.04, 0.08, −0.06 and −0.74, respectively). Besides, a plurality of linear discriminants having the same discrimination performance were obtained. These are shown in FIGS. 55, 56 and 57. The values of coefficients in the formulae in FIGS. 55, 56 and 57 may be those multiplied by a real number.

Figure 58:
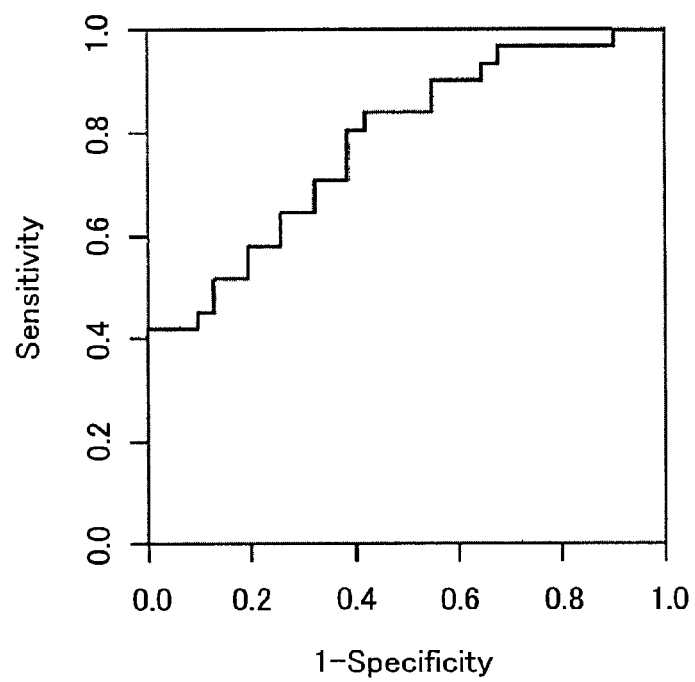
FIG. 58 is a graph showing a ROC curve for evaluation of diagnostic performance between the 2 groups of a healthy group and a group with finding of major depressive illness.

Discrimination of the 2 groups of a healthy group and a group with finding of major depressive illness by this index was evaluated by the AUC of the ROC curve (FIG. 58), to give an AUC of 0.780±0.059 (95% confidence interval: 0.665 to 0.896), and this index was revealed to be an useful index with high diagnostic performance.

From the foregoing results, it was revealed that a formula for accurate discrimination between a healthy group and a group with finding with major depressive illness can be derived from the generally used multivariable analysis method. As the variables in the multivariate discriminant for a healthy group and a group with finding of stress, non-amino acid data such as metabolome data (organic acid, fatty acid, nucleic acid etc.), transcriptome data, and proteome data can also be used in addition to amino acid variables in order to improve discrimination performance.

EXAMPLE 8

The sample data used in Example 1 were used. Using a method described in International Publication WO 2004/052191 that is an international application filed by the present applicant, an index for maximizing the performance of discriminating the 2 groups of a healthy group and a group with finding of major depressive illness was extensively searched to give index 7 in a plurality of indices having the same performance. Besides, a plurality of multivariate discriminants having the same discrimination performance as that of the index 7 were obtained. These are shown in FIGS. 59, 60 and 61.

Index 7: (Glu+Gln)/(Val+Thr+Ser)+(Cit+Met)/(Asn)

Figure 62:
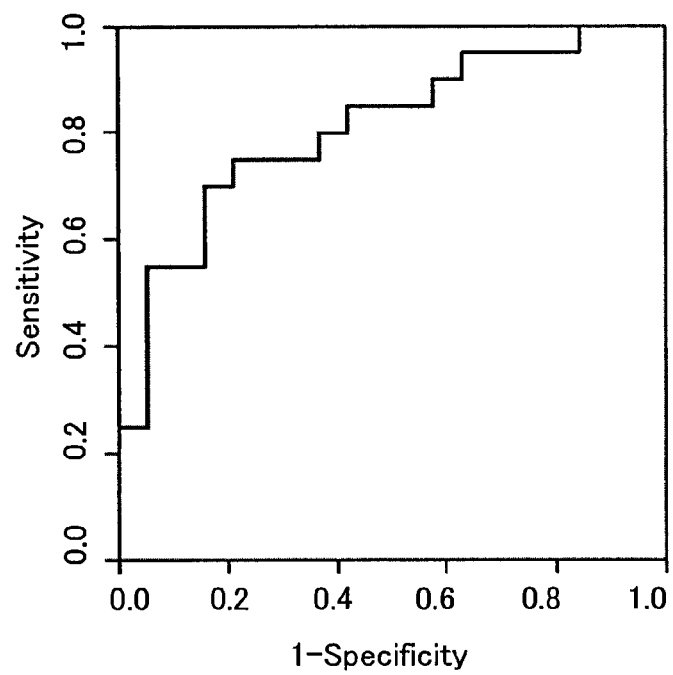
FIG. 62 is a graph showing a ROC curve for evaluation of diagnostic performance between the 2 groups of a healthy group and a group with finding of major depressive illness.

Discrimination of the 2 groups a healthy group and a group with finding of major depressive illness by the index 7 was evaluated by the AUC of the ROC curve (FIG. 62), to give an AUC of 0.849±0.071 (95% confidence interval: 0.668 to 0.947). When the optimum cutoff value for discrimination of the 2 groups of a healthy group and a group with finding of major depressive illness by the index 7 was determined assuming that the incidence in the group with finding of major depressive illness was 0.5, the cutoff value was 2.45, and the sensitivity was 70%; the specificity, 84%; and the correct diagnostic rate, 77%, and the index 7 was revealed to be an useful index with high diagnostic performance.

Then, an index for maximizing the performance of discriminating the 2 groups of a healthy group and a group with finding of major depressive illness was extensively searched to give index 8 in a plurality of indices having the same performance.

Index 8: (Asn/Gln)+(−0.014363)×(Cit/ABA)+(−0.045196)×(Glu/Arg)+(−0.80562)×(Met/BCAA)

Figure 63:
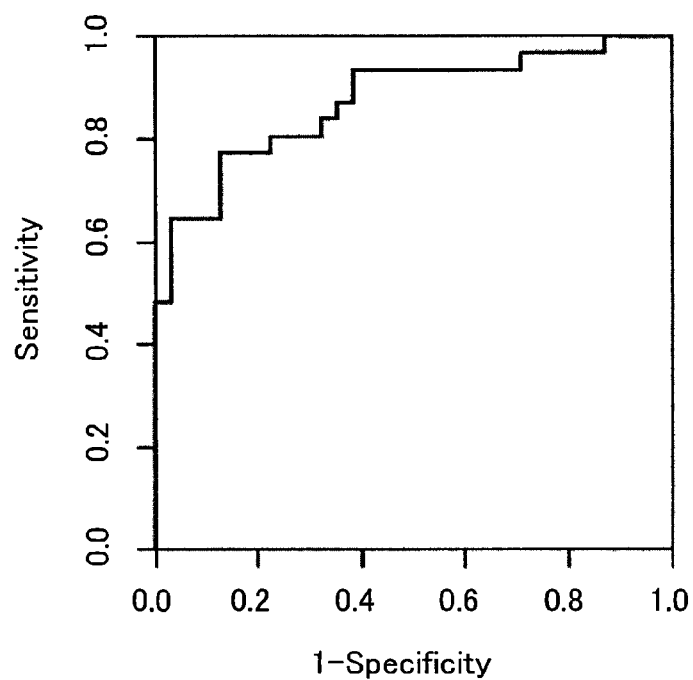
FIG. 63 is a graph showing a ROC curve for evaluation of diagnostic performance between the 2 groups of a healthy group and a group with finding of major depressive illness.

Discrimination of the 2 groups a healthy group and a group with finding of major depressive illness by the index 8 was evaluated by the AUC of the ROC curve (FIG. 63), to give an AUC of 0.873±0.046 (95% confidence interval: 0.783 to 0.963). When the optimum cutoff value for discrimination of the 2 groups of a healthy group and a group with finding of major depressive illness by the index 8 was determined assuming that the incidence in the group with finding of major depressive illness was 0.5, the cutoff value was −0.020, and the sensitivity was 77%; the specificity, 87%; and the correct diagnostic rate, 82%, and the index 8 was revealed to be an useful index with high diagnostic performance.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating stress, comprising:
   an obtaining step of obtaining amino acid concentration data on concentration values of at least three amino acids in blood collected from a subject to be examined; and
   a concentration value criterion evaluating step of evaluating a stress state including at least a depressive illness or a major depressive illness in the subject, based on both (i) the concentration values of at least three amino acids which comprise at least two amino acids selected from the group consisting of Lys, His, ABA, Asn, Phe, Leu, Ile, Val, Trp, Tyr and Met contained in the amino acid concentration data of the subject obtained at the obtaining step and (ii) a multivariate discriminant containing at least the concentrations of the three amino acids as explanatory variables, wherein the multivariate discriminant does not include a fractional expression.

2. The method of evaluating stress according to claim 1, wherein the concentration value criterion evaluating step further includes a concentration value criterion discriminating step of discriminating between the depressive illness and a non-depressive illness or between the major depressive illness and a non-major depressive illness in the subject, based on the concentration values of at least two of Lys, His, ABA, Asn, Phe, Leu, Ile, Val, Trp, Tyr and Met contained in the amino acid concentration data of the subject obtained at the obtaining step.

3. The method of evaluating stress according to claim 1, wherein the concentration value criterion evaluating step further includes:
   a discriminant value calculating step of calculating a discriminant value that is a value of multivariate discriminant and corresponds to an evaluation result on the stress state in the subject, based on at least both the concentration values of at least two of Lys, His, ABA, Asn, Phe, Leu, Ile, Val, Trp, Tyr and Met contained in the amino acid concentration data of the subject obtained at the obtaining step and a previously established multivariate discriminant containing at least the concentration of the amino acid as an-explanatory variable; and
   wherein the multivariate discriminant contains the concentration values of at least two of Lys, His, ABA, Asn, Phe, Leu, Ile, Val, Trp, Tyr and Met as explanatory variables.

4. The method of evaluating stress according to claim 3, wherein the concentration value criterion evaluating step further includes a discriminant value criterion evaluating step of evaluating the stress state in the subject, based on the discriminant value calculated at the discriminant value calculating step;
   wherein the discriminant value criterion evaluating step further includes a discriminant value criterion discriminating step of discriminating between the depressive illness and a non-depressive illness or between the major depressive illness and a non-major depressive illness in the subject based on the discriminant value calculated at the discriminant value calculating step, and wherein
   (i) the multivariate discriminant contains at least two of Lys, His, ABA, Asn, Phe, Leu, Ile, Val, Trp, Tyr and Met as explanatory variables and,
   (ii) the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

5. The method of evaluating stress according to claim 4, wherein the multivariate discriminant in discriminating between the depressive illness and the non-depressive illness at the discriminant value criterion discriminating step is a logistic regression equation containing the concentration values of Ser, Glu, Cys and Lys as explanatory variables or a linear discriminant containing the concentration values of Ser, Glu, Cys and Lys as explanatory variables.

6. The method of evaluating stress according to claim 4, wherein the multivariate discriminant in discriminating between the major depressive illness and the non-major depressive illness at the discriminant value criterion discriminating step is a logistic regression equation containing the concentration values of Ser, Gln, Pro, ABA, Tyr and Trp as explanatory variables, a logistic regression equation containing the concentration values of Glu, Asn, Gln, Cit and ABA as explanatory variables, a linear discriminant containing the concentration values of Ser, Gln, Pro, ABA, Cys, Ile, Tyr and Trp as explanatory variables or a linear discriminant containing the concentration values of Asn, Gln, Tau, Cit and ABA as explanatory variables.

7. The method of evaluating stress according to claim 3, wherein the concentration value criterion evaluating step further includes a discriminant value criterion evaluating step of evaluating the stress state in the subject, based on the discriminant value calculated at the discriminant value calculating step.

8. The method of claim 1, wherein the subject is determined as having the major depressive illness when the subject has at least 5 of the following 9 conditions simultaneously and continuously for 2 weeks or more:
   A: feels low most of the day;
   B: not interested in anything and not feel comfortable;
   C: loss of appetite or significant increase and decrease in body weight;
   D: has difficulty in sleeping or is wakened at midnight and early morning;
   E: slow in action and speech or seems frustrated or restless;
   F: feels fatigue and feels low;
   G: feels no value in oneself or feels guilty;

H: cannot focus on one's work or household work and cannot make a decision; and

I: wishes sometimes to disappear from the earth.

9. The method of claim 1, wherein the multivariate discriminant is a logistic regression equation containing the concentration value of Trp as an explanatory variable.

10. The method of claim 1, wherein the multivariate discriminant is a logistic regression equation containing the concentration values of Trp and Tyr as explanatory variables.

11. The method of claim 1, wherein the multivariate discriminant is a logistic regression equation containing the concentration values of Trp, Tyr and Phe as explanatory variables.

12. A stress-evaluating apparatus comprising a control unit and a memory unit, wherein the control unit includes:
   a discriminant value-calculating unit configured to calculate a discriminant value that is a value of multivariate discriminant and corresponds to an evaluating result on a stress state including at least a depressive illness or a major depressive illness in a subject to be evaluated, at least based on both (i) concentration values of at least three amino acids which comprise at least two amino acids selected from the group consisting of Lys, His, ABA, Asn, Phe, Leu, Ile, Val, Trp, Tyr and Met contained in previously obtained amino acid concentration data on the concentration values of at least three amino acids in the subject and (ii) a multivariate discriminant which contains at least the concentrations of the three amino acids as explanatory variables and is stored in the memory unit; and
   a discriminant value criterion-evaluating unit configured to evaluate the stress state of the subject, based on the discriminant value calculated by the discriminant value-calculating unit;
   wherein the multivariate discriminant contains the concentration values of at least two of Lys, His, ABA, Asn, Phe, Leu, Ile, Val, Trp, Tyr and Met as explanatory variables and does not include a fractional expression.

13. The stress-evaluating apparatus according to claim 12, wherein the control unit further includes a discriminant value criterion-evaluating unit configured to evaluate the stress state in the subject based on the discriminant value calculated by the discriminant value-calculating unit;
   wherein the discriminant value criterion-evaluating unit further includes a discriminant value criterion-discriminating unit configured to discriminate between the depressive illness and a non-depressive illness or between the major depressive illness and a non-major depressive illness in the subject based on the discriminant value calculated by the discriminant value-calculating unit, and wherein
   (i) the multivariate discriminant contains the concentration values of at least two of Lys, His, ABA, Asn, Phe, Leu, Ile, Val, Trp, Tyr and Met as explanatory variables,
   (ii) the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

14. The stress-evaluating apparatus according to claim 13, wherein the multivariate discriminant in the discriminant value criterion-discriminating unit discriminating between the depressive illness and the non-depressive illness is a logistic regression equation containing the concentration values of Ser, Glu, Cys and Lys as explanatory variables or a linear discriminant comprising the concentration values of Ser, Glu, Cys and Lys as explanatory variables.

15. The stress-evaluating apparatus according to claim 13, wherein the multivariate discriminant in the discriminant value criterion-discriminating unit discriminating between the major depressive illness and the non-major depressive illness is a logistic regression equation containing the concentration values of Ser, Gln, Pro, ABA, Tyr and Trp as explanatory variables, a logistic regression equation containing the concentration values of Glu, Asn, Gln, Cit and ABA as explanatory variables, a linear discriminant containing the concentration values of Ser, Gln, Pro, ABA, Cys, Ile, Tyr and Trp as explanatory variables or a linear discriminant comprising the concentration values of Asn, Gln, Tau, Cit and ABA as explanatory variables.

16. The stress-evaluating apparatus according to claim 12, wherein the control unit further includes a multivariate discriminant-preparing unit configured to prepare the multivariate discriminant to be stored in the memory unit, based on stress state information containing the amino acid concentration data and stress state index data on an index for indicating the stress state stored in the memory unit,
   wherein the multivariate discriminant-preparing unit further includes:
      a candidate multivariate discriminant-preparing unit configured to prepare a candidate multivariate discriminant that is a candidate of the multivariate discriminant, based on a predetermined discriminant-preparing method from the stress state information;
      a candidate multivariate discriminant-verifying unit configured to verify the candidate multivariate discriminant prepared by the candidate multivariate discriminant-preparing unit, based on a predetermined verifying method; and
      a variable-selecting unit configured to select a variable of the candidate multivariate discriminant based on a predetermined variable-selecting method, thereby selecting a combination of the amino acid concentration data contained in the stress state information used in preparing the candidate multivariate discriminant, and
   wherein the multivariate discriminant-preparing unit is configured to prepare the multivariate discriminant by selecting the candidate multivariate discriminant used as the multivariate discriminant from a plurality of the candidate multivariate discriminants, based on the verification results accumulated from repeatedly executing the candidate multivariate discriminant-preparing unit, the candidate multivariate discriminant-verifying unit and the variable-selecting unit.

17. A stress-evaluating method carried out with an information processing apparatus including a control unit and a memory unit, the method comprising:
   (i) a discriminant value calculating step of calculating a discriminant value that is a value of multivariate discriminant and corresponds to an evaluating result on a stress state including at least a depressive illness or a major depressive illness in a subject to be evaluated, at least based on both (a) the concentration values of at least three amino acids which comprise at least two amino acids selected from the group consisting of Lys, His, ABA, Asn, Phe, Leu, Ile, Val, Trp, Tyr and Met contained in previously obtained amino acid concentration data on the concentration values of at least three amino acids in the subject and (b) a multivariate discriminant which contains at least the concentrations of the three amino acids as explanatory variables and is stored in the memory unit;
(ii) a discriminant value criterion evaluating step of evaluating the stress state in the subject, based on the discriminate value calculated at the discriminant value calculating step, wherein the discriminant value criterion evaluating step is executed by the control unit
wherein (i) and (ii) are executed by the control unit, and the multivariate discriminant contains the concentration values of at least two of Lys, His, ABA, Asn, Phe, Leu, Ile, Val, Trp, Tyr and Met as explanatory variables and does not include a fractional expression.

18. The stress-evaluating method according to claim 17, wherein the method further includes a discriminant value criterion evaluating step of evaluating the stress state in the subject, based on the discriminant value calculated at the discriminant value calculating step, wherein the discriminant value criterion evaluating step is executed by the control unit;
wherein the discriminant value criterion evaluating step further includes a discriminant value criterion discriminating step of discriminating between the depressive illness and a non-depressive illness or between the major depressive and a non-major depressive illness in the subject based on the discriminant value calculated at the discriminant value calculating step,
wherein (i) the multivariate discriminant contains the concentration values of at least two of Lys, His, ABA, Asn, Phe, Leu, Ile, Val, Trp, Tyr and Met as explanatory variables, and
(ii) the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

19. The stress-evaluating method according to claim 18, wherein the multivariate discriminant in discriminating between the depressive illness and the non-depressive illness at the discriminant value criterion discriminating step is a logistic regression equation containing the concentration values of Ser, Glu, Cys and Lys as explanatory variables or a linear discriminant containing the concentration values of Ser, Glu, Cys and Lys as explanatory variables.

20. The stress-evaluating method according to claim 18, wherein the multivariate discriminant in discriminating between the major depressive illness and the non-major depressive illness at the discriminant value criterion discriminating step is a logistic regression equation containing the concentration values of Ser, Gln, Pro, ABA, Tyr and Trp as explanatory variables, a logistic regression equation containing the concentration values of Glu, Asn, Gln, Cit and ABA as explanatory variables, a linear discriminant containing the concentration values of Ser, Gln, Pro, ABA, Cys, Ile, Tyr and Trp as explanatory variables or a linear discriminant containing the concentration values of Asn, Gln, Tau, Cit and ABA as explanatory variables.

21. The stress-evaluating method according to claim 17, wherein the method further includes a multivariate discriminant preparing step of preparing the multivariate discriminant to be stored in the memory unit, based on stress state information containing amino acid concentration data and stress state index data on an index for indicating the stress state stored in the memory unit, that is executed by the control unit,
wherein the multivariate discriminant preparing step further includes:
a candidate multivariate discriminant preparing step of preparing a candidate multivariate discriminant that is a candidate of the multivariate discriminant, based on a predetermined discriminant-preparing method from the stress state information;
a candidate multivariate discriminant verifying step of verifying the candidate multivariate discriminant prepared at the candidate multivariate discriminant preparing step, based on a predetermined verifying method; and
a variable selecting step of selecting a variable of the candidate multivariate discriminant based on a predetermined variable-selecting method, thereby selecting a combination of the amino acid concentration data contained in the stress state information used in preparing the candidate multivariate discriminant, and
wherein at the multivariate discriminant preparing step, the multivariate discriminant is prepared by selecting the candidate multivariate discriminant used as the multivariate discriminant from a plurality of the candidate multivariate discriminants, based on the verification results accumulated from repeatedly executing the candidate multivariate discriminant preparing step, the candidate multivariate discriminant verifying step and the variable selecting step.

22. A stress-evaluating system comprising a stress-evaluating apparatus including a control unit and a memory unit and an information communication terminal apparatus that provides amino acid concentration data on the concentration values of at least three amino acids in a subject to be evaluated connected to each other communicatively via a network,
wherein the information communication terminal apparatus including:
an amino acid concentration data-sending unit configured to transmit the amino acid concentration data of the subject to the stress-evaluating apparatus; and
a result-receiving unit configured to receive a discriminant value that is a value of multivariate discriminant and corresponds to an evaluation result on a stress state including at least a depressive illness or a major depressive illness in the subject transmitted from the stress-evaluating apparatus, and
wherein the control unit of the stress-evaluating apparatus includes:
an amino acid concentration data-receiving unit configured to receive the amino acid concentration data of the subject transmitted from the information communication terminal apparatus;
a discriminant value-calculating unit configured to calculate the discriminant value, at least based on both (i) the concentration values of at least three amino acids which comprise at least two amino acids selected from the group consisting of Lys, His, ABA, Asn, Phe, Leu, Ile, Val, Trp, Tyr and Met contained in the amino acid concentration data of the subject received by the amino acid concentration data-receiving unit and (ii) a multivariate discriminant for evaluating the stress state which contains at least the concentrations of the three amino acids as explanatory variables and is stored in the memory unit; and
a result-sending unit configured to transmit the discriminant value calculated by the discriminant value-calculating unit to the information communication terminal apparatus, and wherein the multivariate discriminant contains at least two of Lys, His, ABA, Asn, Phe, Leu, Ile, Val, Trp, Tyr and Met as explanatory variables and does not include a fractional expression.

23. The stress-evaluating system according to claim 22, wherein the control unit of the stress-evaluating apparatus further includes a discriminant value criterion-evaluating unit that configured to evaluate the stress state in the subject, based on the discriminant value calculated by the discriminate value-calculating unit,
the result-sending unit is configured to transmit the evaluation result of the subject obtained by the discriminant value criterion-evaluating unit to the information communication terminal apparatus, and
the result-receiving unit is configured to receive the evaluation result of the subject transmitted from the stress-evaluating apparatus.

24. A non-transitory computer readable recording medium, comprising a stress-evaluating program recorded thereon, wherein the stress-evaluating program, when executed, makes an information processing apparatus including a control unit and a memory unit execute a method, the method comprising:
a discriminant value calculating step of calculating a discriminant value that is a value of multivariate discriminant and corresponds to an evaluation result on a stress state including at least a depressive illness or a major depressive illness in a subject to be evaluated, at least based on both (a) the concentration values of at least three amino acids which comprise at least two amino acids selected from the group consisting of Lys, His, ABA, Asn, Phe, Leu, Ile, Val, Trp, Tyr and Met contained in previously obtained amino acid concentration data on the concentration values of at least three amino acids in the subject and (b) a multivariate discriminant which contains at least the concentrations of the three amino acids as explanatory variables and is stored in the memory unit; and
wherein the discriminant value calculating is executed by the control unit, and
the multivariate discriminant contains the concentration values of at least two of Lys, His, ABA, Asn, Phe, Leu, Ile, Val, Trp, Tyr and Met as explanatory variables and does not include a fractional expression.

25. The non-transitory computer readable recording medium according to claim 24, wherein the method further includes a discriminant value criterion evaluating step of evaluating the stress state in the subject, based on the discriminate value calculated at the discriminant value calculating step, wherein the discriminant value criterion evaluating step is executed by the control unit.

26. An information communication terminal apparatus configured to provide amino acid concentration data on concentration values of at least three amino acids in a subject to be evaluated, wherein the information communication terminal apparatus comprises a control unit and a memory unit, the control unit comprising:
a result-obtaining unit configured to obtain a discriminant value that is a value of multivariate discriminant and corresponds to an evaluation result on a stress state including at least a depressive illness or a major depressive illness in the subject;
wherein the discriminant value is calculated at least based on both (i) the concentration values of at least three amino acids which comprise at least two amino acids selected from the group consisting of Lys, His, ABA, Asn, Phe, Leu, Ile, Val, Trp, Tyr and Met contained in the amino acid concentration data of the subject and (ii) the multivariate discriminant which contains at least the concentrations of the three of the amino acids as explanatory variables, wherein the multivariate discriminant does not include a fractional expression.

27. The information communication terminal apparatus according to claim 26, wherein the information communication terminal apparatus is communicatively connected via a network to a stress-evaluating apparatus to calculate the discriminant value,
the control unit of the information communication terminal apparatus further includes an amino acid concentration data-sending unit configured to transmit the amino acid concentration data of the subject to the stress-evaluating apparatus, and
the result-obtaining unit is configured to receive the discriminant value transmitted from the stress-evaluating apparatus.

28. The information communication terminal apparatus according to claim 27, wherein the stress-evaluating apparatus is configured to evaluate the stress state in the subject,
the result-obtaining unit is configured to receive the evaluation result of the stress state of the subject transmitted from the stress-evaluating apparatus, and
wherein the evaluation result is the result of evaluating the stress state in the subject based on the discriminant value.

29. The information communication terminal apparatus according to claim 26, wherein the result-obtaining unit is configured to obtain the evaluation result of the stress state of the subject, and the evaluation result is the result of evaluating the stress state in the subject based On the discriminant value.

30. A stress-evaluating apparatus comprising a control unit and a memory unit, communicatively connected via a network to an information communication terminal apparatus that provides amino acid concentration data on concentration values of at least three amino acids in a subject to be evaluated wherein the control unit of the stress-evaluating apparatus comprises:
an amino acid concentration data-receiving unit configured to receive the amino acid concentration data of the subject transmitted from the information communication terminal apparatus;
a discriminant value-calculating unit configured to calculate a discriminant value that is a value of multivariate discriminant and corresponds to an evaluation result on a stress state including at least a depressive illness or a major depressive illness in the subject, at least based on both (i) the concentration values of at least three amino acids which comprise at least two amino acids selected from the group consisting of Lys, His, ABA, Asn, Phe, Leu, Ile, Val, Trp, Tyr and Met contained in the amino acid concentration data of the subject received by the amino acid concentration data-receiving unit and (ii) the multivariate discriminant which contains at least the concentrations of the three of the amino acids as explanatory variables, wherein the multivariate discriminant does not include a fractional expression, and
a result-sending unit configured to transmit the discriminant value calculated by the discriminant value-calculating unit to the information communication terminal apparatus.

31. The stress-evaluating apparatus according to claim 30, wherein the control unit of the stress-evaluating apparatus further includes a discriminant value criterion-evaluating unit configured to evaluate the stress state in the subject based on the discriminant value calculated by the discriminant value-calculating unit, and the result-sending unit is configured to transmit the evaluation result of the subject obtained by the discriminate value criterion evaluating unit to the information communication terminal apparatus.

* * * * *